US011759216B2

(12) United States Patent
Metcalfe et al.

(10) Patent No.: US 11,759,216 B2
(45) Date of Patent: Sep. 19, 2023

(54) ORTHOPAEDIC FUSION PLANNING SYSTEMS AND METHODS OF REPAIR

(71) Applicant: Arthrex, Inc., Naples, FL (US)

(72) Inventors: Nick Metcalfe, Bonita Springs, FL (US); Scott William Doody, Bonita Springs, FL (US); Adam Garlock, Naples, FL (US)

(73) Assignee: ARTHREX, INC., Naples, FL (US)

( * ) Notice: Subject to any disclaimer, the term of this patent is extended or adjusted under 35 U.S.C. 154(b) by 86 days.

(21) Appl. No.: 17/482,103

(22) Filed: Sep. 22, 2021

(65) Prior Publication Data

US 2023/0087313 A1 Mar. 23, 2023

(51) Int. Cl.
*A61B 17/17* (2006.01)
*A61B 34/10* (2016.01)
*A61B 90/00* (2016.01)

(52) U.S. Cl.
CPC ...... *A61B 17/1775* (2016.11); *A61B 17/1703* (2013.01); *A61B 34/10* (2016.02); *A61B 90/03* (2016.02); *A61B 2034/102* (2016.02); *A61B 2034/105* (2016.02); *A61B 2034/107* (2016.02); *A61B 2090/035* (2016.02)

(58) Field of Classification Search
CPC .............. A61B 34/10; A61B 2034/105; A61B 2034/102; A61B 17/15; A61B 17/151; A61B 17/152; A61B 17/154; A61B 17/155; A61B 17/157; A61B 17/158; A61B 17/1775; A61B 17/1764; A61B 17/1739; A61B 17/1742; A61B 17/1757; A61B 17/176; A61B 17/1767; A61B 17/1778; A61B 17/1782; A61B 17/1792
See application file for complete search history.

(56) References Cited

U.S. PATENT DOCUMENTS

| 5,824,085 | A  | 10/1998 | Sahay et al. |
|---|---|---|---|
| 6,917,827 | B2 | 7/2005 | Kienzle, III |
| 7,194,295 | B2 | 3/2007 | Vilsmeier |
| 8,160,325 | B2 | 4/2012 | Zug et al. |
| 8,214,016 | B2 | 7/2012 | Lavallee et al. |
| 8,331,634 | B2 | 12/2012 | Barth et al. |

(Continued)

FOREIGN PATENT DOCUMENTS

| EP | 2702953 | 3/2014 |
|---|---|---|
| WO | 2005089681 | 9/2005 |

(Continued)

OTHER PUBLICATIONS

Brochure. Tornier Blueprint 3D Planning + PSI: Surgical Technique v.2.1—Polyamide. Wright Focused Excellence. Feb. 2017. Retrieved from: http://www.wrightemedia.com/ProductFiles/Files/PDFs/CAW-8609_EN_HR_LE.pdf.

(Continued)

*Primary Examiner* — Samuel S Hanna
(74) *Attorney, Agent, or Firm* — Carlson, Gaskey & Olds, P.C.

(57) ABSTRACT

This disclosure relates to surgical planning systems, instrumentation and methods for repairing bone defects. The planning systems and instrumentation disclosed herein may be utilized to establish trajectories of surgical devices and may be utilized to establish resection surfaces for fusion of adjacent bone surfaces.

35 Claims, 30 Drawing Sheets

(56) References Cited

U.S. PATENT DOCUMENTS

| | | | |
|---|---|---|---|
| 8,382,765 | B2 | 2/2013 | Axelson et al. |
| 8,706,197 | B2 | 4/2014 | Henning et al. |
| 9,173,665 | B2 | 11/2015 | Couture |
| 9,211,199 | B2 | 12/2015 | Ratron |
| 9,299,138 | B2 | 3/2016 | Zellner et al. |
| 9,498,234 | B2 | 11/2016 | Goldstein et al. |
| 9,741,263 | B2 | 8/2017 | Iannotti et al. |
| 10,070,928 | B2 | 9/2018 | Frank et al. |
| 10,102,309 | B2 | 10/2018 | McKinnon et al. |
| 10,159,530 | B2 | 12/2018 | Lang |
| 10,172,675 | B2 | 1/2019 | Mahfouz |
| 10,172,677 | B2 | 1/2019 | Wentorf et al. |
| 10,176,642 | B2 | 1/2019 | Tran et al. |
| 10,194,991 | B2 | 2/2019 | Bonny et al. |
| 10,251,705 | B2 | 4/2019 | Kumar et al. |
| 10,292,770 | B2 | 5/2019 | Ryan et al. |
| 10,314,653 | B2 | 6/2019 | Ikits et al. |
| 10,390,887 | B2 | 8/2019 | Bischoff et al. |
| 10,433,983 | B1 | 10/2019 | Khosla et al. |
| 10,470,821 | B2 | 11/2019 | Jaramaz et al. |
| 10,537,390 | B2 | 1/2020 | Varadarajan et al. |
| 10,575,875 | B2 | 3/2020 | Pavlovskaia et al. |
| 10,624,655 | B2 | 4/2020 | Iannotti et al. |
| 10,660,709 | B2 | 5/2020 | Chaoui |
| 10,687,856 | B2 | 6/2020 | Park et al. |
| 10,705,677 | B2 | 7/2020 | Andersson et al. |
| 10,736,697 | B2 | 8/2020 | Chaoui et al. |
| 2004/0102866 | A1 | 5/2004 | Harris et al. |
| 2005/0038338 | A1 | 2/2005 | Bono et al. |
| 2005/0256389 | A1 | 11/2005 | Koga et al. |
| 2007/0066917 | A1 | 3/2007 | Hodorek et al. |
| 2007/0179626 | A1 | 8/2007 | de la Barrera et al. |
| 2007/0191741 | A1 | 8/2007 | Tsai et al. |
| 2008/0033571 | A1 | 2/2008 | Tuke |
| 2008/0058945 | A1 | 3/2008 | Hajaj et al. |
| 2009/0089034 | A1 | 4/2009 | Penney et al. |
| 2010/0030231 | A1 | 2/2010 | Revie et al. |
| 2012/0277745 | A1 | 11/2012 | Lizee |
| 2013/0172898 | A1 | 7/2013 | Iannotti et al. |
| 2014/0324182 | A1 | 10/2014 | Graumann et al. |
| 2016/0045317 | A1 | 2/2016 | Lang et al. |
| 2017/0367764 | A1 | 12/2017 | Zuhars et al. |
| 2018/0153624 | A1 | 6/2018 | Hughes et al. |
| 2018/0358120 | A1 | 12/2018 | Schoenefeld et al. |
| 2018/0360544 | A1 | 12/2018 | Vanheule et al. |
| 2019/0046326 | A1 | 2/2019 | Ball |
| 2019/0105169 | A1 | 4/2019 | Sperling |
| 2019/0175277 | A1 | 6/2019 | Chav et al. |
| 2019/0380792 | A1 | 12/2019 | Poltaretskyi et al. |
| 2019/0388123 | A1* | 12/2019 | Pavlovskaia ............ G06T 19/00 |
| 2020/0030034 | A1 | 1/2020 | Kontaxis et al. |
| 2020/0074748 | A1 | 3/2020 | de Almeida Barreto et al. |
| 2020/0205898 | A1 | 7/2020 | Hampp et al. |
| 2020/0205900 | A1 | 7/2020 | Buckland et al. |
| 2021/0068844 | A1 | 3/2021 | Lo et al. |

FOREIGN PATENT DOCUMENTS

| | | |
|---|---|---|
| WO | 2010068212 | 6/2010 |
| WO | 2015018921 | 2/2015 |
| WO | 2017204832 | 11/2017 |
| WO | 2019148154 | 8/2019 |
| WO | 2020102886 | 5/2020 |
| WO | 2020163328 | 8/2020 |

OTHER PUBLICATIONS

Magosch, P., Habermeyer, P., Bachmaier, S., Metcalfe, N. (2012). Biomechanical basics of the metaphyseal anchored humeral head replacement. Springer-Verlag. 2012. pp. 1-6. (Machine translation—Google).

Haddad, MD, S.L., Coetzee, MD, J.C., Estok, RN, BSN, R., Fahrbach, PhD, K., Banel, BA, D., and Nalysnyk, MD, Mph, L. (2007). Intermediate and long-term outcomes of total ankle arthroplasty and ankle arthrodesis. The Journal of Bone and Joint Surgery vol. 89(9). Sep. 7, 2007. pp. 1899-1905.

Glazebrook, MD, M., Beasley, CCR, W., Daniels, MD, T., Evangelista, MD, P.T., Donahue, PhD, R., Younger, MD, MSc, A., Pinzur, MD, M.S., Baumhauer, MD, Mph, J.F., and Digiovanni, MD, C.W. (2013). Establishing the relationship between clinical outcome and extent of osseous bridging between computed tomography assessment in isolated hindfoot and ankle fusions. Foot & Ankle International. vol. 34(12). pp. 1612-1618.

Chen, MD, Mph, J., Akoh, MD, C.C., Kadakia, MD, R., Somerson, MD, J.S., Easley, MD, M.E., Adams, MD, S.B., Deorio, MD, J.K., and Nunley, MD, J.A. (2020). Analysis of 408 total ankle arthroplasty adverse events reported to the US Food and Drug Administration from 2015 to 2018. Foot & Ankle Specialist. May 8, 2020. pp. 1-8.

International Search Report and Written Opinion for International Application No. PCT/US2022/043590 dated Feb. 13, 2023.

* cited by examiner

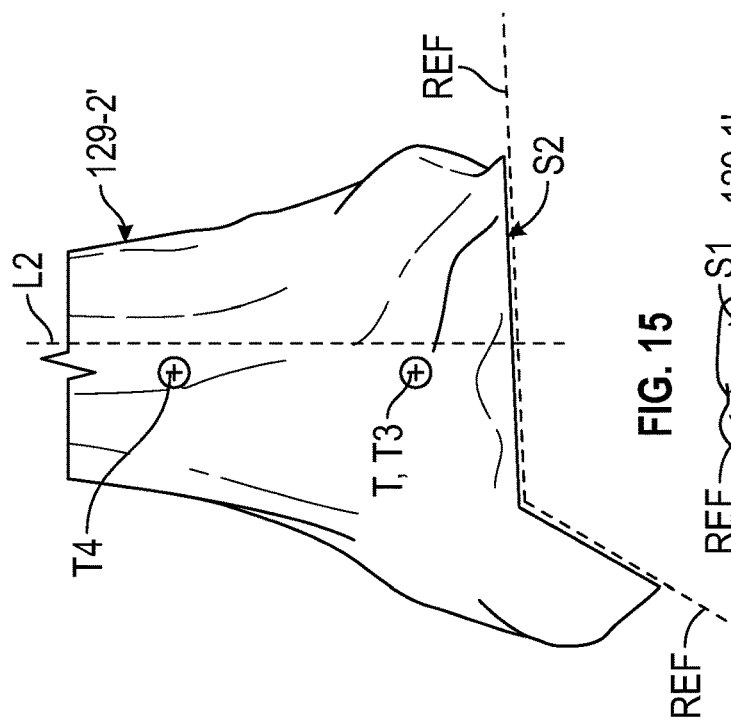
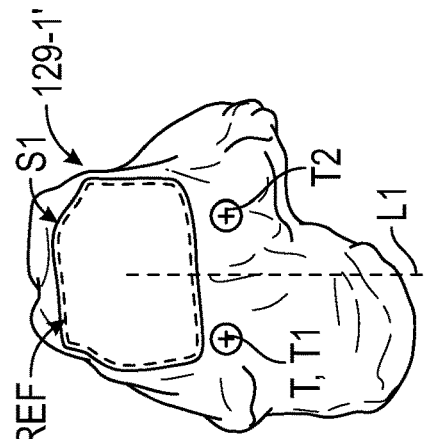
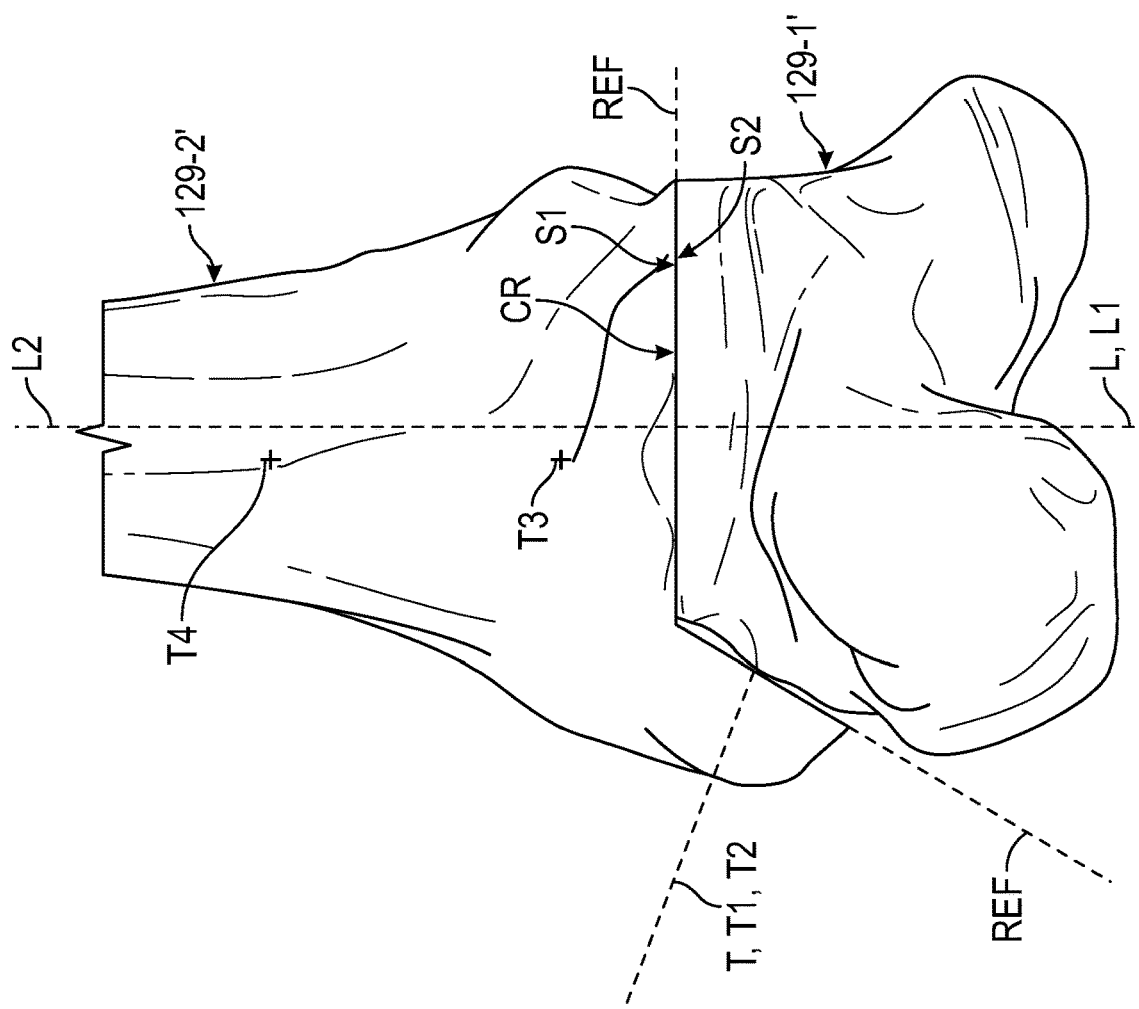
FIG. 14
FIG. 15
FIG. 16

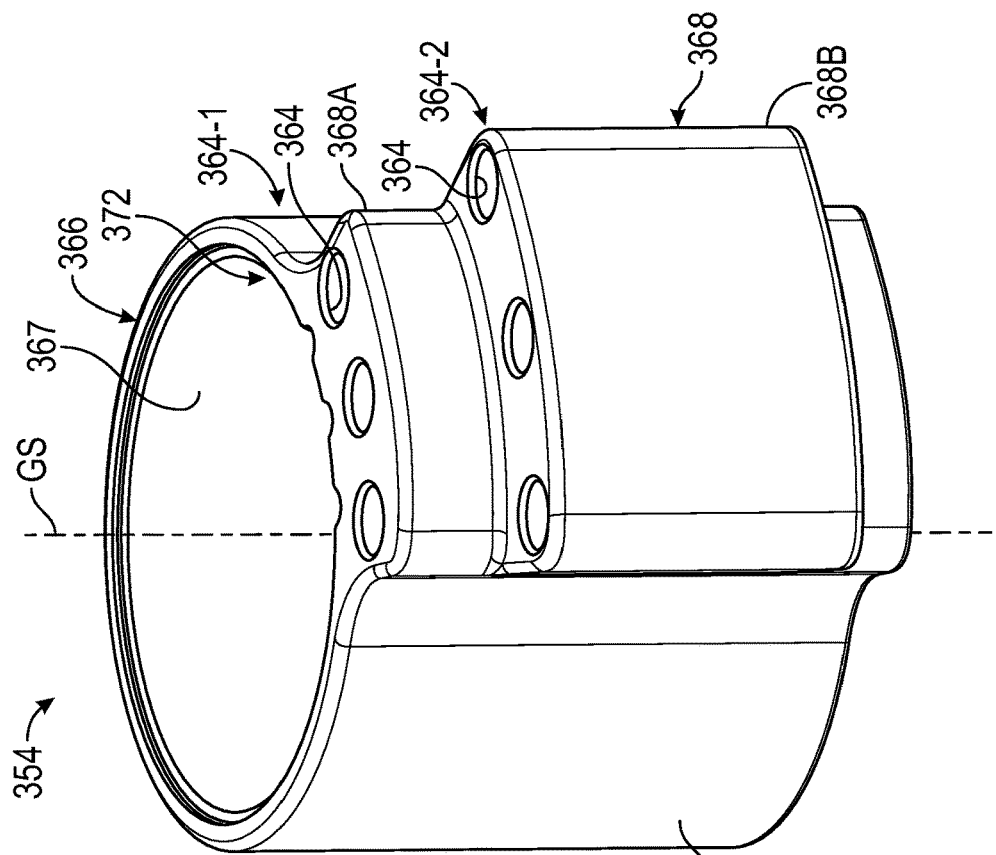
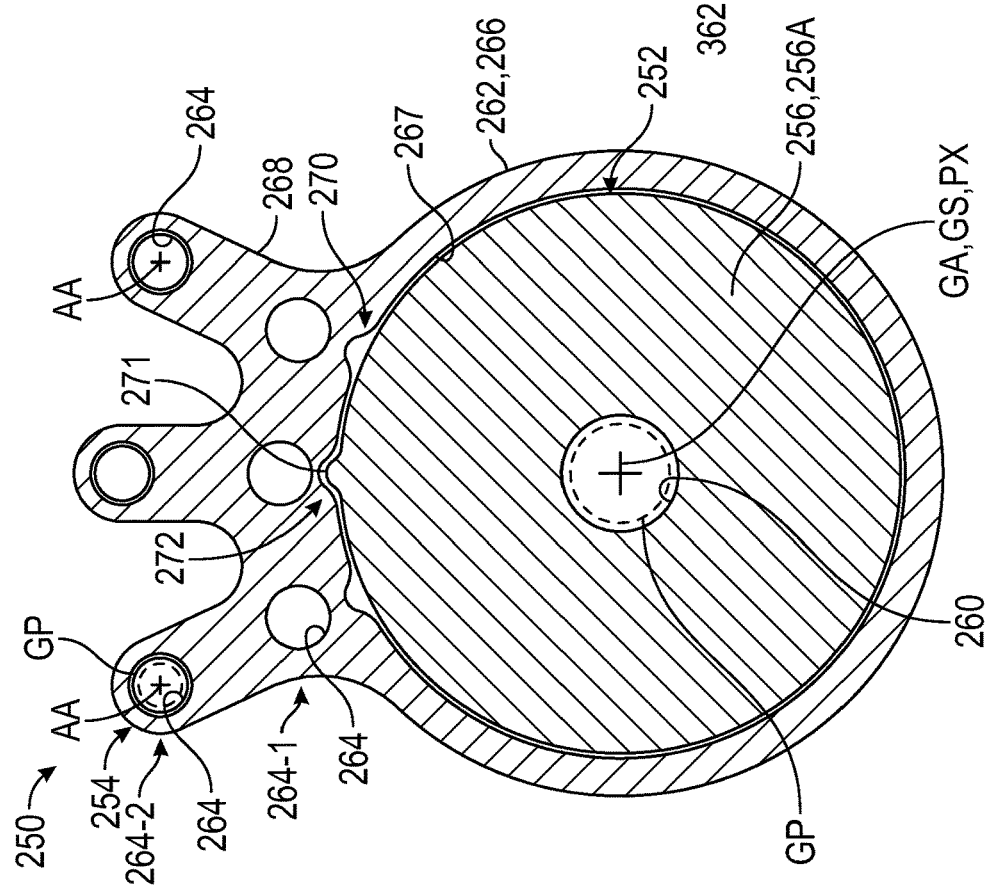
FIG. 19
FIG. 18

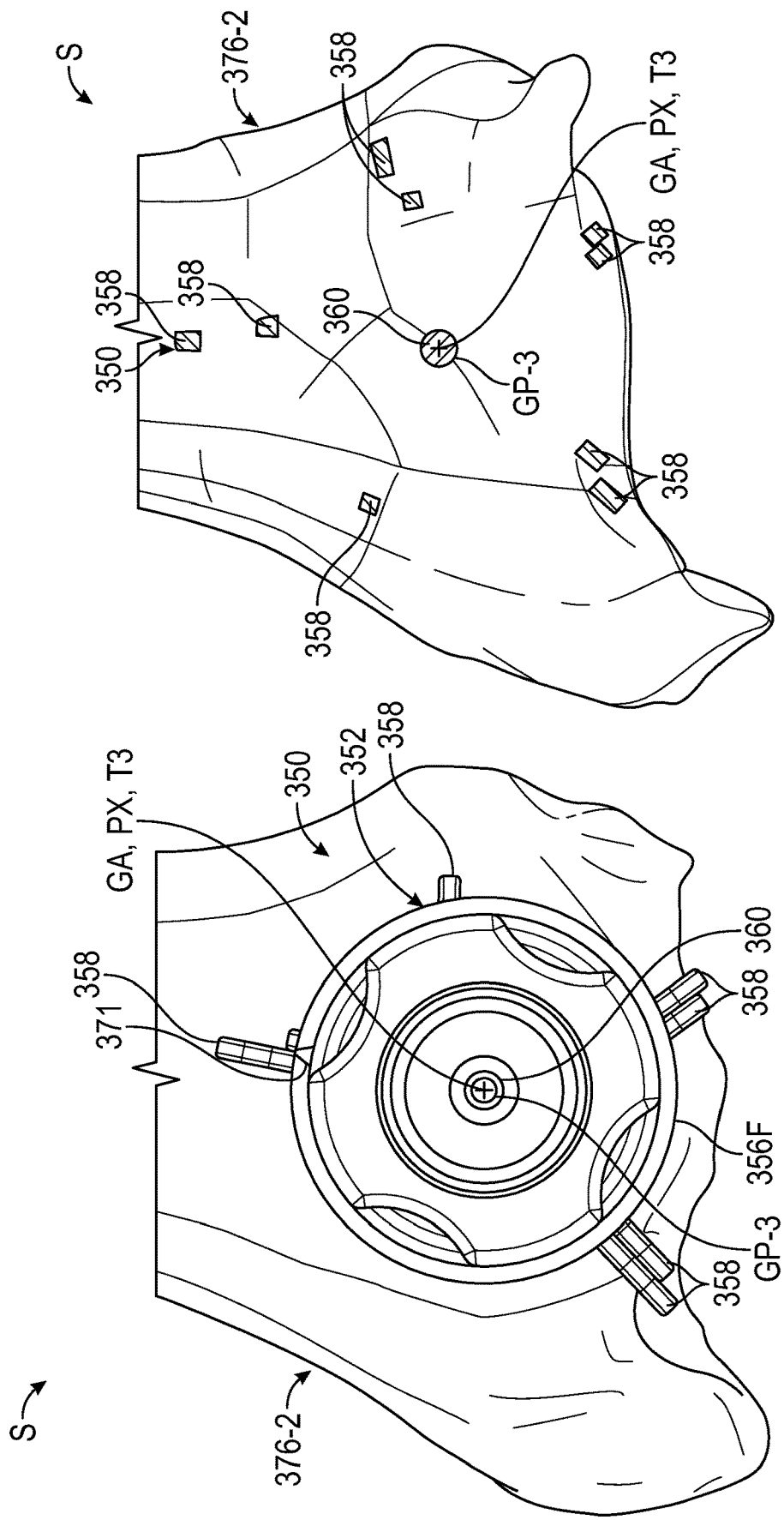

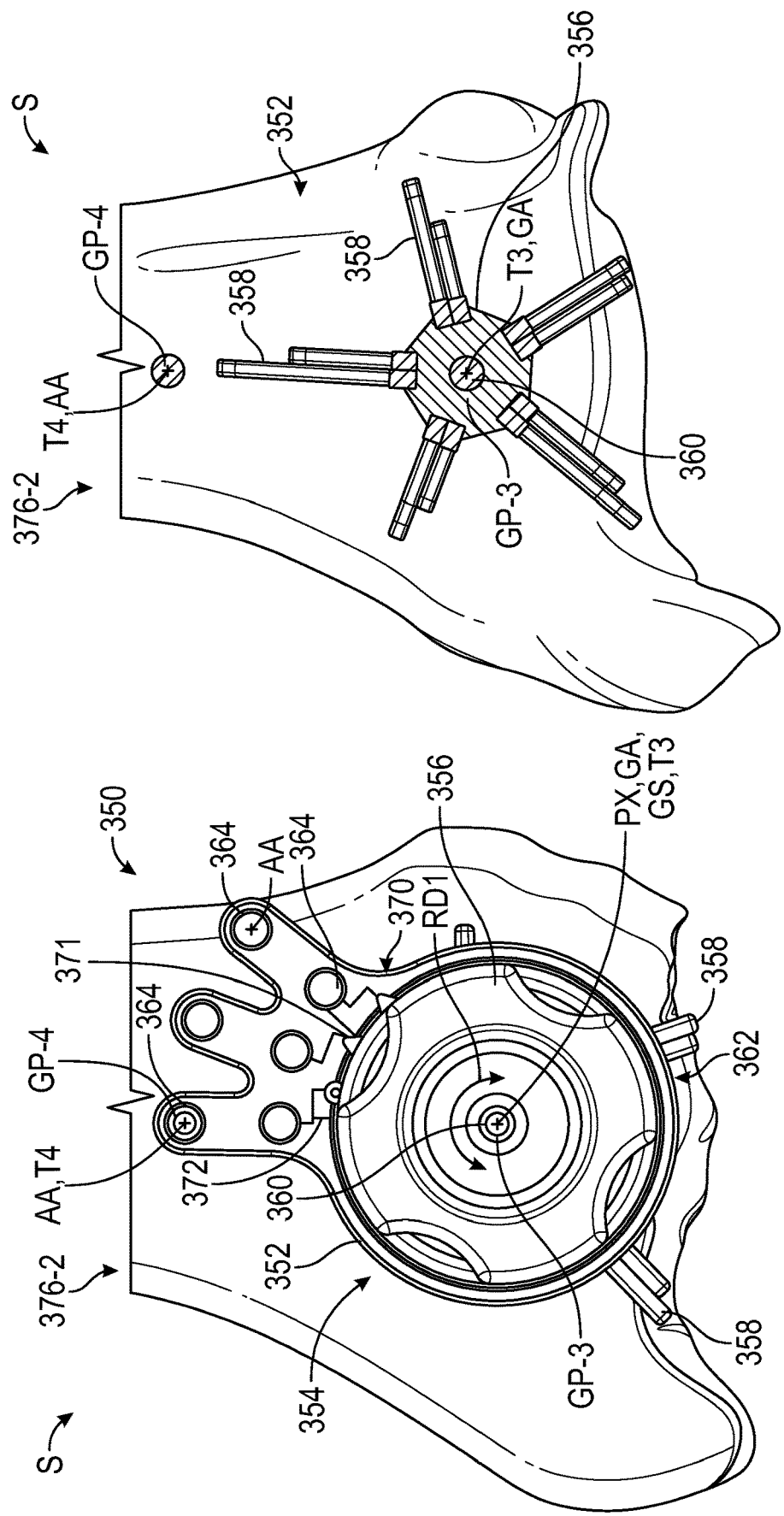

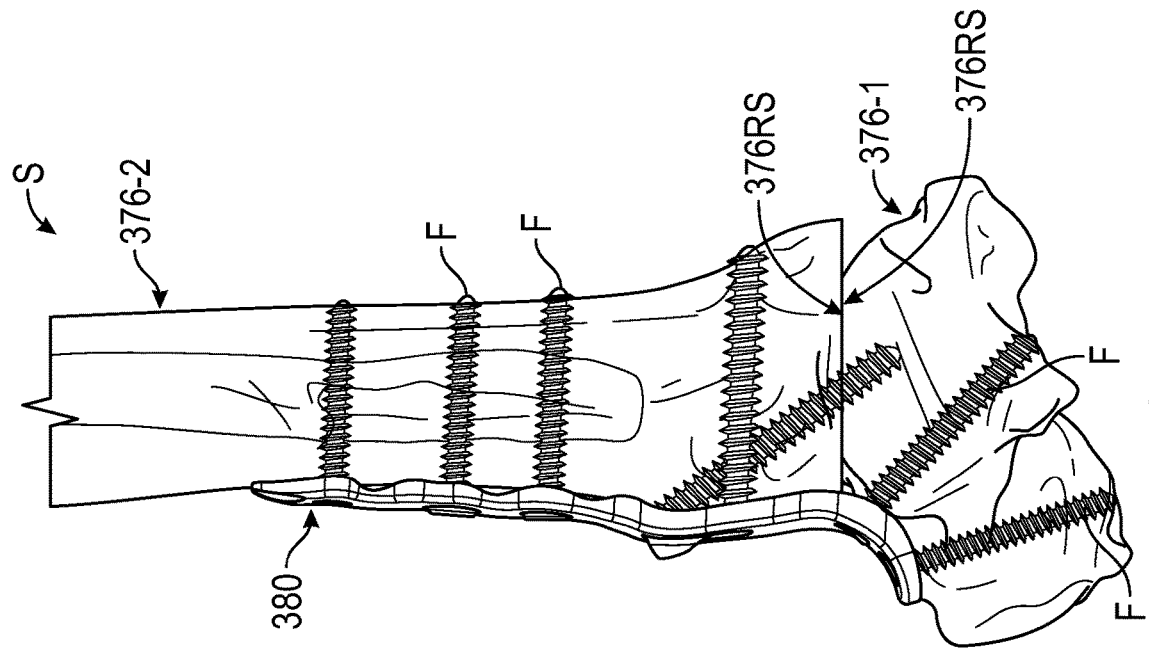
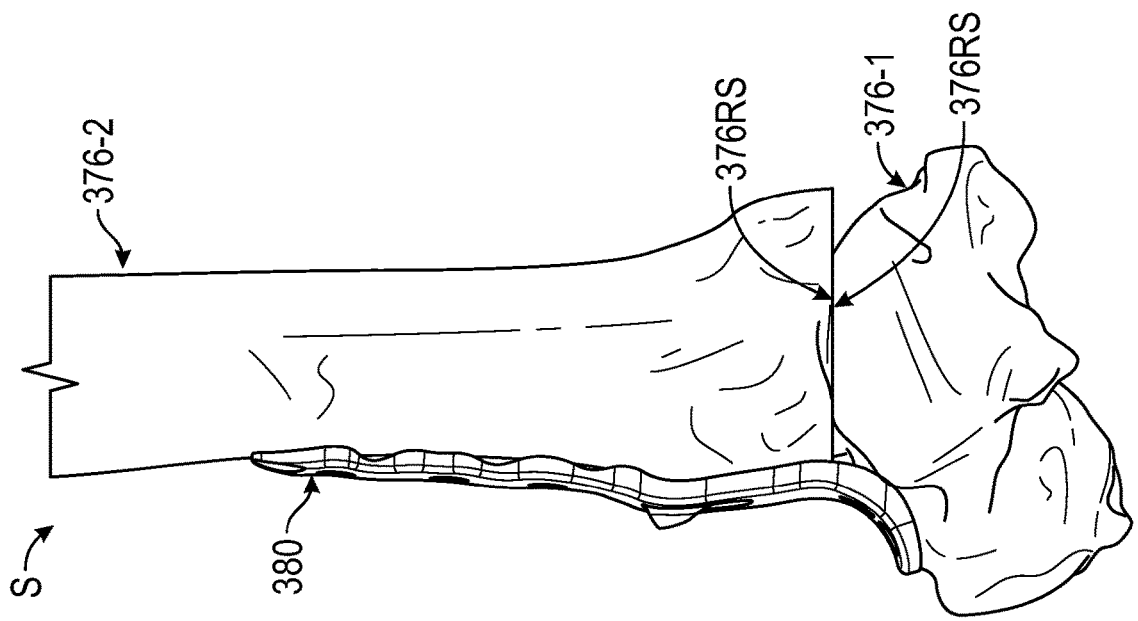

ORTHOPAEDIC FUSION PLANNING SYSTEMS AND METHODS OF REPAIR

BACKGROUND

This disclosure relates to surgical devices and methods for repairing bone defects along articular surfaces of a joint.

Many bones of the human musculoskeletal system include articular surfaces. The articular surfaces articulate relative to other bones to facilitate different types and degrees of joint movement. The articular surfaces can erode (e.g., experience bone loss) over time due to repeated use or wear or can fracture as a result of a traumatic impact. These types of bone defects can cause joint instability and pain.

Bone deficiencies may occur along the articular surfaces of ankle bones. Some techniques utilize a bone plate to fix the ankle bones to each other.

SUMMARY

This disclosure relates to planning systems and methods of performing a surgical procedure. The planning systems may be utilized for planning orthopaedic procedures to restore functionality to a joint, including determining contact areas between resection surfaces and establishing trajectories of surgical devices.

An assembly for preparation of a surgical site according to an implementation of the present disclosure includes, inter alia, a trajectory guide including a guide body and at least one arm member coupled to the guide body. The guide body may include a guide passage extending along a passage axis. The at least one arm member may be moveable relative to the guide body to set a trajectory of a first guide pin insertable through the guide passage relative to bone. A secondary guide may include a main body having at least one aperture. The at least one aperture may be dimensioned to at least partially receive a second guide pin along an aperture axis. The secondary guide may be coupled to the guide body such that the aperture axis may be offset from the passage axis.

A system for planning an orthopaedic procedure according to an implementation of the present disclosure includes, inter alia, a computing device including a processor coupled to a memory. The processor may be configured to execute a planning environment including a display module, a spatial module and a comparison module. The memory may be configured to store a plurality of bone models including a first bone model and a second bone model. The display module may be configured to display the first bone model and the second bone model in a graphical user interface. The spatial module may be configured to establish a first resection surface of the first bone model according to a first reference plane. The spatial module may be configured to establish a second resection surface of the second bone model along a second reference plane. The spatial module may be configured to position the first resection surface in contact with the second resection surface along a contact region. The comparison module may be configured to determine a contact area ratio. The contact area ratio may be defined as a first area of the first resection surface along the contact region divided by a second area of the second resection surface. The comparison module may be configured to generate a first indicator in response to the contact area ratio meeting a first predefined threshold.

A method of performing an orthopaedic procedure according to an implementation of the present disclosure includes, inter alia, selecting a first bone model and a second bone model from a plurality of bone models. The method may include displaying the first and second bone models in a graphical user interface such that a first articular surface of the first bone model opposes a second articular surface of the second bone model. The method may include setting a first reference plane in the graphical user interface to establish a first resection surface of the first bone model. The method may include setting a second reference plane in the graphical user interface to establish a second resection surface of the second bone model. The method may include generating a first iteration of the first and second bone models that may exclude respective volumes of the first and second bone models between the first and second reference planes and the first and second articular surfaces of the first and second bone models. The method may include positioning the first resection surface in contact with the second resection surface to establish a contact region. The method may include displaying the first iteration of the first and second bone models along the contact region in the graphical user interface. The method may include determining a contact area ratio. The contact area ratio may be defined as a first area of the first resection surface along the contact region divided by a second area of the second resection surface. The method may include displaying at least one indicator in the graphical user interface associated with the contact area ratio in response to meeting one or more predetermined criteria.

A method of performing an orthopaedic procedure according to an implementation of the present disclosure includes, inter alia, configuring a trajectory guide. The trajectory guide may include a guide body and at least one arm member coupled to the guide body. The guide body may include a guide passage extending along a passage axis. The method may include moving the at least one arm member from a first position to a second position relative to the guide body to establish a first trajectory along the passage axis. The method may include configuring a secondary guide. The secondary guide may include a main body having at least one aperture extending along an aperture axis. The method may include coupling the secondary guide to the guide body to establish a second trajectory along the aperture axis. The aperture axis may be offset from the passage axis. The method may include moving the trajectory guide into abutment with bone. The method may include positioning a first guide pin through the guide passage and then into the bone according to the first trajectory. The method may include positioning a second guide pin through the at least one aperture and then into the bone according to the second trajectory.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 14 illustrates exemplary trajectories for adjacent bone models.

FIG. 15 illustrates exemplary trajectories for one of the bone models of FIG. 14.

FIG. 16 illustrates exemplary trajectories for another one of the bone models of FIG. 14.

FIG. 18 illustrates a sectional view of the trajectory assembly of FIG. 17.

FIG. 19 illustrates an exemplary secondary guide.

FIG. 23 illustrates an end view of the trajectory assembly of FIG. 22.

FIG. 24 illustrates a sectional view of arm members of the trajectory assembly of FIG. 23.

FIG. 26 illustrates an end view of the trajectory assembly of FIG. 25.

FIG. 27 illustrates a sectional view of the trajectory assembly of FIG. 26.

FIG. 39 illustrates a side view of an implant positioned relative to adjacent bones.

FIG. 40 illustrates a side view of the implant secured to the adjacent bones of FIG. 39.

Like reference numbers and designations in the various drawings indicate like elements.

DETAILED DESCRIPTION

Figure 1:
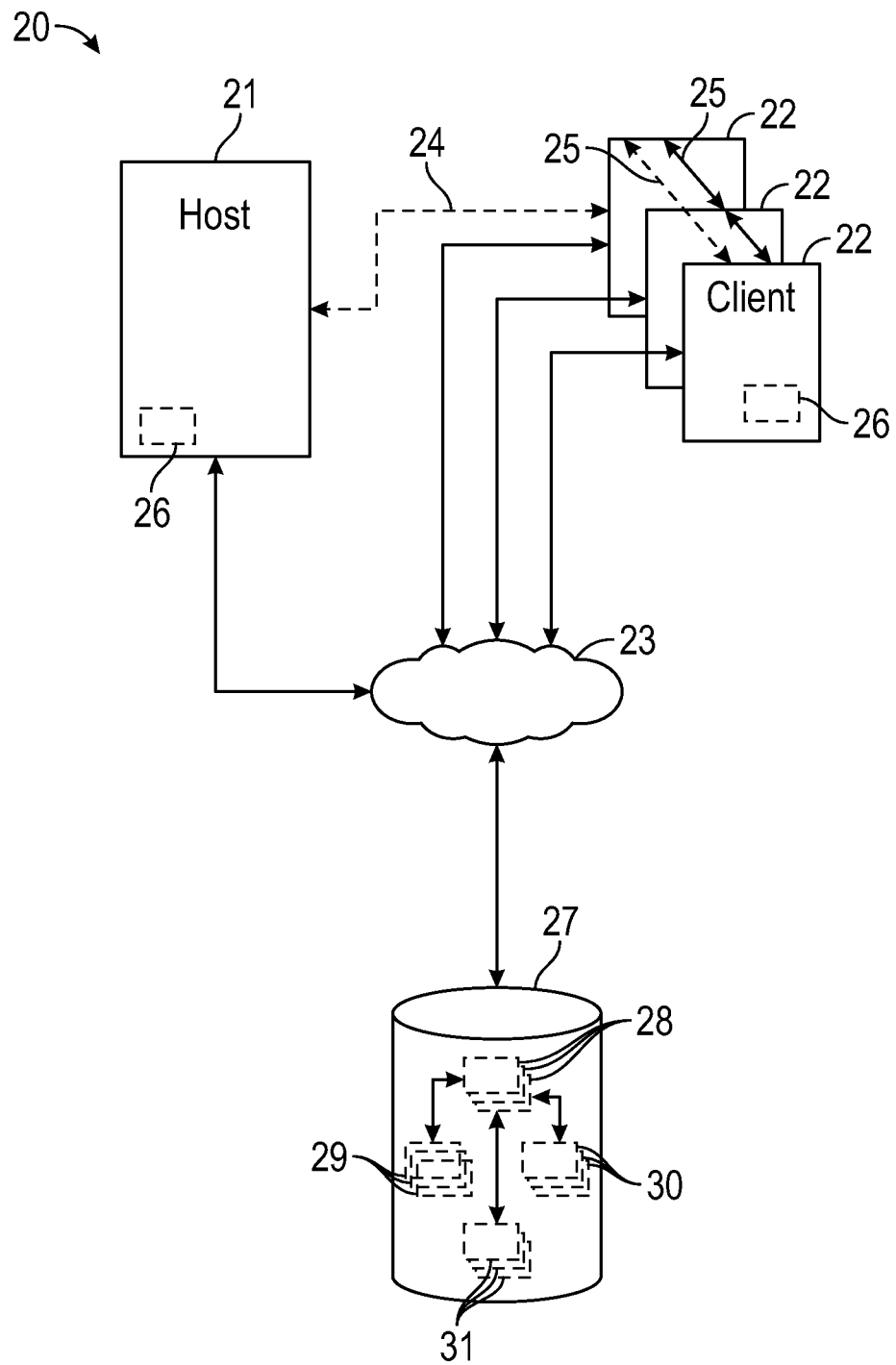
FIG. 1 illustrates an exemplary planning system.

This disclosure relates to surgical devices and methods for repairing bone defects. The instrumentation and systems described herein may be capable of dimensioning or otherwise preparing a defect surface at a surgical site, including resecting bone or other tissue.

The disclosed planning systems and methods may be utilized to determine resection characteristics and sufficiency of contact surfaces to promote bone fusion and stability. The surgeon or assistant may interact with the disclosed planning systems to set and adjust the resection characteristics, including adjusting resection planes associated with the selected bone models. The disclosed planning systems and methods may present the surgeon with parameters associated with the specified resection planes and other characteristics, including parameters associated with a contact area between the adjacent resection surfaces, cortical and cancellous coverage, and shortening of the respective bones. The surgeon may interact with the planning system to determine suitable bone contact at different resection depths and any effects of the resections on limb alignment and shortening. Aspects of a surgical plan can be established based on the parameters, including various settings and dimensions associated with instrumentation to prepare a surgical site. The disclosed trajectory assemblies may be utilized to establish a precise trajectory of guide members in a manner that substantially conforms to an associated surgical plan.

An assembly for preparation of a surgical site according to an implementation of the present disclosure includes, inter alia, a trajectory guide including a guide body and at least one arm member coupled to the guide body. The guide body may include a guide passage extending along a passage axis. The at least one arm member may be moveable relative to the guide body to set a trajectory of a first guide pin insertable through the guide passage relative to bone. A secondary guide may include a main body having at least one aperture. The at least one aperture may be dimensioned to at least partially receive a second guide pin along an aperture axis. The secondary guide may be coupled to the guide body such that the aperture axis may be offset from the passage axis.

In a further implementation, the aperture axis may be substantially parallel to the passage axis.

In a further implementation, the main body may extend along a guide axis. The at least one aperture may include a first row of apertures distributed about the guide axis.

In a further implementation, the at least one aperture may include a second row of apertures distributed about the guide axis. The second row of apertures may be outward of the first row of apertures relative to the guide axis.

In a further implementation, each aperture of the first row of apertures may be substantially circumferentially aligned with a respective aperture of the second row of apertures relative to the guide axis.

In a further implementation, the main body may include a sleeve portion and a flange portion extending outwardly from a perimeter of the sleeve portion. The at least one aperture may be established along the flange portion. The sleeve portion may have a sleeve passage dimensioned to at least partially receive a proximal end portion of the guide body.

In a further implementation, the trajectory guide may include an abutment along an outer periphery of the guide body. The secondary guide may be translatable along the passage axis to engage the abutment such that relative movement between the secondary guide and guide body may be limited relative to the passage axis.

In a further implementation, the trajectory guide may include a first interface feature along the guide body. The secondary guide may include a second interface feature along the sleeve portion. The first interface feature may be dimensioned to engage with the second interface feature to limit relative rotation between the guide body and the secondary guide.

In a further implementation, the first interface feature may be a protrusion extending outwardly from the outer periphery of the guide body. The second interface feature may include at least one groove along the sleeve passage of the sleeve portion. The protrusion may be insertable in the at least one groove to limit relative rotation between the guide body and the secondary guide.

In a further implementation, the at least one groove may include an array of grooves distributed along the sleeve passage of the sleeve portion. The protrusion may be insertable within a selected one of the grooves to set a circumferential position of the at least one aperture relative to the passage axis.

A system for planning an orthopaedic procedure according to an implementation of the present disclosure includes, inter alia, a computing device including a processor coupled to a memory. The processor may be configured to execute a planning environment including a display module, a spatial module and a comparison module. The memory may be configured to store a plurality of bone models including a first bone model and a second bone model. The display module may be configured to display the first bone model and the second bone model in a graphical user interface. The spatial module may be configured to establish a first resection surface of the first bone model according to a first reference plane. The spatial module may be configured to establish a second resection surface of the second bone model along a second reference plane. The spatial module may be configured to position the first resection surface in contact with the second resection surface along a contact region. The comparison module may be configured to determine a contact area ratio. The contact area ratio may be defined as a first area of the first resection surface along the contact region divided by a second area of the second resection surface. The comparison module may be configured to generate a first indicator in response to one or more predetermined criteria being met, the one or more predetermined criteria including the contact area ratio meeting a first predefined threshold.

In a further implementation, the first area may be less than the second area. The first predefined threshold may be greater than or equal to 0.4.

In a further implementation, the comparison module may be configured to determine a contact to resection ratio. The contact to resection ratio may be defined as the first area of the first resection surface along the contact region divided by the first area. The one or more predetermined criteria may include the contact to resection ratio being greater than or equal to 0.75.

In a further implementation, the comparison module may be configured to cause the display model to display the first indicator in the graphical user interface in response to the one or more predetermined criteria being met.

In a further implementation, the comparison module may be configured to cause the display model to display a value of the contact area ratio in the graphical user interface.

In a further implementation, the first bone model may be associated with a talus. The second bone model may be associated with a tibia.

In a further implementation, the spatial module may be configured to cause relative movement between the first resection surface and the second resection surface along the contact region in response to user interaction. The comparison module may be configured to update a value of the contact area ratio in response to the relative movement.

In a further implementation, the spatial module may be configured to set a position of the first reference plane with respect to the first bone model in response to user interaction. The spatial module may be configured to set a position of the second reference plane with respect to the second bone model in response to user interaction.

In a further implementation, the display module may be configured to display in a first display window of the graphical user interface the first and second bone models relative to a first image plane. The display module may be configured to set the first image plane to be parallel to the first and second reference planes such that the contact region is displayed along the first image plane in the first display window.

In a further implementation, the display module may be configured to display a visual contrast between the contact region and a remainder of the first and second resection surfaces that excludes the contact region.

In a further implementation, the comparison module may be configured to determine a set of values of the contact area ratio that may be associated with different positions of the first bone model relative to the second bone model along the contact region. Values in the set of values of the contact area ratio may correspond to respective directions from a contact axis intersecting the contact region. The display module may be configured to display a first directional indicator extending in a first direction relative to the contact axis. The first direction may be associated with a maximum value of the set of values of the contact area ratio.

In a further implementation, the spatial module may be configured to establish a first outer perimeter and a first inner perimeter of the first bone model along the first reference plane. The first inner and outer perimeters may be associated with respective first inner and outer profiles of a cortical wall associated with the first bone model. The first inner perimeter may be associated with a first cancellous area of the first bone model. The first cancellous area may correspond to an area along the first reference plane surrounded by the first inner perimeter. The spatial module may be configured to establish a second outer perimeter and a second inner perimeter of the second bone model along the second reference plane. The second inner and outer perimeters may be associated with respective second inner and outer profiles of a cortical wall associated with the second bone model.

The second inner perimeter may be associated with a second cancellous area of the second bone model. The second cancellous area may correspond to an area along the second reference plane surrounded by the second inner perimeter. The comparison module may be configured to determine a cancellous coverage ratio. The cancellous coverage ratio may be defined as an area of overlap between the first and second cancellous areas divided by the first cancellous area. The comparison module may be configured to generate a second indicator in response to the cancellous coverage ratio meeting a second predefined threshold.

In a further implementation, the second predefined threshold may be equal to or greater than 0.75.

In a further implementation, the spatial module may be configured to determine a first cortical area and a second cortical area. The first cortical area may correspond to an area between the first inner and outer perimeters along the contact region. The second cortical area may correspond to an area between the second inner and outer perimeters along the contact region. The comparison module may be configured to determine a cortical coverage area. The cortical coverage ratio may be defined as an area of overlap between the first and second cortical areas divided by the first cortical area. The comparison module may be configured to generate a third indicator in response to the cortical coverage ratio meeting a third predefined threshold.

In a further implementation, the third predefined threshold may be equal to or greater than 0.03.

In a further implementation, one of the first and second bone models may be associated with a talus. Another one of the first and second bone models may be associated with a tibia.

In a further implementation, the first bone model may be associated with a talus. The second bone model may be associated with a tibia.

In a further implementation, the spatial module may be configured to establish a first outer perimeter and a first inner perimeter of the first bone model along the first reference plane. The first inner and outer perimeters may be associated with respective first inner and outer profiles of a cortical wall associated with the first bone model. The spatial module may be configured to determine a first cortical area and a first boundary area. The first cortical area may correspond to an area between the first inner and outer perimeters along the contact region. The first boundary area may correspond to the area between the first inner and outer perimeters. The comparison module may be configured to determine a cortical support ratio. The cortical support ratio may be defined as the first cortical area divided by the first boundary area. The one or more predetermined criteria may include the cortical support ratio being greater than or equal to 0.50.

In a further implementation, the spatial module may be configured to establish a second outer perimeter and a second inner perimeter of the second bone model along the second reference plane. The second inner and outer perimeters may be associated with respective second inner and outer profiles of a cortical wall associated with the second bone model. The spatial module may be configured to determine a second boundary area. The second boundary area may correspond to the area between the second inner and outer perimeters. The spatial module may be configured to establish at least four localized support regions along the first boundary area. The comparison module may be configured to generate a support indicator in response to a predefined support threshold being met. The predefined support threshold may be defined as a quantity of three localized support regions in which contact between the first and second boundary areas is established.

In a further implementation, the spatial module may be configured to determine a first distance along a longitudinal axis between a first end and a second end of the second bone model. The spatial module may be configured to determine a second distance along the longitudinal axis between the second reference plane and the second end of the second bone model. The comparison module may be configured to determine a length ratio in response to setting a position of the second reference plane. The length ratio may be defined as a ratio of the second distance divided by the first distance. The comparison module may be configured to generate a fourth indicator in response to the length ratio being less than a predefined length threshold.

In a further implementation, the predefined length threshold may be less than or equal to 0.01.

In a further implementation, the spatial module may be configured to determine a first trajectory associated with a first guide pin and a second trajectory associated with a second guide pin in response to the one or more predetermined criteria being met. The first and second trajectories may be associated with respective first and second positions along one of the first and second bone models relative to the contact region.

In a further implementation, the comparison module may be configured to generate one or more settings associated with a trajectory assembly based on the first and second trajectories.

In a further implementation, the memory may be configured to store at least one implant model. The spatial module may be configured to position the at least one implant model relative to the first and second bone models in response to user interaction. The spatial module may be configured to determine one or more overlapping volumes between the at least one implant model and the first and second bone models. The display module may be configured to display the at least one implant model in the graphical user interface. The display module may be configured to display a visual contrast between the one or more overlapping volumes and a remainder of the volumes of the first and second bone models that excludes the one or more overlapping volumes.

In a further implementation, the spatial module may be configured to generate an iteration of the first and second bone models that excludes the one or more overlapping volumes. The display module may be configured to display the at least one implant model positioned relative to the iteration of the first and second bone models.

A method of performing an orthopaedic procedure according to an implementation of the present disclosure includes, inter alia, selecting a first bone model and a second bone model from a plurality of bone models. The method may include displaying the first and second bone models in a graphical user interface such that a first articular surface of the first bone model opposes a second articular surface of the second bone model. The method may include setting a first reference plane in the graphical user interface to establish a first resection surface of the first bone model. The method may include setting a second reference plane in the graphical user interface to establish a second resection surface of the second bone model. The method may include generating a first iteration of the first and second bone models that may exclude respective volumes of the first and second bone models between the first and second reference planes and the first and second articular surfaces of the first and second bone models. The method may include positioning the first resection surface in contact with the second resection surface to establish a contact region. The method may include displaying the first iteration of the first and second bone models along the contact region in the graphical user interface. The method may include determining a contact area ratio. The contact area ratio may be defined as a first area of the first resection surface along the contact region divided by a second area of the second resection surface. The method may include displaying at least one indicator in the graphical user interface associated with the contact area ratio in response to meeting one or more predetermined criteria.

In a further implementation, the first bone model may be associated with a talus. The second bone model may be associated with a tibia.

In a further implementation, the at least one indicator may include a value of the contact area ratio.

In a further implementation, the step of displaying the at least one indicator may occur in response to meeting one or more predetermined criteria. The one or more predetermined criteria may include the contact area ratio meeting a first predefined threshold.

In a further implementation, the first area may be less than the second area. The first predefined threshold may be greater than or equal to 0.4.

In a further implementation, the step of displaying the first iteration of the first and second bone models along the contact region may include displaying a visual contrast between the contact region and a remainder of the first and second resection surfaces that excludes the contact region.

In a further implementation, the step of determining the contact area ratio may include determining a set of values of the contact area ratio associated with different positions of the first resection surface relative to the second resection surface along the contact region. Values in the set of values of the contact area ratio may correspond to respective directions along the contact region. The at least one indicator may include a first directional indicator associated with a maximum value of the set of values of the contact area ratio. The step of displaying the at least one indicator may include displaying the first directional indicator relative to the contact region.

In a further implementation, the method includes moving the first bone model in a second direction relative to the first bone model along the contact region. The second direction may be substantially aligned with a first direction corresponding to the first directional indicator.

In a further implementation, the method includes determining a first cortical area along the first resection surface. The first cortical area may be associated with cortical bone. The method may include determining a second cortical area along the second resection surface. The second cortical area may be associated with cortical bone. The first cortical area may be less than the second cortical area. The method may include determining a cortical coverage ratio. The cortical coverage ratio may be defined as an area of overlap between the first and second cortical areas along the contact region divided by the first cortical area. The one or more predetermined criteria may include the cortical coverage ratio meeting a second predefined threshold.

In a further implementation, the second predefined threshold may be greater than or equal to 0.03.

In a further implementation, the first bone model may be associated with a talus. The second bone model may be associated with a tibia.

In a further implementation, the method includes determining a first cancellous area along the first resection surface. The first cancellous area may be associated with cancellous bone. The method may include determining a second cancellous area along the second resection surface. The second cancellous area may be associated with cancellous bone. The first cancellous area may be less than the second cancellous area. The method may include determining a cancellous coverage ratio. The cancellous coverage ratio may be defined as an area of overlap between the first and second cancellous areas along the contact region divided by the first cancellous area. The one or more predetermined criteria may include the cancellous coverage ratio meeting a third predefined threshold.

In a further implementation, the third predefined threshold may be greater than or equal to 0.75.

In a further implementation, the first bone model may be associated with a talus. The second bone model may be associated with a tibia.

In a further implementation, the second bone model may be associated with a long bone. The method may include determining a first distance along a longitudinal axis between a first end and a second end of the second bone model. The method may include determining a second distance along the longitudinal axis between the second reference plane and the second end of the second bone model. The method may include determining a length ratio. The length ratio may be defined as a ratio of the second distance divided by the first distance. the step of displaying the at least one indicator may occur in response to meeting one or more predetermined criteria. The one or more predetermined criteria may include the length ratio meeting a predefined length threshold.

In a further implementation, the predefined length threshold may be less than or equal to 0.01.

In a further implementation, the method includes determining a first trajectory associated with a first guide pin and a second trajectory associated with a second guide pin in response to the contact area ratio meeting a first predefined threshold. The first and second trajectories may be associated with respective first and second positions along one of the first and second bone models relative to the contact region. The method may include generating one or more settings associated with a trajectory assembly based on the first and second trajectories.

In a further implementation, the trajectory assembly may include a trajectory guide and a secondary guide coupled to the trajectory guide. The method may include configuring the trajectory guide according to the one or more settings. the method may include moving the trajectory guide into abutment with a bone. The bone may be associated with a respective one of the first and second bone models. the method may include positioning the first guide pin into the bone with the trajectory guide according to the first trajectory. The method may include positioning the second guide pin into the bone with the trajectory guide according to the second trajectory.

In a further implementation, the trajectory guide may include a guide body and at least one arm member coupled to the guide body. The guide body may include a guide passage that at least partially receives the first guide pin along a passage axis to establish the first trajectory. The step of configuring the trajectory guide may include moving the at least one arm member from a first position to a second position relative to the guide body. The secondary guide may include a main body having at least one aperture that at least partially receives the second guide pin along an aperture axis to establish the second trajectory. The secondary guide may be coupled to the guide body such that the aperture axis may be offset from the passage axis.

In a further implementation, the secondary guide may be moveable relative to a longitudinal axis of the trajectory guide. The method may include configuring the secondary guide according to the one or more settings, which may include setting a position of the secondary guide relative to the longitudinal axis to establish the second trajectory relative to the first trajectory.

In a further implementation, the method includes positioning a first cutting guide along the first and second guide pins. The first cutting guide may establish a resection plane. The resection plane may be associated with one of the first and second reference planes. The method may include resecting a portion of the bone along the resection plane to establish a resection surface of the bone.

In a further implementation, the bone may be a first bone associated with the first bone model. The first bone may be opposed to a second bone associated with the second bone model. The method may include determining a third trajectory associated with a third guide pin and a fourth trajectory associated with a fourth guide pin in response to the contact area ratio meeting the first predefined threshold. The third and fourth trajectories may be associated with respective third and fourth positions along the second bone model relative to the contact region. The method may include generating one or more settings associated with the trajectory assembly based on the third and fourth trajectories. The method may include moving the trajectory guide into abutment with the second bone. The method may include positioning the third guide pin into the second bone with the trajectory guide according to the third trajectory. The method may include positioning the fourth guide pin into the second bone with the trajectory guide according to the fourth trajectory. The method may include resecting a portion of the second bone associated according to the second reference plane to establish a resection surface of the second bone.

In a further implementation, the method includes moving resection surfaces of the first and second bones into abutment. The method may include positioning an implant along the first and second bones subsequent to the step of moving the resection surfaces of the first and second bones into abutment.

In a further implementation, the method includes selecting an implant model from a plurality of implant models. The method may include positioning the implant model relative to the first and second bone models subsequent to establishing the contact region. The method may include determining one or more overlapping volumes between the selected implant model and the first and second bone models. The method may include displaying the selected implant model in the graphical user interface, which may include displaying a visual contrast between the one or more overlapping volumes and a remainder of the volumes of the first and second bone models that excludes the one or more overlapping volumes.

In a further implementation, the method includes generating a second iteration of the first and second bone models that excludes the one or more overlapping volumes. The method may include repeating the step of determining the one or more overlapping volumes for the second iteration of the first and second bone models. The method may include repeating the step of displaying the selected implant model for the second iteration of the first and second bone models.

In a further implementation, the first bone may be a talus. The second bone may be a tibia.

A method of performing an orthopaedic procedure according to an implementation of the present disclosure includes, inter alia, configuring a trajectory guide. The trajectory guide may include a guide body and at least one arm member coupled to the guide body. The guide body may include a guide passage extending along a passage axis. The method may include moving the at least one arm member from a first position to a second position relative to the guide body to establish a first trajectory along the passage axis. The method may include configuring a secondary guide. The secondary guide may include a main body having at least one aperture extending along an aperture axis. The method may include coupling the secondary guide to the guide body to establish a second trajectory along the aperture axis. The aperture axis may be offset from the passage axis. The method may include moving the trajectory guide into abutment with bone. The method may include positioning a first guide pin through the guide passage and then into the bone according to the first trajectory. The method may include positioning a second guide pin through the at least one aperture and then into the bone according to the second trajectory.

In a further implementation, the step of configuring the secondary guide includes moving the main body of the secondary guide relative to a longitudinal axis of the trajectory guide such that the at least one aperture moves from a first circumferential position to a second circumferential position relative to the longitudinal axis.

FIG. 1 illustrates an exemplary planning system 20 that may be utilized for planning surgical procedures. The system 20 may be used for planning orthopaedic procedures, including pre-operatively, intra-operatively and/or post-operatively to create, edit, execute and/or review surgical plans.

The system 20 may include a host computer 21 and one or more client computers 22. The host computer 21 may be configured to execute one or more software programs. In some implementations, the host computer 21 is more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network, for example.

The host computer 21 and each client computer 22 may include one or more of a computer processor, memory, storage means, network device and input and/or output devices and/or interfaces. The input devices may include a keyboard, mouse, etc. The output device may include a monitor, speakers, printers, etc. The memory may, for example, include UVPROM, EEPROM, FLASH, RAM, ROM, DVD, CD, a hard drive, or other computer readable medium which may store data and/or other information relating to the planning techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. The client computers 22 may be configured to execute one or more software programs, such as a various surgical tools. The planning package may be configured to communicate with the host computer 21 either over the network 23 or directly through the direct client interface 24. In another implementation, the client computers 22 are configured to communicate with each other directly via a peer-to-peer interface 25.

Each client computer 22 may be operable to access and locally and/or remotely execute a planning environment 26. The planning environment 26 may be a standalone software package or may be incorporated into another surgical tool. The planning environment 26 may provide a display or visualization of one or more bone models and related images and one or more implant models via one or more graphical user interfaces (GUI). Each bone model, implant model, and related images and other information may be stored in one or more files or records according to a specified data structure.

The system 20 may include at least one storage system 27, which may be operable to store or otherwise provide data to other computing devices. The storage system 27 may be a storage area network device (SAN) configured to communicate with the host computer 21 and/or the client computers 22 over the network 23, for example. In implementations, the storage system 27 may be incorporated within or directly coupled to the host computer 21 and/or client computers 22. The storage system 27 may be configured to store one or more of computer software instructions, data, database files, configuration information, etc.

In some implementations, the system 20 is a client-server architecture configured to execute computer software on the host computer 21, which is accessible by the client computers 22 using either a thin client application or a web browser executing on the client computers 22. The host computer 21 may load the computer software instructions from local storage, or from the storage system 27, into memory and may execute the computer software using the one or more computer processors.

The system 20 may include one or more databases 28. The databases 28 may be stored at a central location, such as the storage system 27. In another implementation, one or more databases 28 may be stored at the host computer 21 and/or may be a distributed database provided by one or more of the client computers 22. Each database 28 may be a relational database configured to associate one or more bone models 29 and one or more implant models 30 to each other and/or a surgical plan 31. Each surgical plan 31 may be associated with a respective patient. Each bone model 29, implant model 30 and surgical plan 31 may be assigned a unique identifier or database entry. The database 28 may be configured to store data corresponding to the bone models 29, implant models 30 and surgical plans 31 in one or more database records or entries, and/or may be configured to link or otherwise associate one or more files corresponding to each respective bone model 29, implant model 30 and surgical plan 31. Bone models 29 stored in the database(s) 28 may correspond to respective patient anatomies from prior surgical cases, and may be arranged into one or more predefined categories such as sex, age, ethnicity, defect category, procedure type, etc.

Each bone model 29 may include information obtained from one or more medical devices or tools, such as a computerized tomography (CT), magnetic resonance imaging (MRI) machine and/or X-ray machine, that obtains one or more images of a patient. The bone model 29 may include one or more digital images and/or coordinate information relating to an anatomy of the patient obtained or derived from the medical device(s). Each implant model 30 may include coordinate information associated with a predefined design. The planning environment 26 may incorporate and/or interface with one or more modeling packages, such as a computer aided design (CAD) package, to render the models 29, 30 as two-dimensional (2D) and/or three-dimensional (3D) volumes or constructs.

The predefined design may correspond to one or more components. The implant models 30 may correspond to implants and components of various shapes and sizes. Each implant may include one or more components that may be situated at a surgical site including screws, anchors and/or grafts. Each implant model 30 may correspond to a single component or may include two or more components that may be configured to establish an assembly. Each bone model 29 and implant model 30 may correspond to 2D and/or 3D geometry, and may be utilized to utilized to generate a wireframe, mesh and/or solid construct in a display.

Each surgical plan 31 may be associated with one or more of the bone models 29 and implant models 30. The surgical plan 31 may include one or more revisions to bone model 29 and information relating to a position of an implant model 30 relative to the original and/or revised bone model 29. The surgical plan 31 may include coordinate information relating to the revised bone model and a relative position of the implant model 30 in predefined data structure(s). Revisions to each bone model 29 and surgical plan 31 may be stored in the database 28 automatically and/or in response to user interaction with the system 20.

One or more surgeons and other users may be provided with a planning environment 26 via the client computers 22 and may simultaneously access each bone model 29, implant model 30 and surgical plan 31 stored in the database(s) 28. Each user may interact with the planning environment 26 to create, view and/or modify various aspects of the surgical plan 31. Each client computer 22 may be configured to store local instances of the bone models 29, implant models 30 and/or surgical plans 31, which may be synchronized in real-time or periodically with the database(s) 28. The planning environment 26 may be a standalone software package executed on a client computer 22 or may be provided as one or more services executed on the host computer 21, for example.

Figure 2:
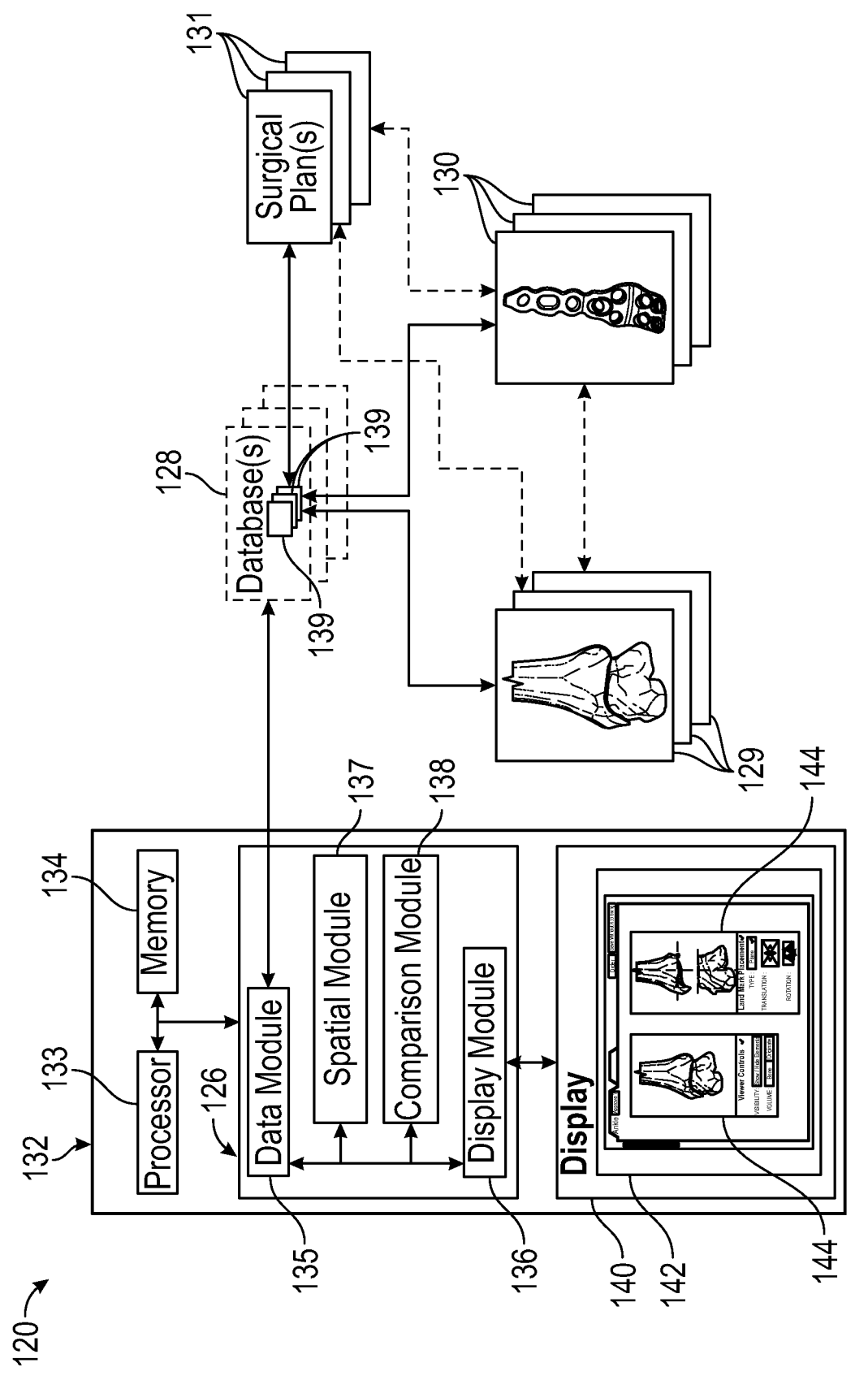
FIG. 2 illustrates another exemplary planning system including a user interface.

FIG. 2 illustrates an exemplary fusion planning system 120 for planning a surgical procedure. The system 120 may be utilized to plan and implement various orthopaedic and other surgical procedures, such as an arthroplasty to repair a joint. The system 120 may be utilized in planning a resection of one or more bones that may be positioned for fusion. The system 120 may be utilized in planning placement of an implant, which may be utilized for fusion of resected bones such as a tibia and talus in an ankle repair. Although the planning systems and methods disclosed herein primarily refer to repair of an ankle, it should be understood that the planning system 120 may be utilized in the repair of other locations of the patient and other surgical procedures including repair of other joints such as a shoulder, wrist, hand, hip or knee, and including repair of fractures.

The system 120 may include a computing device 132 including at least one processor 133 coupled to memory 134. The computing device 132 can include any of the computing devices disclosed herein, including the host computer 21 and/or client computer 22 of FIG. 1. The processor 133 may be configured to execute a planning environment 126 for creating, editing, executing and/or reviewing one or more surgical (e.g., pre-operative) plans 131 during pre-operative, intra-operative and/or post-operative phases of a surgery.

The planning environment 126 may include at least a data module 135, a display module 136, a spatial module 137 and a comparison module 138. Although four modules are shown, it should be understood that fewer or more than four modules may be utilized and/or one or more of the modules may be combined to provide the disclosed functionality.

The data module 135 may be configured to access, retrieve and/or store data and other information in the database(s) 128 corresponding to one or more bone model(s) 129, implant model(s) 130 and/or surgical plan(s) 131. The data and other information may be stored in one or more databases 128 as one or more records or entries 139. In some implementations, the data and other information may be stored in one or more files that are accessible by referencing one or more objects or memory locations references by the records or entries 139.

The memory 134 may be configured to access, load, edit and/or store instances of one or more bone models 129, implant models 130 and/or surgical plans 131 in response to one or more commands from the data module 135. The data module 135 may be configured to cause the memory 134 to store a local instance of the bone model(s) 129, implant model(s) 130 and/or surgical plan(s) 131 which may be synchronized with records 139 in the database(s) 128.

The display module 136 may be configured to display data and other information relating to one or more surgical plans 131 in at least one graphical user interface (GUI) 142. The computing device 132 may be coupled to a display device 140. The display module 136 may be configured to cause the display device 140 to display information in the user interface 142. A surgeon or other user may interact with the user interface 142 via the planning environment 126 to create, edit, execute and/or review one or more surgical plans 131.

Figure 3:
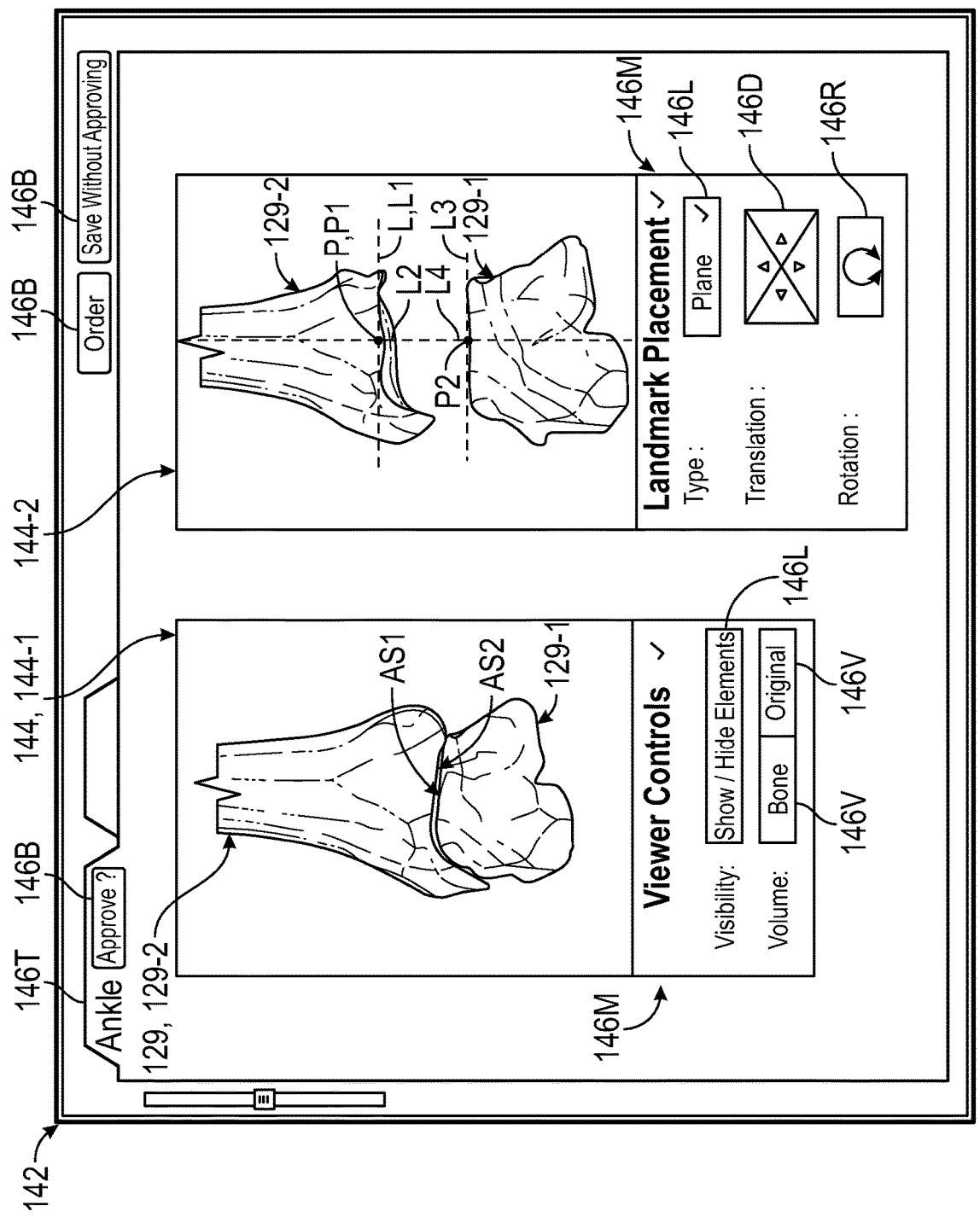
FIG. 3 illustrates the user interface of FIG. 2 including display windows depicting adjacent bone models.

Referring to FIG. 3, with continuing reference to FIG. 2, the user interface 142 may include one or more display windows 144 and one or more objects 146. The objects 146 may include graphics such as menus, tabs and buttons accessible by user interaction, such as tabs 146T, buttons 146B, 146V, drop-down lists 146L, menus 146M, entry fields 146E (FIGS. 6 and 8), directional indicators 146D, 146R and graphics 146G (see, e.g., FIGS. 5-6). Geometric objects including selected bone model(s) 129 and implant model(s) 130 (see, e.g., FIG. 12) and other information relating to the surgical plan 131 may be displayed in one or more of the display windows 144.

The implant model 130 may include one or more components. Exemplary implants may include bone plates configured to interconnect adjacent bones (see, e.g., FIG. 12) or bone fragments, base plates coupled to an articulation member, etc. The articulation member may have an articular surface dimensioned to mate with an articular surface of an opposed bone or implant.

The display module 136 may be configured to display one or more selected bone models 129 and/or one or more selected implant models 130 (see, e.g., FIGS. 9 and 12) in the display windows 144. The display module 136 may be configured such that the selected bone model 129 and/or selected implant model 130 may be selectively displayed and hidden (e.g., toggled) in one or more of the display windows 144 in response to user interaction with the user interface 142, which may provide the surgeon with enhanced flexibility in reviewing aspects of the surgical plan 131.

The data module 135 may be configured to access a first bone model 129-1 and a second bone model 129-1 from the database 128, which may occur automatically or in response to user interaction with the user interface 142. The data module 135 may be configured to store an instance of the first bone model 129-1 and second bone model 129-1 in the memory 134. The first bone model 129-1 and second bone model 129-2 may be associated with a joint. For example, one of the bone models 129 may be associated with a long bone such as a tibia, and another one of the bone models 129 may be associated with an adjacent bone such as a tibia that cooperate to establish an ankle or another joint of a patient. In the implementation of FIG. 3, the second bone model 129-2 may be associated with a tibia, and the first bone model 129-1 may be associated with a talus. The display module 136 may be configured to display the first bone model 129-1 and second bone model 129-2 in at least one of the display windows 144 of the user interface 142.

The display windows 144 may include first and second display windows 144-1, 144-2. Although a particular number of display windows 144 are illustrated, it should be understood that the user interface 142 may be configured with any number of display windows 144 in accordance with the teachings disclosed herein. The display windows 144-1, 144-2 may be configured to display a two-dimensional (2D) and/or three-dimensional (3D) representation of the selected bone models 129.

The first display window 144-1 may be configured to display the first bone model 129-1 and second bone model 129-2 relative to each other. The spatial module 137 may be configured to position the bone models 129-1, 129-2 into contact with each other at a specified or defined position and orientation, which may be according to user interaction with the window 144-1, menu 146M, and/or other objects 146 of the user interface 142.

The surgeon or assistant may interact with the display window 144-1 or another portion of the user interface 142 to move the selected bone model 129 and/or selected implant model 130 in 2D space (e.g., up, down, left, right) and/or 3D space (e.g., rotation, tilt, zoom, etc.), which may occur in response to interaction with the directional indicators 146D, 146R.

The second display window 144-2 may be configured to display the first bone model 129-1 and second bone model 129-2 in spaced relationship relative to each other. The surgeon or assistant may interact with the second display window 144-2 or another portion of the user interface 142 to associate one or more landmarks L with the selected bone models 129. The landmarks L may include one or more points P along the anatomy (e.g., P1-P2) and one or more planes (e.g., L1-L4). Exemplary landmarks include a tibial axis, sagittal plane, coronal plane and transverse plane. In implementations, the spatial module 137 may be configured to determine one or more landmarks L based on evaluating a profile of the selected bone model 129. The profile can be compared to one or more profiles of representative bones in the database 128.

Figure 4:
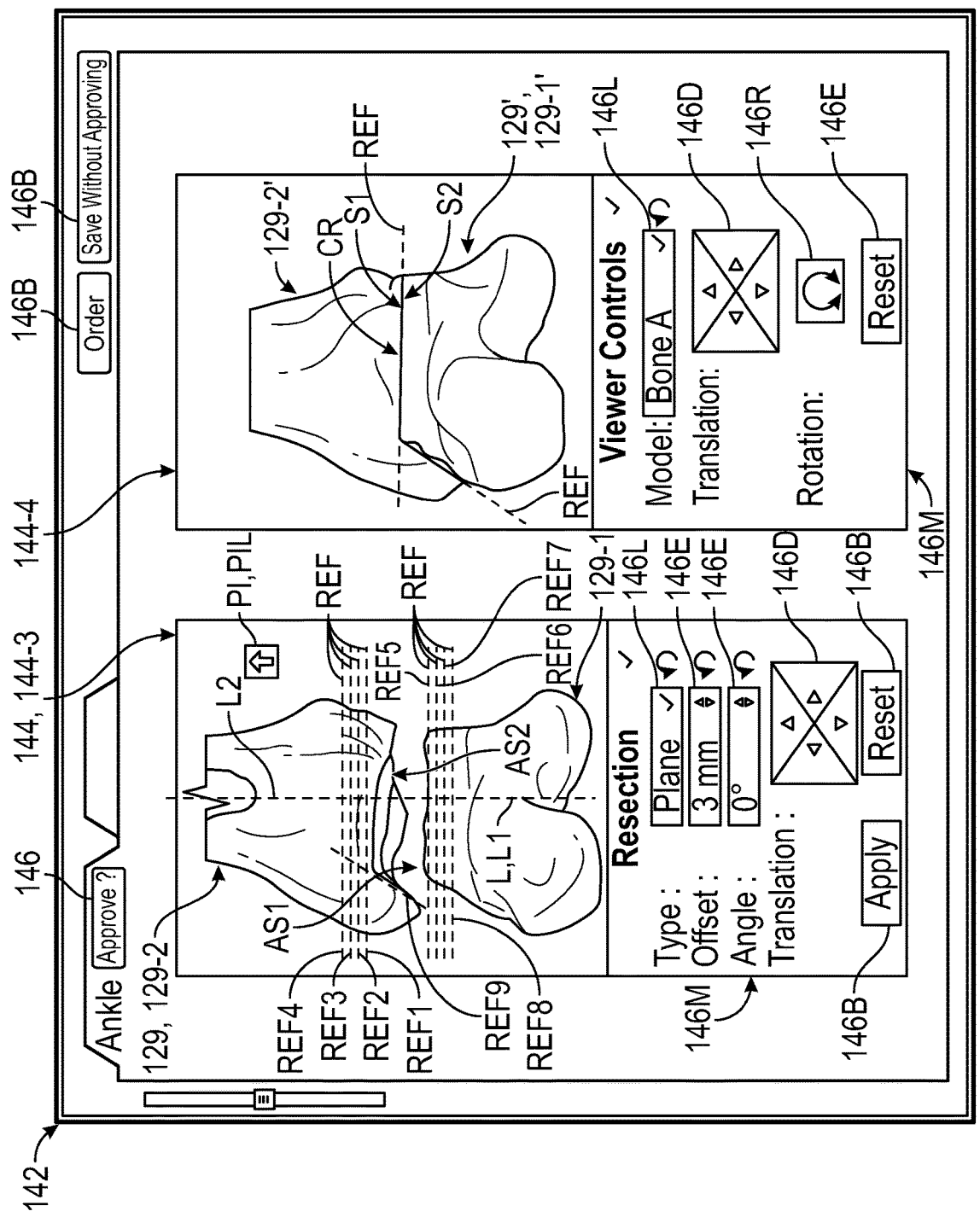
FIG. 4 illustrates the user interface of FIG. 2 including display windows depicting resection planes and a contact region between bone models.

Referring to FIG. 4, with continuing reference to FIGS. 2-3, the user interface 142 may include third and fourth display windows 144-3, 144-4. The surgeon or assistant may interact with the display windows 144-3, 144-4 or another portion of the user interface 142 to specify one or more aspects of, or modifications to, the surgical plan 131. The modifications may include one or more resection planes REF associated with a respective one of the bone models 129. The third display window 144-3 may be configured to display each reference plane REF relative to the respective bone model 129. The bone models 129-1, 129-2 may include respective articular surfaces AS1, AS2 associated with a joint. Each reference plane REF may be associated with a respective depth inward from the respective articular surface AS1/AS2 of the bone model 129 (e.g., 1 mm, 2 mm, 3 mm, 4 mm etc.). The reference planes REF may be substantially perpendicular to a landmark L of the respective bone model 129 (e.g., landmarks L1, L2 and reference planes REF1-REF8). For the purposes of this disclosure, the terms "substantially," "about" and "approximately" mean±5 percent of the stated value or relationship unless otherwise indicated. One or more of the reference planes REF may be transverse to another reference plane REF (e.g., reference plane REF9 relative to reference planes REF1-REF4).

The spatial module 137 may be configured to set a position of a first reference plane REF with respect to the first bone model 129-1 in response to user interaction with the user interface 142. The spatial module 137 may be configured to set a position of a second reference plane REF with respect to the second bone model 129-2 in response to user interaction with the user interface 142. For example, the surgeon or assistant may adjust a position (e.g., depth) and/or angle of a selected reference plane REF in response to user interaction with the user interface 142. The surgeon or assistant may interact with one of the entry fields 146E to specify an offset or depth associated with the reference plane REF.

The spatial module 137 may be configured to generate a first iteration of respective first and second (e.g., resected) bone models 129-1', 129-2'. The bone models 129-1', 129-2' may exclude respective volumes of the bone models 129-1, 129-2 between the respective reference planes REF and articular surfaces AS1, AS2 of the bone models 129-1, 129-2, as illustrated in the fourth display window 144-4. The bone models 129-1', 129-2' may be separate models or may be stored as one or more revisions to the respective bone models 129-1, 129-2.

The spatial module 137 may be configured to establish a first resection (e.g., contact) surface S1 of the first bone model 129-1' according to a first reference plane REF (e.g., REF1-REF4) and may be configured to establish a second resection (e.g., contact) surface S2 of the second bone model 129-2' along a second reference plane REF (e.g., REF5-REF8), as illustrated in the fourth display window 144-4. The first and second resection surfaces S1, S2 of the bone models 129-1', 129-2' may be opposed relative to each other and may be positioned apart and/or in abutment in the display windows 144. The fourth display window 144-4 may be dynamically linked to the third display window 144-3 such that selection and/or adjustments to the respective reference plane REF associated with the third display window 144-3 cause a position of the respective resection surface S1/S2 to change in the fourth display window 144-4. The display module 136 may be configured to display the iteration of the bone models 129-1', 129-2' in the fourth display window 144-4 in response to adjusting or otherwise setting the resection planes REF. The surgeon or assistant may interact with the user interface 142 to obtain a visualization of resection depths, which may be adjusted prior to approval of the surgical plan 131.

The spatial module 137 may be configured to position the first resection surface S1 associated with the first bone model 129-1' in contact with the second resection surface S1 of associated with the second bone model 129-2' along a contact region CR. The contact region CR may be a region of bone-to-bone contact between the resection surfaces S1, S2. The contact region CR may be continuous or may be discontinuous including two or more localized regions of contact. The localized regions of contact may be separated by a space due to surface depression(s) or other contouring along the resection surfaces S1, S2.

The surgeon or assistant may interact with the directional indicators 146D, 146R or another portion of the user interface 142 to adjust or otherwise setting a relative position between the bone models 129-1', 129-2' along the contact region CR. The surgeon or assistant may interact with the user interface 142 to evaluate aspects of the bone models 129-1', 129-2' relative to the contact region CR and associated reference planes REF.

Figure 5:
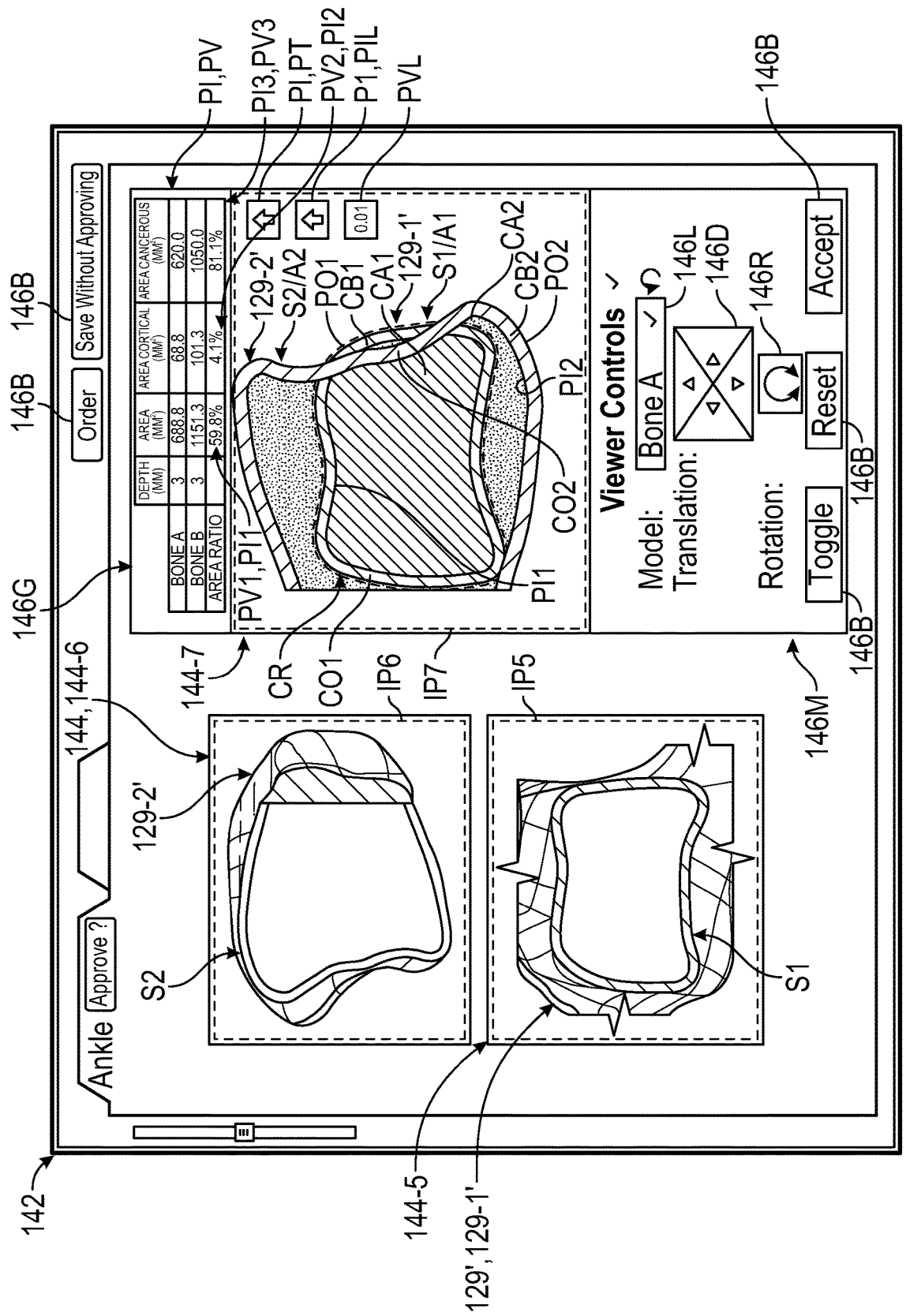
FIG. 5 illustrates the user interface of FIG. 2 including display windows depicting resection surfaces, a contact region between bone models and exemplary indicators.

Referring to FIG. 5, with continuing reference to FIGS. 2 and 4, the display windows 144 can include fifth, sixth and seventh display windows 144-5, 144-6, 144-7. The fifth display window 144-5 can be configured to display an isolated view of the iteration of the first bone model 129-1'. The sixth display window 144-6 can be configured to display an isolated view of the iteration of the second bone model 129-2'.

The fifth, sixth and seventh display windows 144-5, 144-6, 144-7 may be associated with respective fifth, sixth and seventh image (e.g., viewing) planes IP5, IP6, IP7 (shown in dashed lines for illustrative purposes). The fifth, sixth and/or seventh image planes IP5, IP6, IP7 may be substantially parallel to each other. The display module 136 may be configured to set the image planes IP5, IP6, IP7 to be substantially parallel to the specified or defined reference planes REF associated with the respective bone models 129-1', 129-2'. The display module 136 may be configured to display the resection surfaces S1, S2 and/or contact region CR substantially parallel to the image planes IP5, IP6, IP7 of the respective display windows 144-5, 144-6, 144-7 such that the resection surfaces S1, S2 and/or contact region CR are displayed along the image planes IP5, IP6, IP7 of the respective display windows 144-5, 144-6, 144-7. Utilizing the techniques disclosed herein, the resection surfaces S1, S2 may be presented substantially perpendicular to the user, which may assist the surgeon in evaluating the defined resection planes REF (FIG. 4) and determining whether to implement one or more revisions or adjustments to the resection planes REF and/or resected bone models 129-1', 129-2'.

Figure 6:
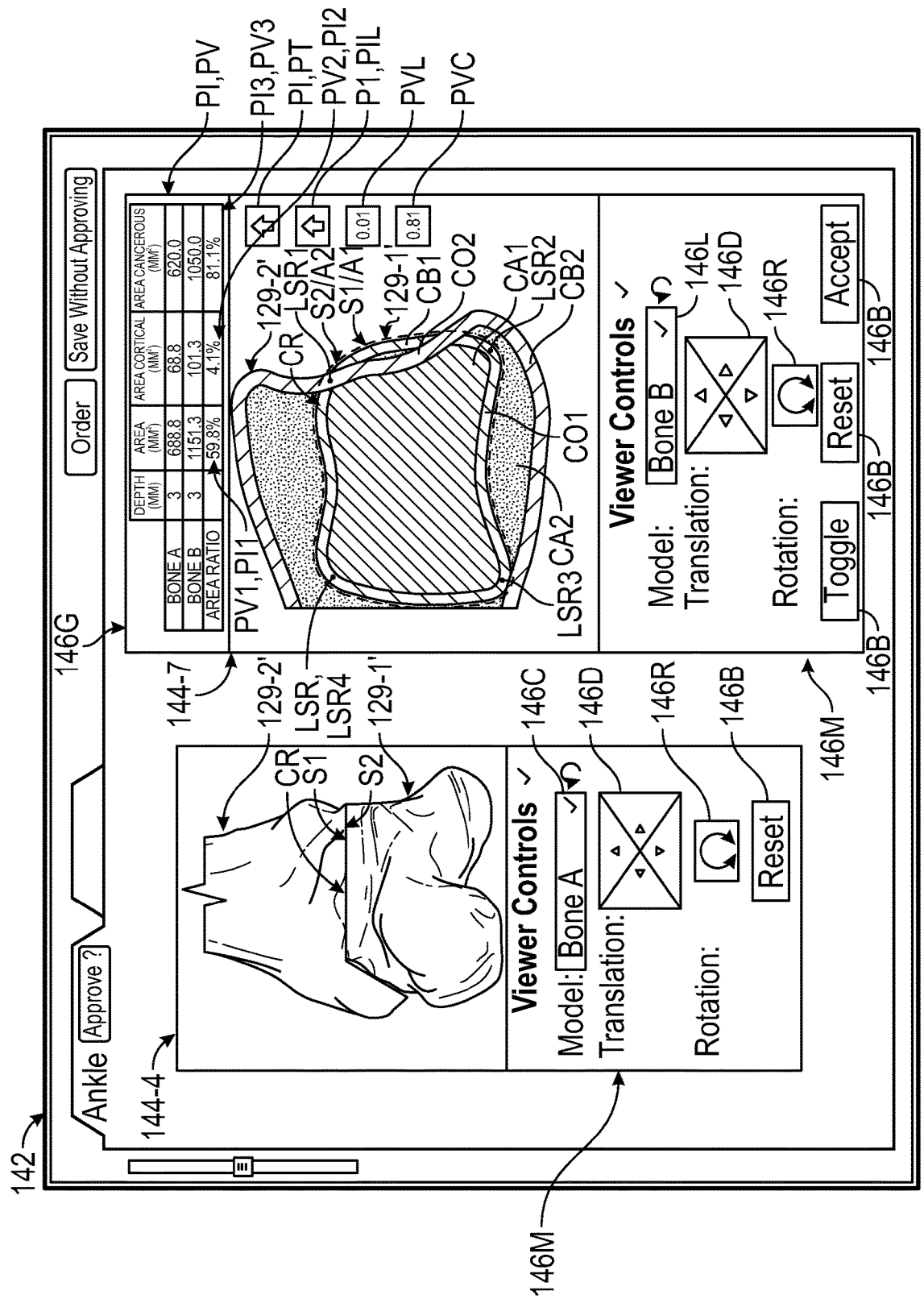
FIG. 6 illustrates the user interface of FIG. 2 including display windows depicting a contact region between bone models and exemplary indicators.

Referring to FIG. 6, with continuing reference to FIGS. 2 and 5, the user interface 142 may be configured to display an isolated view of the resection surfaces S1, S2 along the contact region CR in the seventh display window 144-7. The contact region CR is shown in dashed lines for illustrative purposes. The user interface 142 may be configured to display the fourth display window 144-4 adjacent to the seventh display window 144-7, which may be utilized by the surgeon or assistant to make one or more adjustments to the relative positioning of the bone models 129-1', 129-2' relative to the contact region CR, which may improve the ability of the surgeon or assistant to evaluate the contact region CR and selected resection planes REF (FIG. 4).

The spatial module 137 may be configured to determine one or more parameters associated with the contact region CR. The spatial module 137 may be configured to determine a first area A1 of the first resection surface S1 and a second area A2 of the second resection surface S2. The spatial module 137 may be configured to determine one or more localized regions of the areas A1, A2, such as first and second cortical areas CO1, CO2, first and second cortical boundary areas CB1, CB2 and/or first and second cancellous areas CA1, CA2 associated with the respective areas A1, A2. The cortical areas CO1, CO2 and cortical boundary areas CB1, CB2 may be associated with cortical bone. The cancellous areas CA1, CA2 may be associated with cancellous bone surrounded by a cortical wall of the cortical bone.

Various techniques may be utilized to determine the areas. The spatial module 137 may be configured to establish a first outer perimeter PO1 and a first inner perimeter PH of the first bone model 129-1' along the respective reference plane REF (FIG. 4), as illustrated in FIG. 5. The first inner and outer perimeters PI1, PO1 may be associated with respective first inner and outer profiles of a cortical wall associated with the first bone model 129-1'. The first inner perimeter PH may be associated with the first cancellous area CA1 of the first bone model 129-1'. The first cancellous area CA1 may correspond to an area along the reference plane REF surrounded by the first inner perimeter PH. The spatial module 137 may be configured to establish a second outer perimeter PO2 and a second inner perimeter PI2 of the second bone model 129-2' along the respective reference plane REF (FIG. 4), as illustrated in FIG. 5. The second inner and outer perimeters PI2, PO2 may be associated with respective second inner and outer profiles of a cortical wall associated with the second bone model 129-2'. The second inner perimeter PI2 may be associated with a second cancellous area CA2 of the second bone model 129-2'. The second cancellous area CA2 may correspond to an area along the respective reference plane REF surrounded by the second inner perimeter PI2. The first cortical area CO1 may correspond to an area between the first inner and outer perimeters PH, PO1 along the contact region CR. The first cortical boundary area CB1 may correspond to the area between the first inner and outer perimeters PI1, PO1, inclusive of the first cortical area CO1. The second cortical area CO2 may correspond to an area between the second inner and outer perimeters PI2, PO2 along the contact region CR. The second cortical boundary area CB2 may correspond to the area between the second inner and outer perimeters PI2, PO2, inclusive of the second cortical area CO2. Defining the areas A1, A2, CA1, CA2, CO1, CO2 with respect to the contact region CR can be utilized to omit portions of the resection surfaces S1, S2 that may not establish contact due to overhang, underhang and/or other misalignment between the bone models 129-1', 129-2'. Defining the cortical boundary areas CB1, CB2 may be utilized to account for portions of the resection surfaces S1, S2 that may not establish contact along the contact region CR.

Various techniques may be utilized to determine the perimeters PI1, PI2, PO1, PO2 and associated areas A1, A2, CA1, CA2, CB1, CB2, CO1, CO2, including edge detection techniques based on one or more image gradients. Other exemplary techniques may include positioning one or more points along the bone resection surfaces S1, S2 in response to user interaction with the user interface 142, which may be interconnected to establish a perimeter associated with the respective area. One of ordinary skill in the art would understand how to program the spatial module 137 with logic to determine the various parameters including the PI1, PI2, PO1, PO2 and associated areas A1, A2, CA1, CA2, CB1, CB2, CO1, CO2, including one or more CAD tools, libraries, etc.

The comparison module 138 may be configured to determine a contact (e.g., coverage) area ratio CAR associated with the contact region CR. The contact area ratio CAR may be defined as the first area A1 of the first resection surface S1 along the contact region CR divided by the second area A2 of the second resection surface S2. The first area A1 may be less than the second area A2. The following table illustrates exemplary contact area ratios CAR with respect to cut depth and surfaces areas of the first and second resection surfaces S1, S2, which may be associated with adjacent bones such as a talus and tibia.

| Cut Depth | Surface Area (mm²) | | | | | | | | |
|---|---|---|---|---|---|---|---|---|---|
| (mm) | 1 × 1 | 1 × 2 | 1 × 3 | 2 × 1 | 2 × 2 | 2 × 3 | 3 × 1 | 3 × 2 | 3 × 3 |
| Talus | 355.5 | 545.4 | 688.8 | 355.5 | 688.8 | 355.5 | 355.5 | 545.4 | 688.8 |
| Tibia | 1163.1 | 1163.1 | 1158.4 | 1158.4 | 1158.4 | 1151.3 | 1151.3 | 1151.3 | 1151.3 |
| Contact area ratio (CAR) | 0.306 | 0.469 | 0.592 | 0.307 | 0.471 | 0.595 | 0.309 | 0.474 | 0.598 |

The system 120 may be configured to determine a portion of the first area A1 of the first resection surface S1 that establishes the contact region CR. A contact to resection area ratio CRR may be defined as an area of the first resection surface S1 along the contact region CR divided by the first area A1 of the first resection surface S1. In implementations, the contact to resection area ratio CRR may be greater than or equal to 0.75, or more narrowly greater than or equal to 0.90, or more narrowly less than or equal to 1.0. The contact to resection area ratio CRR may be 1.0 such that an entirety of the first resection surface S1 contacts the second resection surface S2 to establish the contact region CR. The first area A1 may be less than the second area A2 such that a portion of the second resection surface S2 may not contact the first resection surface S1.

The system 120 may be configured to determine other aspects associated with the contact area ratio CAR, including particular bone types associated with the bone models 129-1', 129-2' such as cortical bone and cancellous bone. The comparison module 138 may be configured to determine a cancellous coverage ratio CCR. The cancellous coverage ratio CCR may be defined as an area of overlap between the first and second cancellous areas CA1, CA2 divided by the first cancellous area CAL The cancellous coverage ratio CCR may be utilized to indicate whether bones associated with the resection surfaces S1, S2 along the contact region CR are likely to achieve sufficient bone fusion, which may improve healing of the patient.

The comparison module 138 may be configured to determine a cortical coverage ratio COR. The cortical coverage ratio COR may be defined as an area of overlap between the first and second cortical areas CO1, CO2 divided by the first cortical area CO1. The cortical coverage ratio COR may be utilized to indicate whether bones associated with the resection surfaces S1, S2 along the contact region CR are likely to achieve sufficient support.

The system 120 may be configured to determine an amount of the first cortical boundary area CB1 and/or an amount of the second cortical boundary area CB2 that establishes the contact region CR. The surgeon may interact with the system 120 to evaluate whether or not the resected load bearing bone(s) may provide sufficient support to the adjacent resected bone. The second resection surface S2 of the second bone model 129-2 may sit on, or may otherwise be supported by, the first resection surface S1 of the first bone model 129-1 such that the first bone model 129-1 may be associated with the load bearing bone and such that the second bone model 129-2 may be associated with the supported bone, or vice versa, which may depend on the surgical procedure associated with the surgical plan 131.

A cortical support ratio CSR may be defined as the cortical area CO1/CO2 divided by the respective cortical boundary area CB1/CB2. In implementations, the cortical support ratio CSR may be greater than or equal to 0.50, more narrowly greater than or equal to 0.75, or even more narrowly greater than or equal to 0.90. The cortical support ratio CSR may be less than or equal to 1.0. The cortical support ratio CSR may be 1.0 such that an entirety of the cortical boundary area CB1/CB2 contacts the adjacent resection surface S2/S1 to establish the contact region CR and associated cortical area CO1/CO2. The cortical support ratio CSR disclosed herein may be utilized to establish an improved support or foundation to the opposing resection surface S2/S1. The cortical support ratio CSR may be utilized in combination with an implant to provide the improved support, including any of the implants disclosed herein. Improved support may be beneficial to patients having relatively smaller bones, lesser bone density, lesser bone quality, etc.

The comparison module 138 may be configured to cause the display module 136 to display value(s) of one or more parameters associated with the contact region CR in a graphic 146G or another portion of the user interface 142. The graphic 146G may overlay or be arranged adjacent to one of the display windows 144 associated with the contact region CR, such as the seventh display window 144-7. Example parameters include the determined contact area ratio CAR and related parameters, such as the resection depth(s) associated with the respective reference planes REF (FIG. 4), first and second areas A1, A2, cortical areas CO1, CO2, cortical boundary areas CB1, CB2, cancellous areas CA1, CA2, cancellous coverage ratio CCR, cortical coverage ratio COR, and/or cortical support ratio CSR.

The comparison module 138 may be configured to generate one or more indicators PI in response to one or more predetermined criteria being met, including any of the predetermined criteria and/or thresholds disclosed herein. It should be understood that any of the indicators disclosed herein may a separate indicator or may be combined with one or more other indicators. The comparison module 138 may be configured to generate the indicator(s) PI in response to the contact area ratio CAR meeting one or more predetermined criteria, such as one or more predefined thresholds. The predefined thresholds may be configured or set in the system 120 according to various parameters, including procedure type, implant type, bone or joint type, bone quality, etc., and may be set and/or adjusted by the surgeon or assistant.

Various indicators PI may be utilized, including textual and graphical indicators. The indicators PI may include value indicators PV and threshold (e.g., graphical) indicators PT. The indicators PI may include a first indicator PH associated with the contact area ratio CAR, a second indicator PI2 associated with the cancellous coverage ratio CCR, and/or a third indicator PI3 associated with the cortical coverage ratio COR. The indicators PI may include a value indicator PVC associated with the cortical support ratio CSR (see also FIGS. 9-10).

The surgeon or assistant may interact with the user interface 142 to determine whether or not the proposed surgical plan 131 may establish sufficient bone fusion between adjacent bones. The comparison module 138 may be configured to cause the display module 136 to generate one or more indicators PI in response to a percentage of the contact area ratio CAR, contact to resection ratio CRR, cancellous coverage ratio CCR, cortical coverage ratio COR and/or cortical support ratio CSR exceeding respective predefined thresholds, as illustrated by the threshold indicator PT. The threshold indicator PT may include various states, such as an UP arrow indicating that the predefined threshold(s) are met (e.g., FIGS. 5-6) and a DOWN arrow indicating that the predefined threshold(s) are not met (e.g., FIG. 8). Other example indicators PI may include a shading or color coding status of the contact region CR (e.g., green for being met and red for not being met).

The comparison module 138 may be configured to generate one or more indicators PI (e.g., a first indicator) in response to the one or more predetermined criteria being met, including the contact area ratio CAR meeting a first predefined threshold. The first predefined threshold may be established by any values of the contact area ratio CAR disclosed herein. In implementations, the first predefined threshold may include a contact area ratio CAR that is greater than or equal to 0.4, or more narrowly greater than or equal to 0.5. The first predefined threshold may include the contact area ratio CAR being greater than or equal to 0.75, or more narrowly equal to 1.0 such that an entirety of the first resection surface S1 contacts the second resection surface S2 (see, e.g., FIG. 7).

The comparison module 148 may be configured to generate one or more indicators PI (e.g., a second indicator) in response to the one or more predetermined criteria being met, including the cancellous coverage ratio CCR meeting a second predefined threshold. The second predefined threshold may be established by any values of the cancellous coverage ratio CCR disclosed herein. In In implementations, the second predefined threshold(s) may include a cancellous coverage ratio CCR that is equal to or greater than 0.75, or more narrowly greater than or equal to 0.90. The second predefined threshold may include the cancellous coverage ratio CCR being equal to 1.0 such that an entirety of the first cancellous area CA1 contacts the second cancellous area CA2.

The comparison module 138 may be configured to generate one or more indicators PI (e.g., a third indicator) in response to the one or more predetermined criteria being met, including the cortical coverage ratio COR meeting a third predefined threshold. The third predefined threshold may be established by any values of the cortical coverage ratio COR disclosed herein. In implementations, the third predefined threshold may include a cortical coverage ratio COR that is greater than or equal to 0.03, or more narrowly greater than or equal to 0.05.

The comparison module 138 may be configured to generate one or more indicators PI (e.g., fifth indicator) in response to the one or more predetermined criteria being met, including the contact to resection ratio CRR meeting a fifth predefined threshold. The fifth predefined threshold may be established by any values of the contact to resection ratio CRR disclosed herein. In implementations, the fifth predefined threshold may include a contact to resection ratio CRR greater than or equal to 0.75, more narrowly greater than or equal to 0.90, or even more narrowly equal to 1.0. In implementations, the comparison module 138 may be configured to generate the one or more indicators PI (e.g., first indicator) in response to the contact area ratio CAR meeting the first predefined threshold and/or the contact to resection ratio CRR meeting the fifth predefined threshold.

The comparison module 138 may be configured to generate one or more indicators PI (e.g., sixth indicator) in response to the one or more predetermined criteria being met, including the cortical support ratio CSR meeting a sixth predefined threshold. The sixth predefined threshold may be established by any values of the cortical support ratio CSR disclosed herein. In implementations, the sixth predefined threshold may include a cortical support ratio CSR greater than or equal to 0.50, more narrowly greater than or equal to 0.75, more narrowly greater than or equal to 0.90, or even more narrowly equal to 1.0. In implementations, the comparison module 138 may be configured to generate the one or more indicators PI (e.g., first indicator) in response to the contact area ratio CAR meeting the first predefined threshold and/or the cortical support ratio CSR meeting the sixth predefined threshold. The indicators PI may include a value of the cortical support ratio CSR, as illustrated by the indicator PVC.

The comparison module 138 may be configured to cause the display module 136 to display the indicator(s) PI in the user interface 142 in response to the respective predefined threshold(s) and/or other predetermined criteria being met. The comparison module 138 may be configured to cause the display module 136 to display value indicators PV1-PV3, PVC associated with respective values of the contact area ratio CAR, cortical coverage ratio COR, cancellous coverage ratio CCR and cortical support ratio CSR in the graphic 146G or another portion of the user interface 142.

Figure 7:
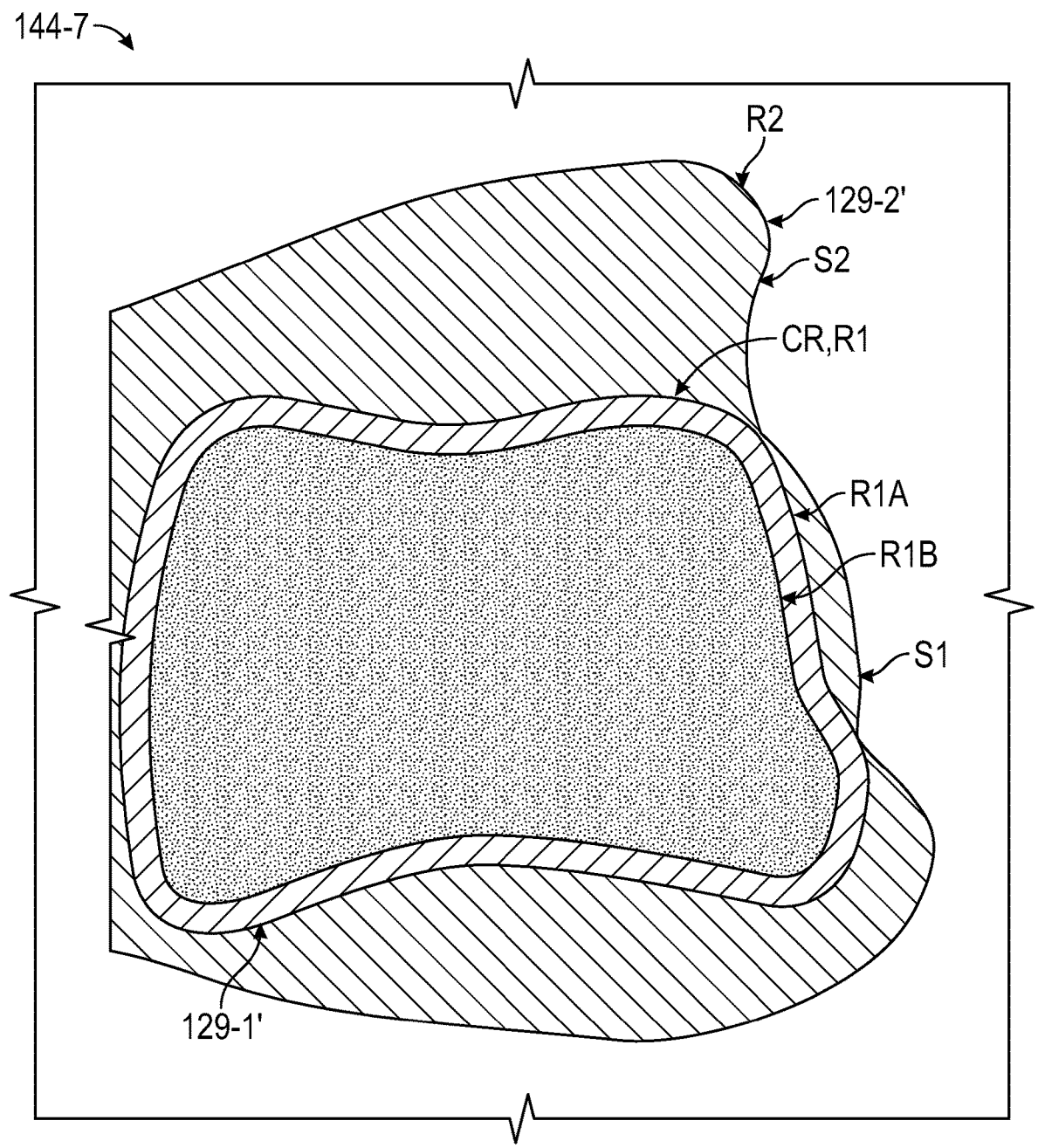
FIG. 7 illustrates a visual contrast applied to resection surfaces along a contact region between bone models.

The display module 136 may be configured to display a visual contrast between the contact region CR and a remainder of the resection surfaces S1, S2 that excludes the contact region CR, illustrated by respective graphics R1, R2 in FIG. 7. The visual contrast may be shown in a different shade and/or color than the remainder of the surface areas S1, S2 of the bone models 129-1, 129-2. The display module 136 may be configured to display a visual contrast between portions of the contact region CR associated with cortical bone and cancellous bone along the contact region CR, illustrated by respective graphics R1A, R1B. The visual contrast is shown as hatching in the display window 144-7 of FIG. 7 for illustrative purposes. The user may select a button 146B in the menu 146M associated with the seventh display window 144-7 to toggle between the views of the contact region CR of FIGS. 6 and 7, which may provide the surgeon different perspectives of the contact region CR and related anatomy of the patient prior to approving or revising a surgical plan 131.

Figure 8:
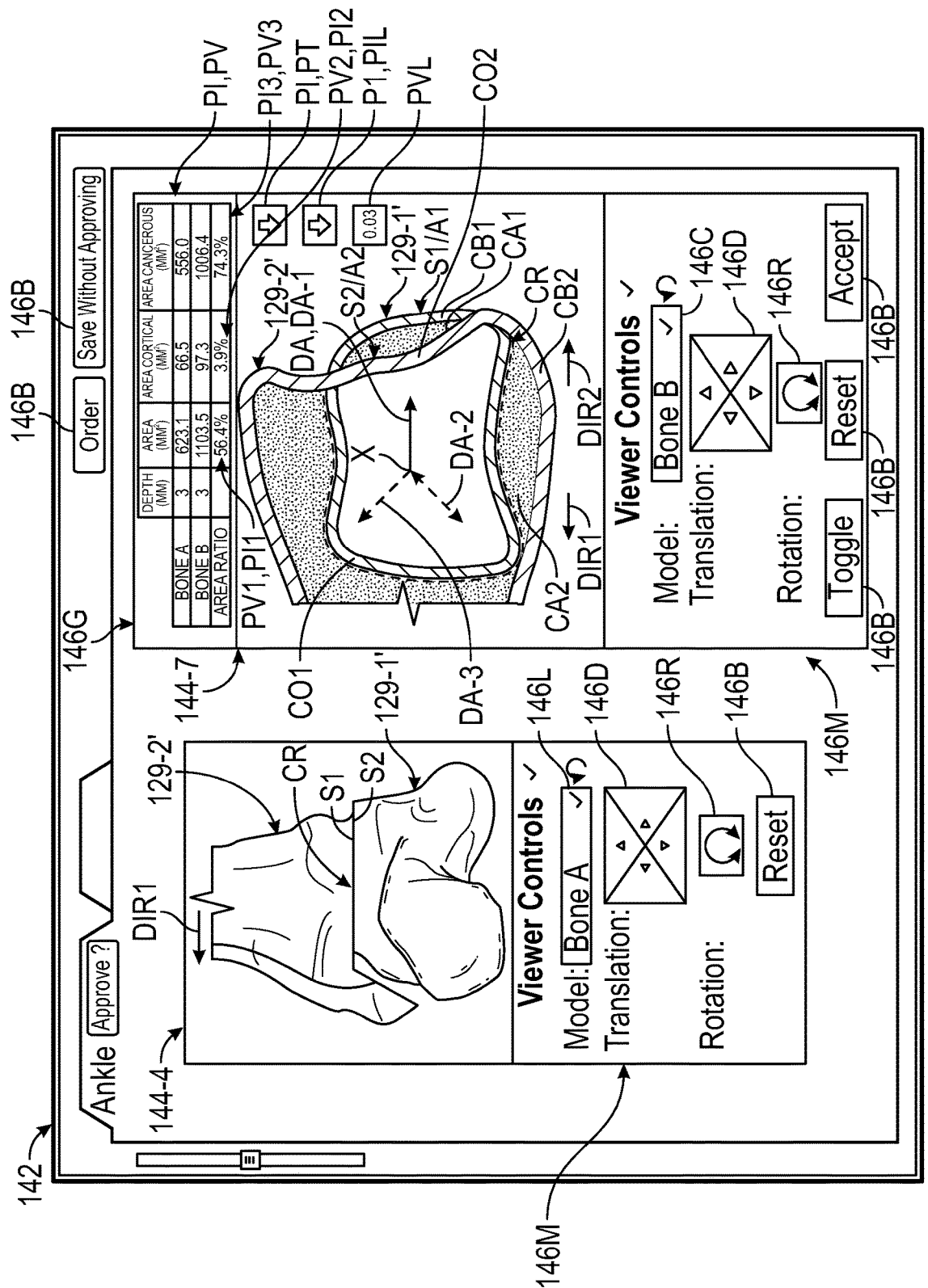
FIG. 8 illustrates the user interface of FIG. 2 including display windows depicting resection surfaces, a contact region between bone models and exemplary indicators associated with a change in relative position between the bone models.

Referring to FIG. 8, with continuing reference to FIGS. 2 and 6, the surgeon or assistant may interact with the user interface 142 to cause one or more adjustments relating to the contact region CR and bone models 129-1', 129-2'. The spatial module 137 may be configured to cause relative movement between the resection surfaces S1, S2 along the contact region CR in response to user interaction with the user interface 142. In implementations, the user may interact with the directional indicator 146D and/or 146R or directly with the bone models 129-1', 129-2' in the display window 144-7 to cause relative movement. The second bone model 129-2' may be moved in a direction DIR1, for example, causing a change (e.g., decrease or increase) in the contact area ratio CAR. The comparison module 138 may be configured to update a value of the contact area ratio CAR, cancellous coverage ratio CCR, contact to resection ratio CRR, cortical coverage ratio COR and/or cortical support ratio CSR in response to the relative movement. The values may be updated in the graphic 146G. The updated values may cause a change in the status of the indicator PT based on whether or not the contact area ratio CAR, cancellous coverage ratio CCR, contact to resection ratio CRR, cortical coverage ratio COR and/or cortical support ratio CSR meet the predetermined criteria, including any of the predefined thresholds disclosed herein. The surgeon may evaluate the ratios CAR, CCR, CRR, COR and/or CSR to determine suitable resection depths.

At least one of the bone models 129-1', 129-2' may be associated with a contact axis X intersecting the contact region CR. The contact axis X may extend through and may be perpendicular to the resection surfaces S1, S2. The comparison module 138 may be configured to determine a set of values of the contact area ratio CAR associated with different positions of the first bone model 129-1' relative to the second bone model 129-2' along the contact region CR, with values in the set of values of the contact area ratio CAR corresponding to respective polar coordinates or directions from the contact axis X. The comparison module 138 may be configured to determine a maximum value of the set of values of the contact area ratio CAR in which contact is maintained between the resection surfaces S1, S2. Each value may be associated with a respective coordinate along the resection surface S1/S2 such that values may be determined for at least some or substantially all relative positions between the bone models 129-1', 129-2' in which contact along the resection surfaces S1, S2 is maintained. In implementations, values of the contact area ratio CAR for only small incremental changes in position may be determined, such as a single change in position or direction.

The display module 136 may be configured to display a first directional indicator DA extending in a first direction relative to the contact axis X. The first direction may be associated with the maximum value of the contact area ratio CAR determined by the comparison module 138. Exemplary directional indicators DA-1, DA-2, DA-3 are illustrated in FIG. 8, with directional indicators DA-2, DA-3 shown in dashed lines to illustrate indicators DA that may associated with other exemplary positions between the bone models 129-1', 129-2'. In implementations, the directional indicator DA may be a vector from the contact axis X. The user may infer an amount and direction of suggested movement based on the vector that may result in an increase a value of the contact area ratio CAR, which may promote improved bone fusion between the resection surfaces S1, S2.

Figures 9, 10:
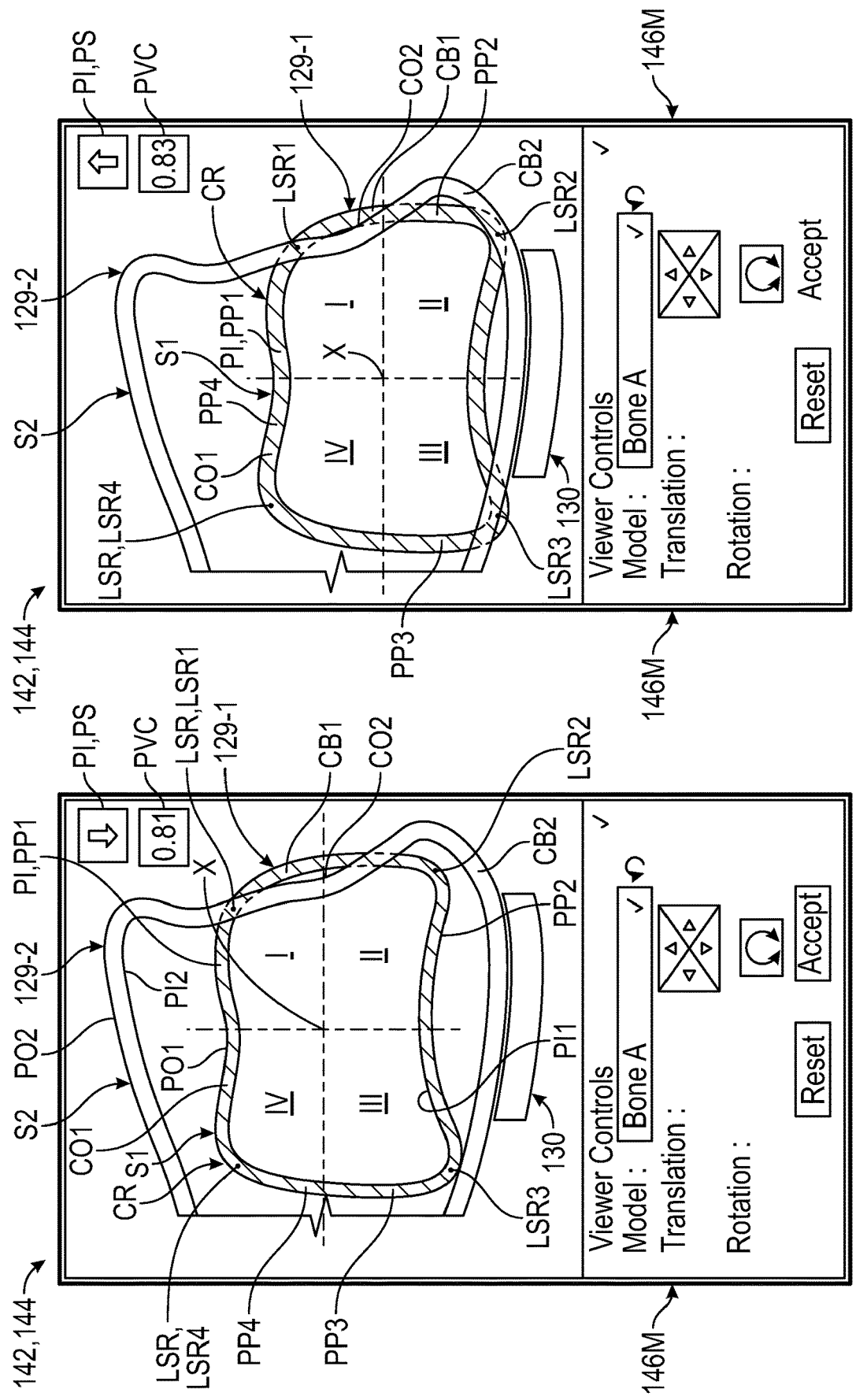
FIG. 9 illustrates the user interface of FIG. 2 including a display window depicting resection surfaces and exemplary indicators associated with localized support regions.
FIG. 10 illustrates the display window of FIG. 9 depicting the resection surfaces and exemplary indicators associated with a change in relative position between the bone models.

Referring to FIG. 9, with continuing reference to FIGS. 2 and 6, the system 120 may be configured to determine other aspects associated with the boundary areas CB1, CB2 of the bone models 129-1, 129-2. The spatial module 137 may be configured to establish one or more localized support regions LSR along one of the boundary areas CB1, CB2, such as the boundary area CBE The localized support regions LSR are separate and distinct from each other. In the implementation of FIG. 9, the spatial module 137 establishes at least four localized support regions LSR (indicated at LSR1-LSR4). The localized support regions LSR1-LSR4 may be spaced apart from each other along a perimeter of the boundary area CBE Although four localized support regions LSR are illustrated in FIG. 9, it should be understood that fewer or more than four localized support regions LSR may be established utilizing the techniques disclosed herein, including two or three localized support regions LSR. The spatial module 137 may be configured to determine whether or not contact between the boundary areas CB1, CB2 is established at each of the localized support regions LSR. Contact between the boundary areas CB1, CB2 at the localized support region(s) LSR may be associated with improved support by the bone model 129 associated with a cortical wall of the load bearing bone. In the implementation of FIG. 9, the bone models 129 may be positioned such that the first boundary area CB1 of the first bone model 129-1 may support the second boundary area CB2 of the second bone model 129-2 at one or more of the localized support regions LSR.

Various techniques may be utilized to establish the localized support regions LSR. The spatial module 137 may be configured to divide the first resection surface S1 (and/or second resection surface S2) into two or more sectors. The sectors may be separate and distinct from each other. The spatial module 137 may divide the sectors according to equal angles about the axis X. Together the sectors may comprise an entirety of the respective boundary area CB1/CB2 and/or resection surface S1/S2. In the implementation of FIG. 9, the spatial module 137 may be configured to establish at least four sectors (indicated at I-IV) and at least four localized support regions LSR (indicated at LSR1-LSR4). The sectors I-IV may be established at 90 degree increments relative to the axis X. Each localized support region LSR1-LSR4 may be associated with a respective one of the sectors I-IV. It should be understood that fewer or more than four sectors may be established utilizing the techniques disclosed herein. A quantity of sectors may be established according to the selected bone model(s) 129 and/or other aspects of the surgical plan 131, including whether or not the surgical plan 131 comprises one or more implant models 130 to be secured to the selected bone model(s) 129. The spatial module 137 may be configured to establish each localized support region LSR at an outermost position in the respective one of the sectors along the boundary area CB1/CB2 relative to the contact axis X. The localized support region LSR may be equidistant between the inner and outer perimeters PI1/PI2, PO1/PO2. Each localized support region LSR may be a single point or may be a localized segment along the boundary area CB1/CB2. In implementations, each localized support region LSR may be a region having a length that spans less than or equal to ±10 degrees, or more narrowly less than or equal to ±5 degrees, from the outermost position relative to the contact axis X along the perimeter of the boundary area CB1/CB2. A width of the localized support region LSR may extend between the inner and outer perimeters PI1/PI2, PO1/PO2. In implementations, the surgeon or other user may interact with the user interface 142 to set and/or adjust a position of each localized support region LSR. Spacing the localized support regions LSR utilizing the techniques disclosed herein may promote relatively greater support by the load bearing bone and improved distribution, may improve distribution of compressive loads between adjacent bones, and may improve fusion between the resection surfaces S1, S2 along the contact region CR.

The comparison module 138 may be configured to generate one or more indicators PI in response to one or more predetermined criteria being met. The predetermined criteria may include a predefined support threshold, which may be associated with a minimum quantity of localized support regions LSR in which contact between the boundary area CB1, CB2 is established. The minimum quantity may include at least one, or more than one, localized support regions LSR. In implementations, the minimum quantity may include two, three or four localized support region LSR. The minimum quantity may include all, or fewer than all, of the localized support region LSR established by the spatial module 137.

The indicators PI may include a support indicator PS. The support indicator PS may include various states, such as an UP arrow indicating that the predefined support threshold(s) are not met (e.g., FIG. 10) and a DOWN arrow indicating that the predefined support threshold(s) are not met (e.g., FIG. 9).

The indicators PI may include graphical indicators PP1-PP4 associated with the respective sectors I-IV and localized support regions LSR1-LSR4. Each of the graphical indicators PP1-PP4 may include a shading or color coding status of the respective portion of the boundary area CB1 (e.g., green for contact between the boundary areas CB1, CB2 at the support region LSR and red for a lack of contact between the boundary areas CB1, CB2 at the support region LSR, shown in hatching in FIGS. 9-10 for illustrative purposes). The comparison module 138 may be configured to cause the display module 136 to display the status of the graphical indicators PP1-PP4 based on whether or not contact is established between the boundary areas CB1, CB2 at the respective localized support regions LSR1-LSR4. Each of the indicators PP1-PP4 may serve as a warning to the surgeon in scenarios in which a lack of cortical-to-cortical support may exist at the respective localized support regions LSR1-LSR4.

The surgeon, assistant or other user may interact with the menu 146M, directly with the display window 144, and/or with another portion of the user interface 142 to change a relative position between the first and second bone models 129-1, 129-2, as illustrated by FIG. 10. In implementations, the predetermined criteria may include contact between the boundary areas CB1, CB2 for at least two the localized support regions LSR that are nearest to the implant model 130, as illustrated by the localized support regions LSR2, LSR3 relative to implant model 130 of FIG. 10. In the implementation of FIG. 10, the localized support regions LSR1-LSR3 may correspond to contact between the boundary areas CB1, CB2 associated with the medial, lateral and anterior regions of the load bearing bone (e.g., talus) and the supported bone (e.g., tibia).

Figure 11:
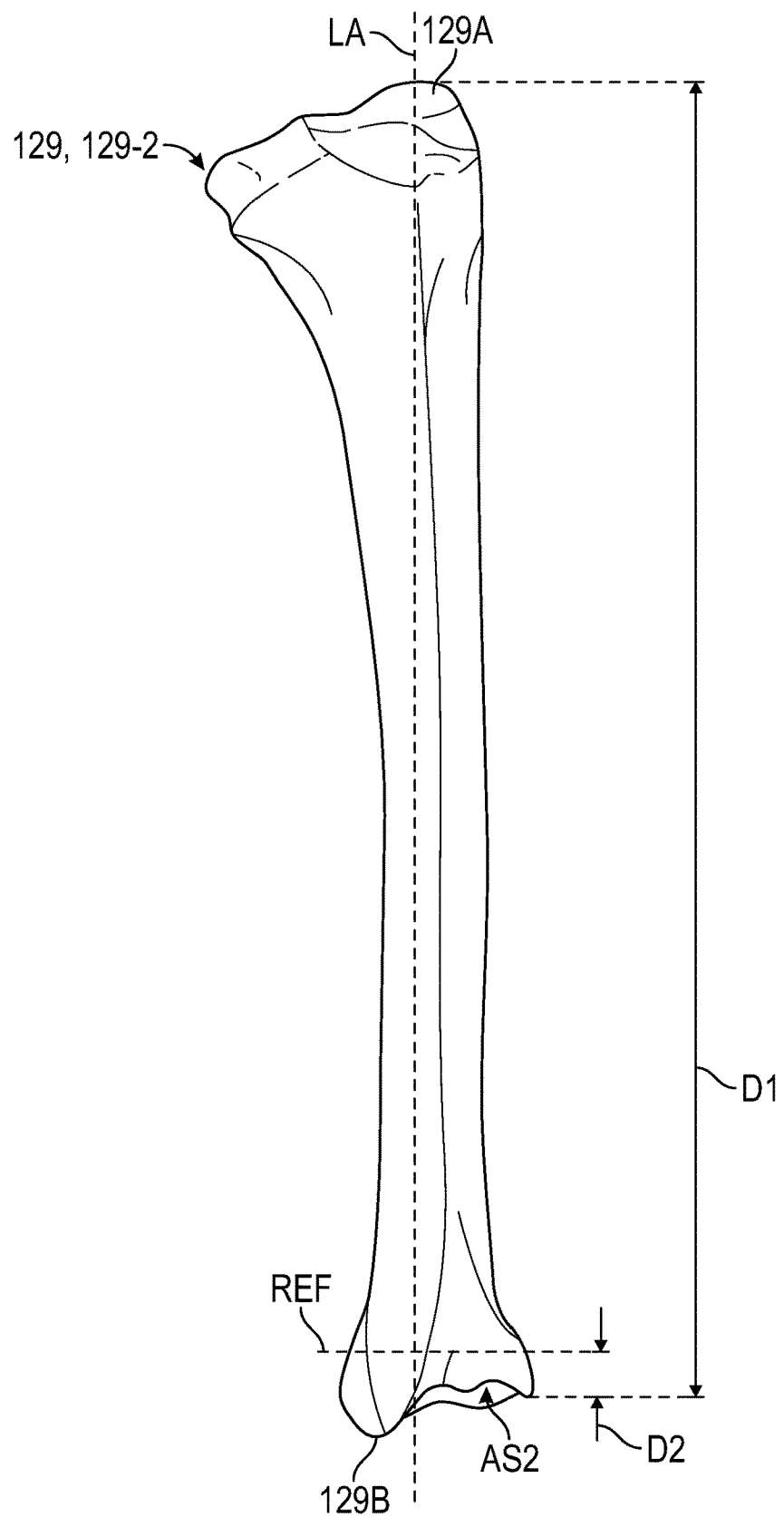
FIG. 11 illustrates exemplary parameters associated with a bone model.

Referring to FIG. 11, with continuing reference to FIGS. 2 and 6, the predetermined criteria may include a length ratio associated with a shortening of the respective bone model 129 relative to the specified resection plane REF (see also FIG. 4). The spatial module 137 may be configured to determine a first distance D1 along a longitudinal axis LA between a first end 129A and a second end 129B of the bone model 129, such as the second bone model 129-2. The spatial module 137 may be configured to determine a second distance D2 along the longitudinal axis LA between the specified reference plane REF and the second end 129B of the bone model 129.

The comparison module 138 may be configured to determine a length ratio D2:D1 in response to setting a position of the reference plane REF. The length ratio D2:D1 may be defined as a ratio of the second distance D2 divided by the first distance D1. The comparison module 138 may be configured to generate a length indicator PIL in response to the length ratio D2:D1 being less than (or greater than) a predefined length threshold. The indicator PIL may include various states relating to the resection depths, such as an UP arrow indicating that the predefined length threshold is met (e.g., FIGS. 5-6) and a DOWN arrow indicating that the predefined length threshold is not met (e.g., FIG. 8). In implementations, the predefined length threshold may be less than or equal to 0.05, or more narrowly less than or equal to 0.01. The indicator PIL may serve to provide an indication to the surgeon whether to increase or decrease a depth of the resection plane REF associated with the bone model 129, which may reduce limb shortening and improve healing and mobility of the patient.

Figure 12:
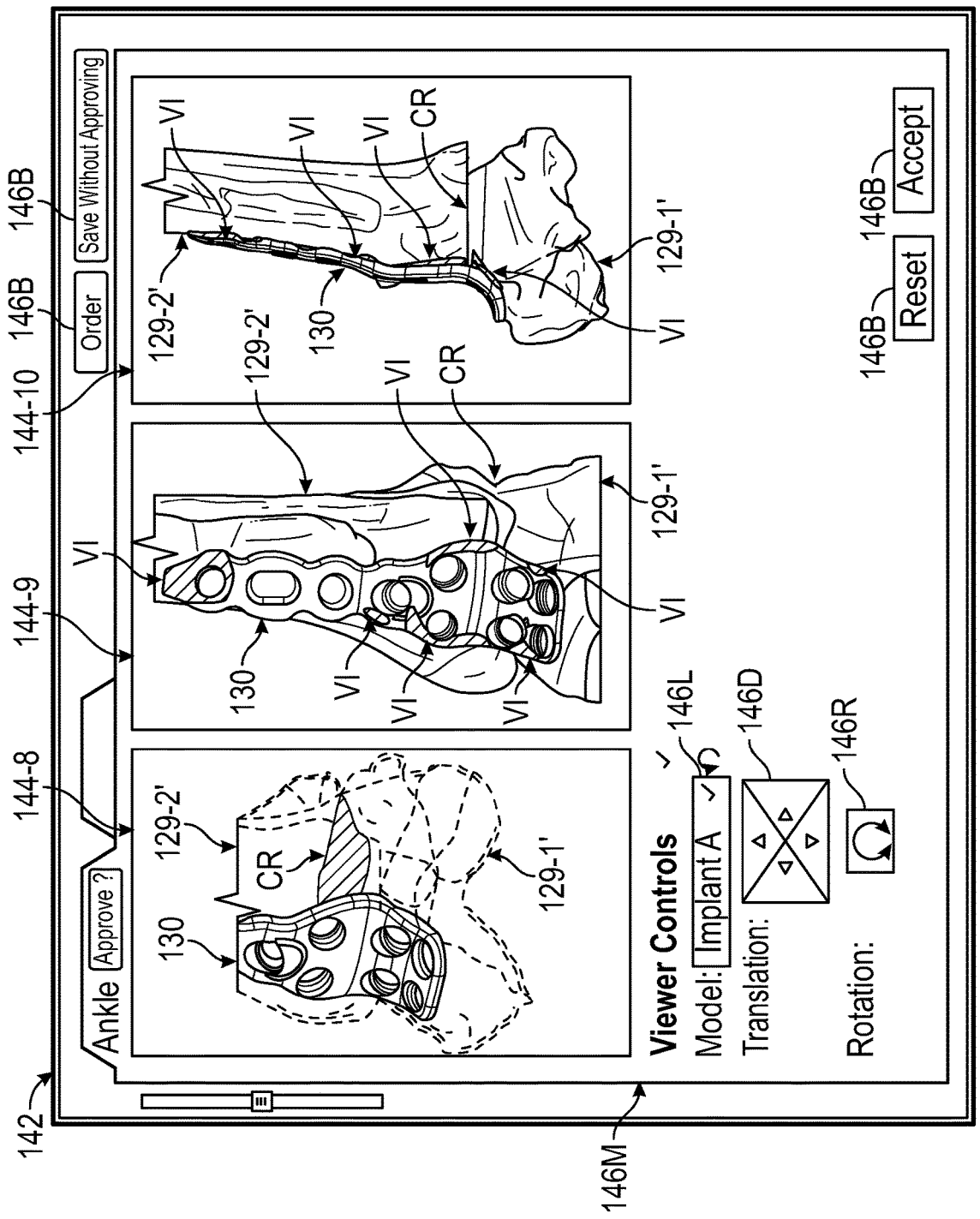
FIG. 12 illustrates the user interface of FIG. 2 including display windows depicting an implant model positioned relative to adjacent bone models and visual indicators.
Figure 13:
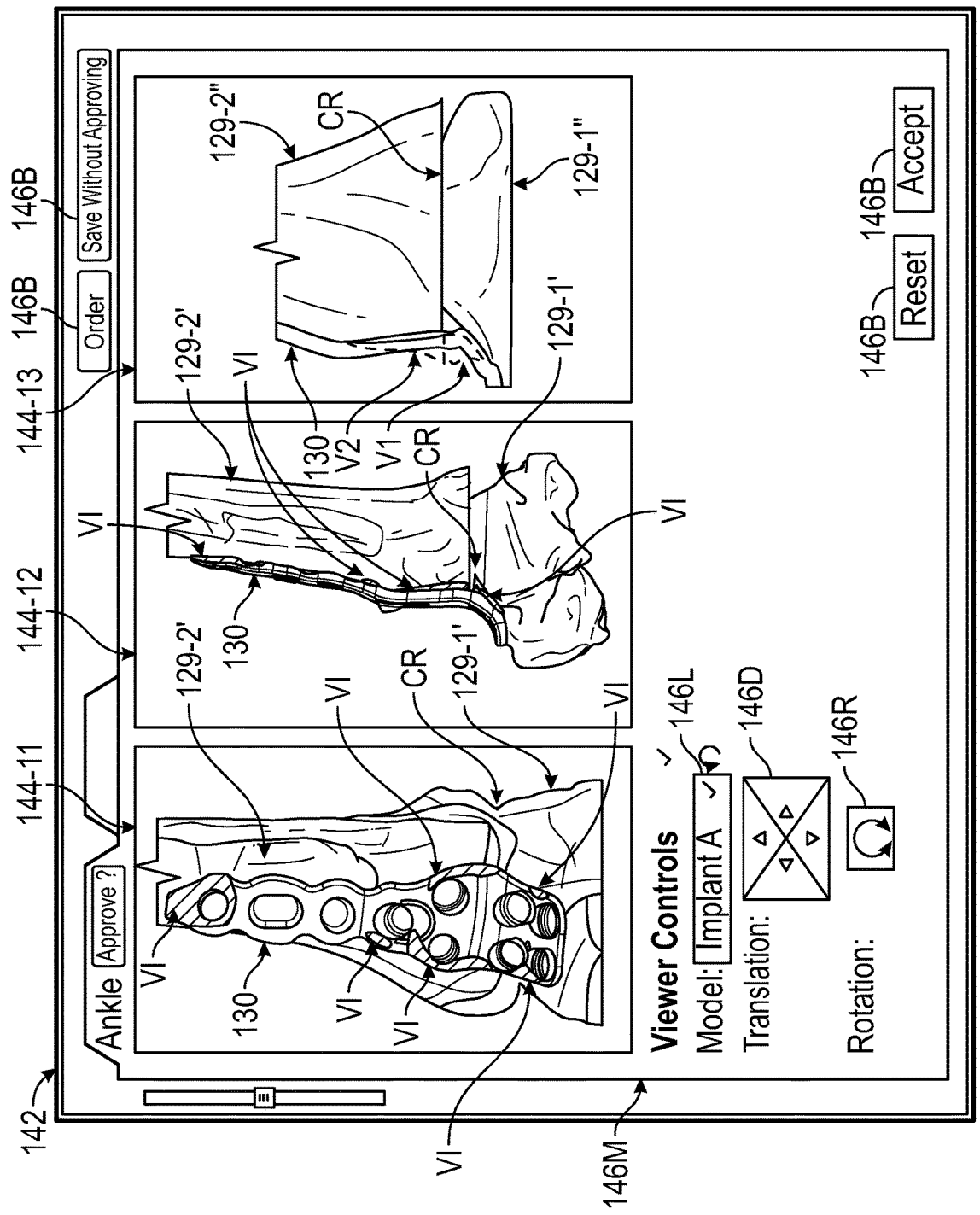
FIG. 13 illustrates the user interface of FIG. 2 including display windows depicting an implant model positioned relative to adjacent bone models and visual indicators.

Referring to FIGS. 12-13, with continuing reference to FIG. 2, the display module 136 may be configured to display one or more implant models 130 in one or more of the display window(s) 144 of the user interface 142 (see also FIGS. 9-10). Each implant model 130 can be associated with any of the implants disclosed herein. The display windows 144 may include eighth through tenth display windows 144-8 to 144-10 (FIG. 12) and eleventh through thirteen display windows 144-11 to 144-13 (FIG. 13). The spatial module 137 may be configured to position the implant model(s) 130 relative to the first and second bone models 129-1', 129-2' automatically and/or in response to user interaction with the user interface 142.

The system 120 may be configured to facilitate positioning of the selected implant model(s) 130 relative to the bone models 129-1', 129-2'. For example, the surgeon may desire to place the implant model 130 relatively closer to the bone models 129-1', 129-2' than would be permitted by an existing surface contour of the bone models 129-1', 129-2' due to a spatial conflict. The surgeon or assistant may interact with the user interface 142 to cause at least a portion of the volume of the selected implant model 130 to overlap with a volume of the respective bone models 129-1', 129-2' resulting in a spatial conflict.

The spatial module 137 may be configured to determine one or more overlapping volumes between the implant model 130 and the first and second bone models 129-1', 129-2' associated with the overlapped positioning. The display module 136 may be configured to display a visual contrast between the one or more overlapping volumes and a remainder of the volumes of the first and second bone models 129-1', 129-2' that excludes the one or more overlapping volumes. In implementations, the visual contrast may be established by one or more visual indicators VI applied to the overlapping volumes (shown in hatching for illustrative purposes). The visual contrast may serve as a heat map to emphasize areas of spatial conflict, which the surgeon may utilize to evaluate whether planned implant repositioning and/or removal of bone with one or more relief cuts is indicated prior to approving the surgical plan 131. The relief cuts may be simulated by partially or substantially removing the overlapping volumes from display in the user interface 142. One of ordinary skill in the art would understand how to program the spatial module 137 with logic to determine the overlapping volumes, including one or more CAD tools, libraries, etc.

The spatial module 137 may be configured to generate an iteration of the first and second bone models 129-1", 129-2". The bone models 129-1", 129-2" may exclude the one or more overlapping volumes, as illustrated by display window 144-13 with overlapping volumes V1, V2 shown in dashed lines and implant model 130 for illustrative purposes. The display module 136 may be configured to display the implant model(s) 130 positioned relative to the bone models 129-1", 129-2", as illustrated by display window 144-13. The bone models 129-1", 129-2" may be separate models or may be stored as one or more revisions to the respective bone models 129-1/129-1', 129-2/129-2'.

Referring to FIGS. 14-15, with continuing reference to FIGS. 2 and 6, the spatial module 137 may be configured to determine one or more trajectories T for placement of respective guide members. Exemplary guide members may include guide pins (e.g., Kirschner wires), fasteners, etc. The trajectories T may include first through fourth trajectories T1-T4. Each trajectory T may include a location of insertion along a surface of the bone model 129-1'/129-2' and/or orientation along an axis passing through the location. The trajectories T may be associated with respective guide pins configured for insertion into bone (see, e.g., FIGS. 27 and 36). The spatial module 137 may be configured to determine the trajectories T in response to one or more (or each) of the predetermined criteria being met, including any of the predetermined criteria disclosed herein, such as one or more (or each) of the predefined thresholds being met. The predefined thresholds may be associated with the determined contact area ratio CAR and/or related parameters, such as the determined cancellous coverage ratio CCR and determined cortical coverage ratio COR. The predefined threshold(s) may be associated with the determined cortical support ratio CSR. In implementations, the surgeon may interact with the user interface 142 to approve the defined reference planes REF associated with the resection surfaces S1, S2.

The trajectories T1-T4 may be associated with respective positions along the bone models 129-1', 129-2' relative to the contact region CR (FIG. 14). The spatial module 137 may be configured to establish the trajectories T1-T4 based on one or more landmarks L, such as the landmarks L1, L2, and/or the defined reference planes REF (see also FIG. 4). The surgeon or assistant may interact with the user interface 142 to adjust a position and/or orientation of each trajectory T.

The comparison module 138 may be configured to generate one or more settings or dimensions associated with an instrument based on the trajectories T. Exemplary instruments may include cutting blocks, trajectory guides, etc., including any of the instruments disclosed herein. The dimensions may be utilized to fabricate a patient-specific instrument for implementation of the surgical plan 131. The trajectories T, settings and/or dimensions may be stored in the surgical plan 131. The surgeon may interact with the user interface 142 to approve the surgical plan 131, which may be stored in the database 128 for later retrieval.

Figure 17:
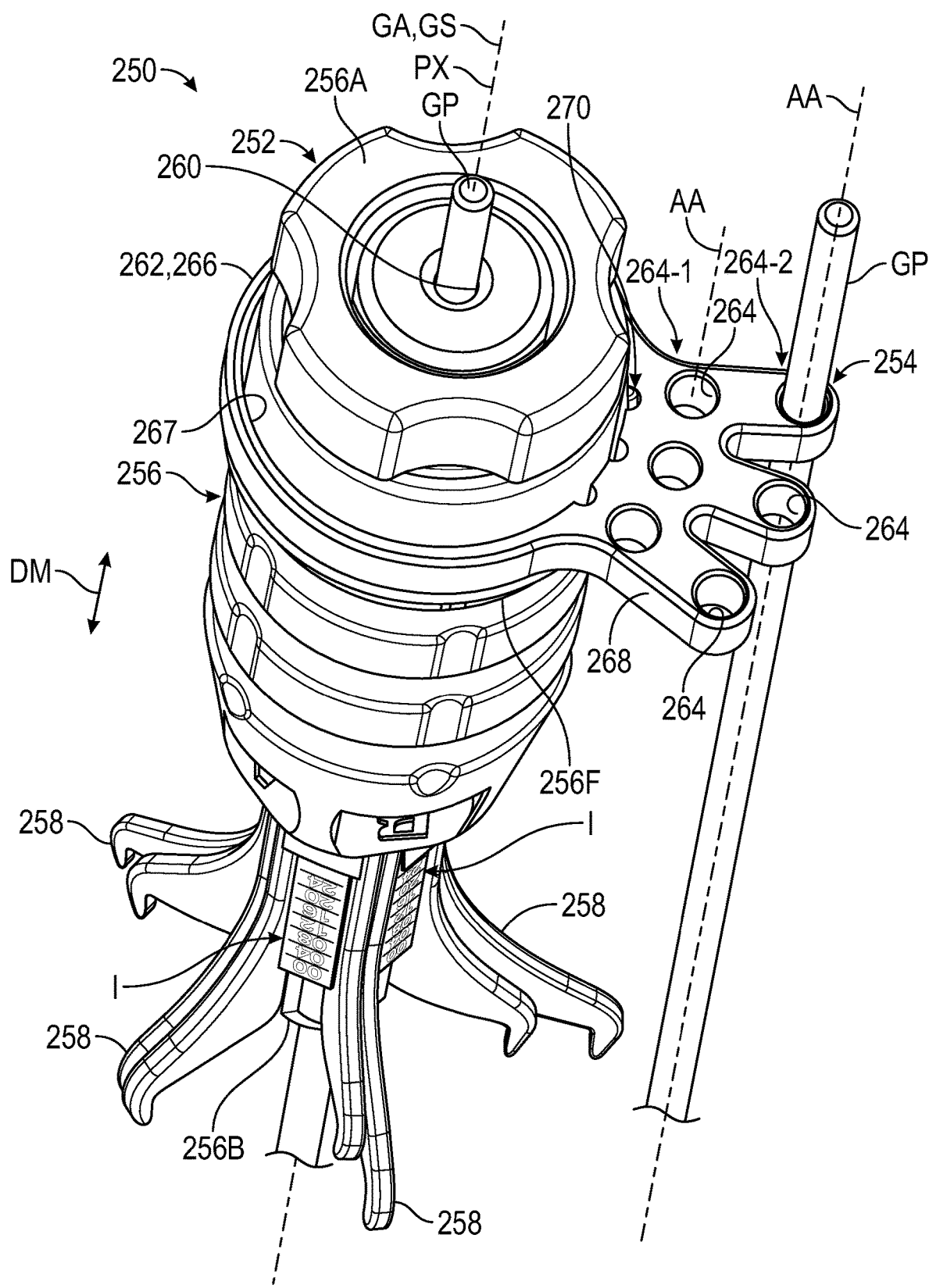
FIG. 17 illustrates a perspective view of an exemplary trajectory assembly.

FIG. 17 illustrates an exemplary trajectory assembly 250 that may be utilized for various surgical procedures, including preparation of a surgical site. The trajectory assembly 250 may be configured to position one or more guide members relative to bone or other tissue based on one or more predetermined trajectories. The trajectory assembly 250 may be utilized in an ankle reconstruction to facilitate the removal of bone along an articulating surface of a tibia and/or talus. A location of the bone to be removed may be determined during preoperative planning utilizing the system 120.

The assembly 250 may include a trajectory guide 252 and a secondary guide 254. The secondary guide 254 may be releasably secured or otherwise coupled to the trajectory guide 252. In other implementations, the secondary guide 254 may be integrally formed with the trajectory guide 252. The trajectory guide 252 and secondary guide 254 may be utilized in the positioning of one or more guide members relative to each other and bone or other tissue at a surgical site.

The trajectory guide 252 may include an elongated guide body 256 and at least one or more arm members 258 coupled to the guide body 256. The guide body 256 may extend along a longitudinal axis GA between a first (e.g., proximal) end portion 256A and a second (e.g., distal) end portion 256B. The guide body 256 may be configured to set a trajectory of one or more guide member relative to tissue such as bone. The guide body 256 may include a guide passage 260 extending along a passage axis PX. The passage axis PA may be substantially collinear with or parallel to the longitudinal axis GA. The guide passage 260 may be dimensioned to receive a guide member, such as a guide pin GP.

The guide pin GP may be positioned at a predetermined trajectory relative to bone along a surgical site. The arm members 258 may be configured to set an orientation of the longitudinal axis GA of the guide body 256 relative to bone along the surgical site and establish a trajectory of the guide pin GP insertable through the guide passage 260 relative to the bone or other tissue.

The trajectory guide 252 may include an array of arm members 258 distributed about a periphery and longitudinal axis GA of the guide body 256. Each of the arm members 258 may be integrally formed with or attached to the guide body 256 at a fixed position, or may be moveable relative to each other and/or the guide body 256. The arm members 258 may extend laterally from the guide body 256. Although the trajectory guide 252 is illustrated having a total of five arm members 258, it should be understood that fewer or more than five arm members 258 may be utilized in accordance with the teachings disclosed herein, such as only one arm member 258.

Each of the arm members 258 may be movable in a first (e.g., axial) direction DM relative to the guide body 256 to set a trajectory of the guide member relative to tissue such as bone. The direction DM may be substantially parallel to the longitudinal axis GA and/or passage axis PX. Each of the arm members 258 may be independently movable in the direction DM and trajectory of the guide member(s) relative to tissue such as bone. The arm members 258 may be configured relative to indicia I. The indicia I may be associated with respective positions relative to the longitudinal axis GA. The surgeon or assistant may move the arm members 258 relative to the indicia I according to one or more settings specified in a surgical plan 131 generated by the system 120 (FIG. 2). The arm members 258 may set the trajectory in response to abutment with a contact surface along the bone. Each of the arm members 258 may include various geometries and configurations to establish a trajectory of the longitudinal axis GA of the guide body 256 and associated guide member(s) relative to the surgical site. In implementations, the arm members 258 may be dimensioned to establish a single point of contact, a stair casing arrangement including two or more points of contact (see, e.g., FIG. 17), a wrapping arrangement including two or more points of contact established by overhanging arm members (see, e.g., FIG. 17), and hooking (e.g., C-shaped) overhanging arm members.

Referring to FIGS. 17-18, the secondary guide 254 may include a main body 262 extending along a guide (e.g., longitudinal) axis GS. The guide axis GS may be substantially collinear with or otherwise parallel to the longitudinal position GA of the trajectory guide 252 in an installed position.

The main body 262 may include a sleeve portion 266 and a flange portion 268 extending outwardly from a perimeter of the sleeve portion 266. The secondary guide 254 may be carried by the guide body 256 in the installed position. The sleeve portion 266 may have a generally annular or hoop-shaped geometry dimensioned to mate with the outer periphery of the guide body 256. The sleeve portion 266 may have a sleeve passage 267 dimensioned to at least partially receive a proximal end portion 256A of the guide body 256.

The trajectory guide 252 may include an abutment 256F along the outer periphery of the guide body 256 (FIG. 17). The abutment 256F may be an annular flange extending outwardly from the guide body 256. The abutment 256F may serve as an axial stop to limit axial movement of the secondary guide 254 relative to the longitudinal axis GA of the guide body 256. The secondary guide 254 may be translatable along the passage axis PX and/or longitudinal axis GA to engage the abutment 256F such that relative movement between the secondary guide 254 and guide body 256 is limited relative to the axes PX and/or GA.

The main body 262 may include at least one or more apertures 264. Each aperture 264 may be established with respect to a predefined position relative to the guide axis GS of the secondary guide 254. At least one of the apertures 264 may be established along the flange portion 268. The apertures 264 may be established at different pitches relative to the guide axis GS. The apertures 264 may be arranged in one or more rows distributed about the guide axis GS, as illustrated by first and second rows 264-1, 264-2 along the flange portion 268. The second row 264-2 of apertures 264 may be outward of the first row 264-1 of apertures relative to the guide axis GS. Two or more apertures 264 of adjacent rows 264-1, 264-2 may be substantially circumferential aligned with respect to the guide axis GS, but may be associated with different offsets or distances from the guide axis GS to position guide pins GP at different distances from each other. Each aperture 264 of the first row 264-1 of apertures 264 may be substantially circumferentially aligned with a respective aperture 264 of the second row 264-2 of apertures 264 relative to the guide axis GA. The apertures 264 may be spaced apart in approximately 1 degree increments relative to the guide axis GA.

Each aperture 264 may be dimensioned to at least partially receive a respective guide pin GP along a respective aperture axis AA. The secondary guide 254 may be coupled to the guide body 256 such that each aperture axis AA is offset from the passage axis PX, longitudinal axis GA and/or guide axis GS by a predetermined distance and predetermined circumferential position. Each aperture axis AA may be substantially parallel to the axes PX, GA and/or GS. The selected aperture(s) 364 may be specified in the surgical plan 131 (FIG. 2).

The secondary guide 254 may be arranged at different orientations relative to the trajectory guide 252. The assembly 250 may include one or more features to set the relative orientation between the trajectory guide 252 and secondary guide 254 along an interface 270 in an installed position. Referring to FIG. 18, with continuing reference to FIG. 17, the trajectory guide 252 may include a first interface feature 271 along the guide body 256. The secondary guide 254 may include a second interface feature 272 along the sleeve portion 266. The first interface feature 271 may be dimensioned to engage with the second interface feature 272 at the interface 270 to set the position of the secondary guide 254 and limit relative rotation between the guide body 256 and secondary guide 254 with respect to the longitudinal axis GA. The first interface feature 271 may be utilized to vary and set the positions of the apertures 264 relative to the guide axis GS, which may provide the surgeon or assistant improved versality in selecting desired trajectories of the guide pins GP.

The first interface feature 271 may be a protrusion extending outwardly from the outer periphery of the guide body 256, and he second interface feature 272 may include at least one groove along the sleeve passage 267 dimensioned to mate with the protrusion 271, although an opposite arrangement may be utilized. The second interface feature 272 may include an array of the grooves distributed along the sleeve passage 267. The protrusion 271 may be insertable within a selected one of the grooves 272 to set a circumferential position of the apertures 264 relative to the axes PX and/or GA of the guide body 256 and to limit relative rotation between the guide body 256 and secondary guide 254.

Figure 34:
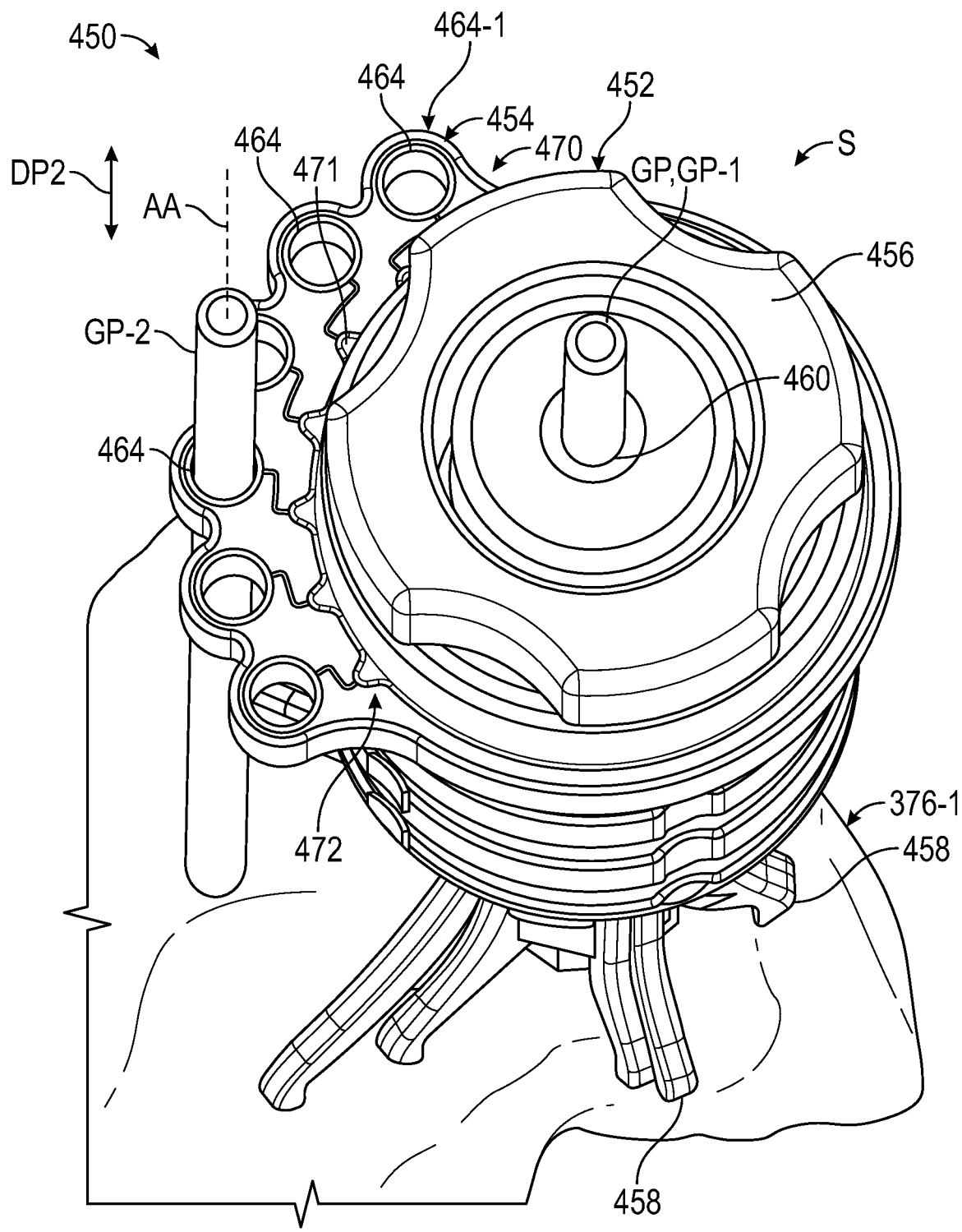
FIG. 34 illustrates a perspective view of a secondary guide coupled to the trajectory assembly of FIG. 32.
Figure 35:
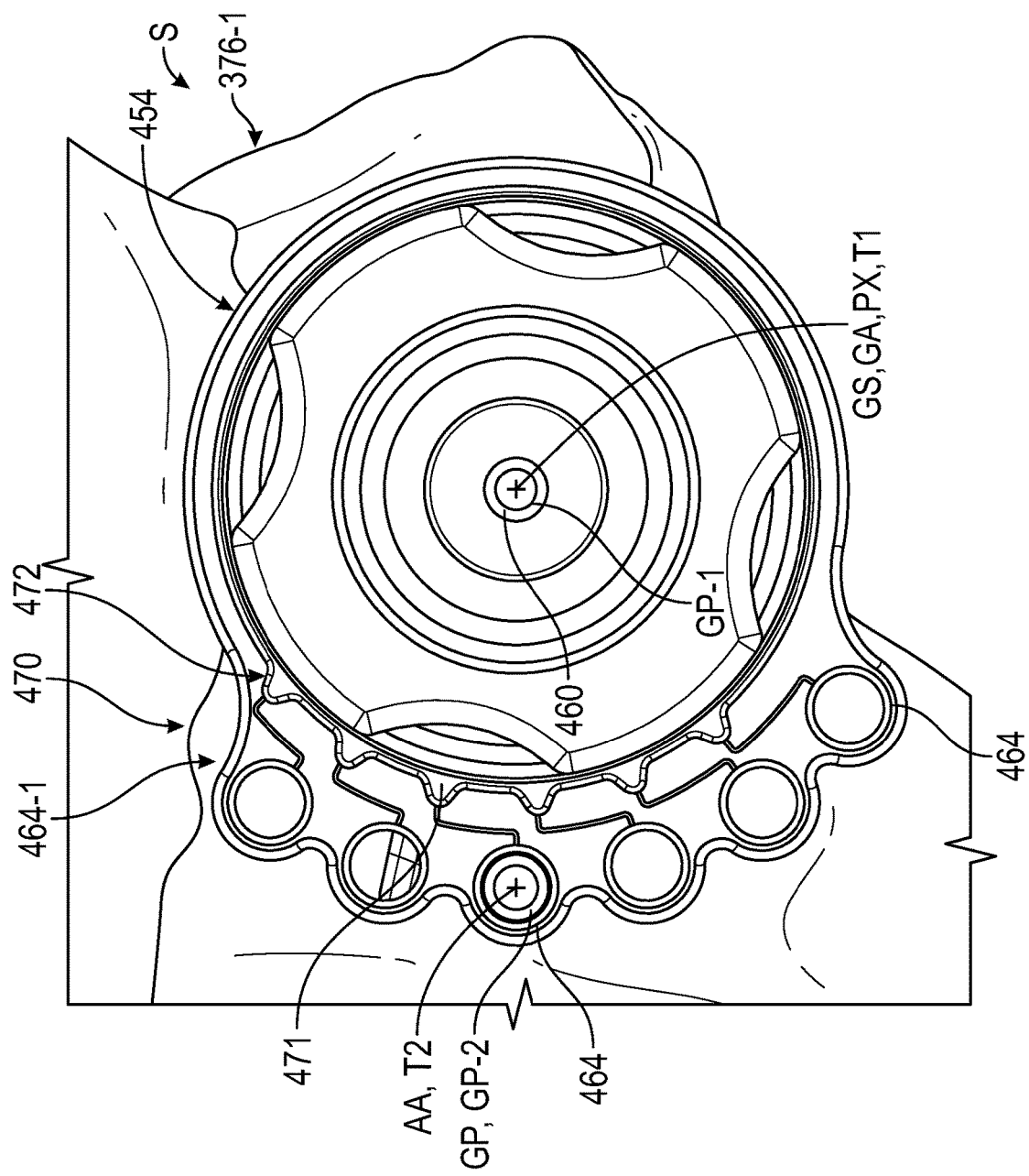
FIG. 35 illustrates an end view of the trajectory assembly of FIG. 34.

The trajectory guide 252 may be utilized with one or more secondary guides, such as a secondary guide 354 (FIG. 19) and/or secondary guide 454 (FIGS. 34-35). Referring to FIG. 19, the secondary guide 354 may include a sleeve portion 366 and a flange portion 368. The flange portion 368 may establish first and second rows 364-1, 364-2 of apertures 364. The flange portion 368 may include a first section 368A and a second section 368B that establish a stepped arrangement. The first row 364-1 of apertures 364 may be established along the first section 368A. The second row 364-2 of apertures 364 may be established along the second section 368B. The first and second rows 364-1, 364-2 may be utilized to position guide pins in respective bones. For example, the second row 364-2 may be utilized to position a guide pin in a long bone such as a talus, and the first row 364-1 may be utilized to position a guide pin in an adjacent bone, such as a talus.

Figure 20:
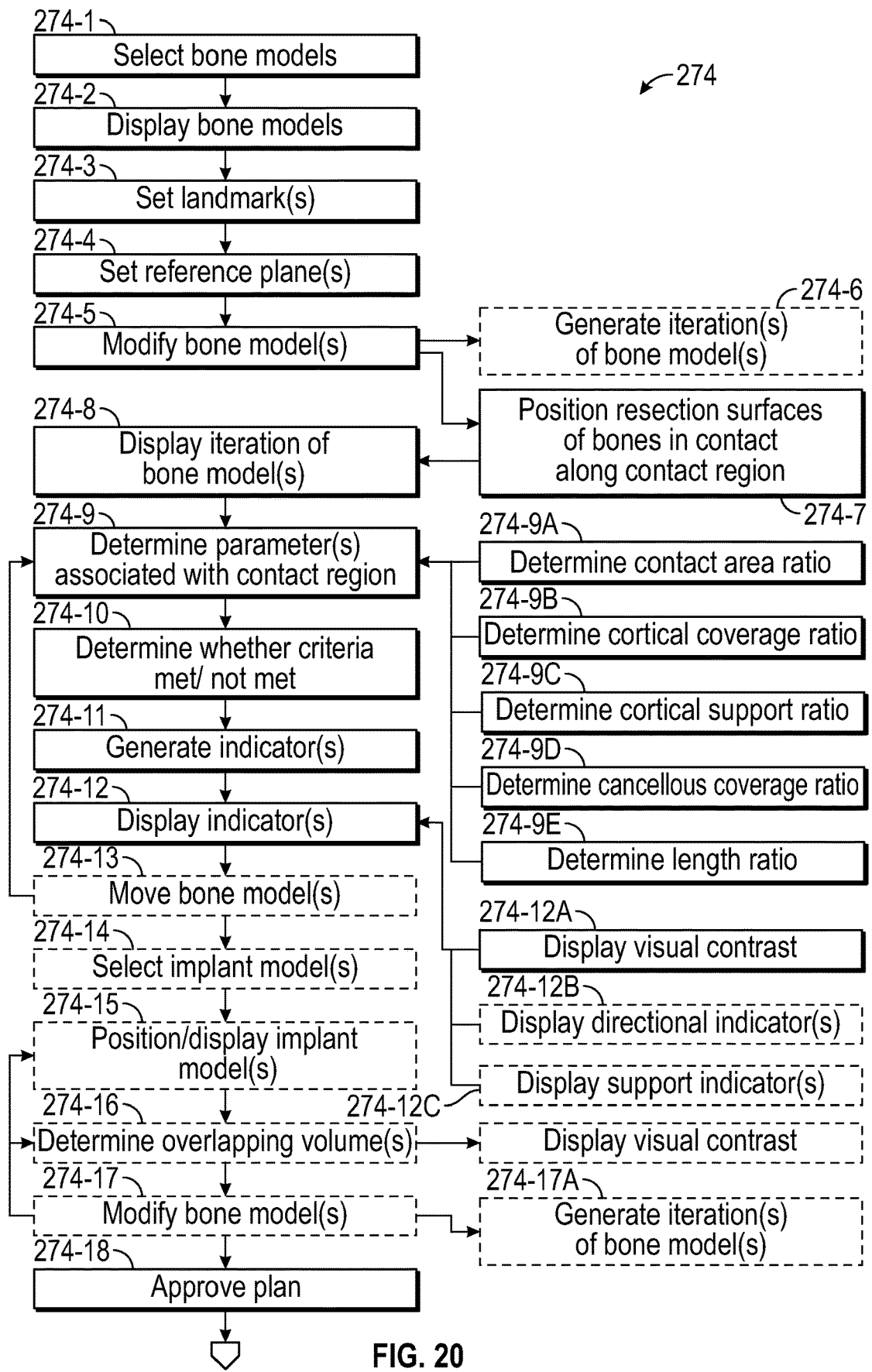
FIGS. 20-21 illustrate an exemplary method of planning an orthopaedic procedure.
Figure 21:
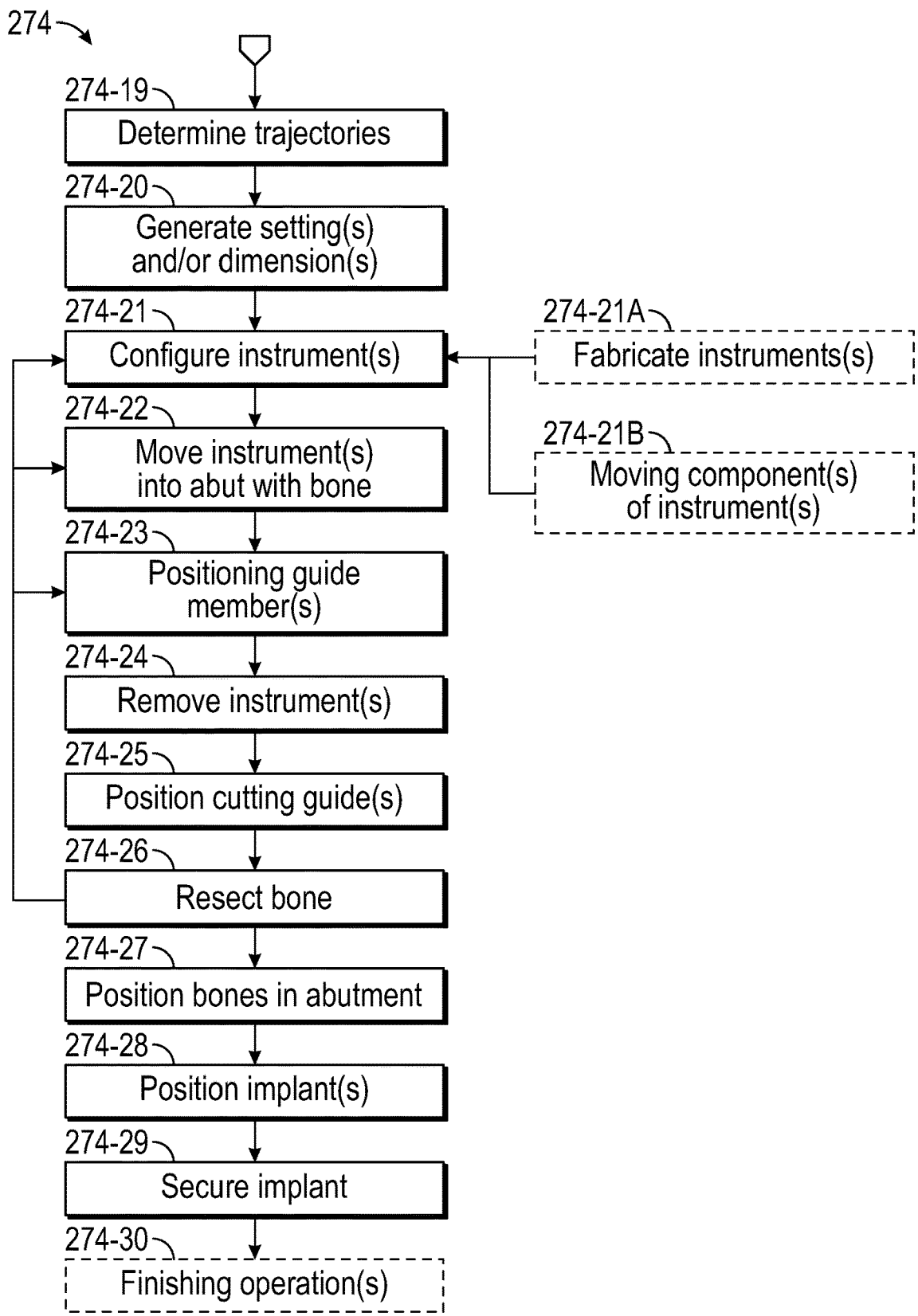

FIGS. 20-21 illustrates an exemplary method of planning and performing an orthopaedic procedure in a flowchart 274. The method 274 may be utilized to pre-operatively plan and perform an arthroplasty for restoring functionality to ankles, shoulders, knees, hips and other joints having advanced cartilage disease, for example. The method 274 may be utilized with any of the instrumentation and orthopedic implants disclosed herein, including the trajectory assembly 250 and secondary guides 254, 354. The method 274 may be utilized to determine whether sufficient contact area may be established between resected bone surfaces to promote fusion of adjacent bones, and may be utilized to configure one or more instruments for performing an orthopaedic procedure according to an associated surgical plan for a patient. Fewer or additional steps than are recited below could be performed within the scope of this disclosure, and the recited order of steps is not intended to limit this disclosure. Reference is made to the system 120 and user interface 142 for illustrative purposes.

Referring to FIGS. 2-3, with continuing reference to FIG. 20, at step 274-1 a first bone model 129-1 and a second bone model 129-2 may be selected from a plurality of bone models 129. The models 129-1, 129-2 may be selected in response to user interaction with the menu 146M associated with the first display window 144-1 or another portion of the user interface 142. The second bone model 129-2 may be associated with a long bone such as a tibia. The first bone model 129-1 may be associated with an adjacent bone, such as a talus or an adjacent long bone.

At step 274-2, the first and second bone models 129-1, 129-2 may be displayed in the graphical user interface 142 such that a first articular surface AS1 of the first bone model 129-1 opposes and contacts a second articular surface AS2 of the second bone model 129-2, as illustrated in the first display window 144-1. The bone models 129-1, 129-2 may be displayed in the user interface 142 such that the first articular surface AS1 opposes, but is spaced apart from, the second articular surface AS2, as illustrated in the second display window 144-2.

At step 274-3, one or more landmarks L may be set or otherwise indicated, as illustrated in the second display window 144-2. The landmarks L may be set automatically by the system 120 and/or in response to user interaction with the menu 146M associated with the second display window 144-2, direct interaction with the second display window 144-2 and/or another portion of the user interface 142.

Referring to FIG. 4, with continuing reference to FIG. 20, at step 274-4 one or more reference planes REF may be set or otherwise indicated relative to the bone models 129-1, 129-2. Step 274-4 may include setting or otherwise indicating a (e.g., first) reference plane REF (e.g., REF5-REF8) in the user interface 142 to establish the first resection surface S1 of the first bone model 129-1. Step 274-4 may include setting or otherwise indicating a (e.g., second) reference plane REF (e.g., REF1-REF4) in the user interface 142 to establish the second resection surface S2 of the second bone model 129-2. The reference planes REF may be set in response to user interaction with the menu 146M associated with the third display window 144-3, direct interaction with the third display window 144-3 and/or another portion of the user interface 142. The user may specify an offset distance or resection depth utilizing the entry field 146E.

At step 274-5, one or more of the bone models 129-1, 129-2 may be modified. The modification may be applied to a local copy of the bone models 129-1, 129-2 and/or a global copy of the bone models 129-1, 129-2 in the database 128. Step 274-5 may include generating at least one (e.g., first) iteration of first and second (e.g., resection) bone models 129-1', 129-2' at step 274-6. The bone models 129-1', 129-2' may exclude respective volumes of the bone models 129-1, 129-2 between the reference planes REF and articular surfaces AS1, AS2 of the bone models 129-1, 129-2, as illustrated in the fourth display window 144-4.

At step 274-7, the first resection surface S1 of the first bone model 129-1' may be positioned in contact with the second resection surface S2 of the second bone model 129-2' to establish a contact region CR. At step 274-8, at least portions of the bone models 129-1', 129-2' along the contact region CR may be displayed in the graphical user interface 142.

The method 274 may determine various characteristics associated with the contact region CR. In implementations, the method 274 may be utilized to determine whether or not sufficient contact area along the contact region CR may be established between resected bone surfaces S1, S2 to promote fusion of adjacent bones associated with the bone models 129-1', 129-2'.

At step 274-9, one or more parameters associated with the contact region CR and resection surfaces S1, S2 may be determined. The parameters may include any of the disclosed parameters and may be determined utilizing any of the techniques disclosed herein. In implementations, step 274-9 may include determining a contact area ratio CAR at step 274-9A, determining a cortical coverage ratio COR at step 274-9B, determining a cortical support ratio CSR at step 274-9C, determining a cancellous coverage ratio CCR at step 274-9D, and/or determining a length ratio D2:D1 at step 274-9E. Steps 274-9A to 274-9E may be performed utilizing any of the techniques disclosed herein.

Referring to FIGS. 5-6, with continuing reference to FIG. 20, the contact area ratio CAR, cortical coverage ratio COR and/or cancellous coverage ratio CCR may be associated with the first and second resection surfaces S1, S2 along the contact region CR. The length ratio D2:D1 may be associated with one of the bone models, such as the second bone model 129-2, as illustrated in FIG. 11.

Determining the contact area ratio CAR at step 274-9A may include determining a first area A1 of the first resection surface S1 along the contact region CR and determining a second area A2 of the second resection surface S2.

Determining the cortical coverage ratio COR at step 274-9B may include determining a first cortical area CO1 along the first resection surface S1. The first cortical area CO1 may be associated with cortical bone. Step 274-9B may include determining a second cortical area CO2 along the second resection surface S2. The second cortical area CO2 may be associated with cortical bone. The first cortical area CO1 may be less than, or may otherwise differ from, the second cortical area CO2. Step 274-9B may include determining an area of overlap between the first and second cortical areas CO1, CO2 along the contact region CR.

Determining the cortical support ratio CSR at step 274-9D may include determining a cortical area CO1/CO2 and a respective boundary area CB1/CB2. Step 274-9D may include determining a cortical support ratio CSR for the first bone model 129-1 and/or the second bone model 129-2. The cortical support ratio CSR may be associated with cortical-to-cortical bone contact.

Determining the cancellous coverage ratio CCR at step 274-9D may include determining a first cancellous area CA1 along the first resection surface S1. The first cancellous area CA1 may be associated with cancellous bone. Step 274-9C may include determining a second cancellous area CA2 along the second resection surface S2. The second cancellous area CA2 may be associated with cancellous bone. The first cancellous area CA1 may be less than, or may otherwise differ from, the second cancellous area CA2. Step 274-9C may include determining an area of overlap between the first and second cancellous areas CAL CA2 along the contact region CR.

Referring to FIG. 11, with continuing reference to FIG. 20, determining the length ratio D2:D1 at step 274-9E can include determining a first distance D1 along a longitudinal axis LA between a first end 129A and a second end 129B of a bone model 129, such as the second bone model 129-2. Step 274-9E can include determining a second distance D2 along the longitudinal axis LA between the a (e.g., second) reference plane REF and the second end 129B of the bone model 129, such as the second bone model 129-2.

At step 274-10, the method 274 may include determining whether or not one or more predetermined criteria are met and/or are not met. The predetermined criteria can include any of the predetermined criteria disclosed herein. Determining whether or not the predetermined criteria are met or are not met may be determined utilizing any of the techniques disclosed herein, including comparing values of the contact area ratio CAR, cortical coverage ratio COR, cortical support ratio CSR, cancellous coverage ratio CCR and/or length ratio D2:D1 to one or more predefined thresholds. The predefined thresholds can include any of the predefined thresholds disclosed herein. Each predefined threshold may be set based on patient characteristics such as height and limb length and may be specified in the surgical plan 131.

The predetermined criteria can include the contact area ratio CAR meeting a predefined threshold. In implementations, the predetermined criteria can include the contact area ratio CAR being greater than or equal to a first predefined threshold. The first predefined threshold may include any of the values disclosed herein. The first predefined threshold may be greater than or equal to 0.4, more narrowly greater than or equal to 0.5. The first predefined threshold may be greater than or equal to 0.75, or more narrowly equal to 1.0.

The predetermined criterion can include the cortical coverage ratio COR meeting a predefined threshold. In implementations, the predetermined criteria can include the cortical coverage ratio COR being greater than or equal a second predefined threshold. The second predefined threshold may include any of the values disclosed herein. The second predefined threshold may be greater than or equal to 0.03, or more narrowly greater than or equal to 0.05.

The predetermined criteria can include the cancellous coverage ratio CCR meeting a predefined threshold. In implementations, the predetermined criteria can include the cancellous coverage ratio CCR being greater than or equal to a third predefined threshold. The third predefined threshold may include any of the values disclosed herein. The third predefined threshold may be greater than or equal to 0.75, more narrowly greater than or equal to 0.90, or even more equal to 1.0.

The predetermined criteria can include the length ratio D2:D1 meeting a (e.g., fourth) predefined (e.g., length) threshold. The fourth predefined threshold may include any of the values disclosed herein. In implementations, the fourth predefined threshold may be less than or equal to 0.05, or more narrowly less than or equal to 0.01.

The predetermined criteria can include the contact to resection ratio CRR meeting a fifth predefined threshold. The fifth predefined threshold may include any of the values disclosed herein. In implementations, the fifth predefined threshold may include a contact to resection ratio CRR greater than or equal to 0.75, more narrowly greater than or equal to 0.90, or even more narrowly equal to 1.0.

The predetermined criteria can include the cortical support ratio CSR meeting a sixth predefined threshold. The sixth predefined threshold may include any of the values disclosed herein. In implementations, the sixth predefined threshold may include a cortical support ratio CSR greater than or equal to 0.50, more narrowly greater than or equal to 0.75, more narrowly greater than or equal to 0.90, or even more narrowly equal to 1.0.

At steps 274-11 and 274-12, the method 274 may include generating and displaying at least one or more indicator PI in the user interface 142 in response to one or more predetermined criteria being met and/or not met. The status of each indicator PI may be individually set and/or updated. Step 274-11 may include generating one or more indicators PI in response to one or more predetermined criteria being met and/or not met. In implementations, a status of the indicator PI may be set based on whether or not the respective predetermined criteria are met or are not met. Step 274-12 may include displaying at least one or more indicators PI in the user interface 142 associated with the contact area ratio CAR in response to one or more of the predetermined criteria being met.

The indicators PI can include a value of the contact area ratio CAR determined at step 274-9A, a value of the cortical coverage ratio COR determined at step 274-9B, and/or a value of the cancellous coverage ratio CCR determined at step 274-9D, as illustrated by the graphic 146G of FIG. 5. The indicators PI can include a value of the cortical support ratio CSR determined at step 274-9C, as illustrated by the indicator PVC of FIG. 6. The indicators PI can include a value of the length ratio D2:D1 determined at step 274-9E, as illustrated by indicator PVL in FIGS. 5-6 and 8.

Step 274-12 may include displaying a visual contrast between the contact region CR and a remainder of the first and second resection surfaces S1, S2 that excludes the contact region CR at step 274-12A, as illustrated by respective graphics R1, R2 in FIG. 7. Step 274-12A may include displaying a visual contrast between portions of the contact region CR associated with cortical bone and cancellous bone, illustrated by respective graphics R1A, R1B in FIG. 7.

Step 274-12 may include displaying one or more indicators PI associated with the localized support regions LSR at step 274-12C, such as the support indicators PP1-PP4 of FIGS. 9-10. The support indicators PP1-PP4 may be associated with respective localized support regions LSR1-LSR4.

Referring to FIG. 8, with continuing reference to FIG. 20, determining the contact area ratio CAR at step 274-9A may include determining a set of values of the contact area ratio CAR associated with different positions of the first resection surface S1 relative to the second resection surface S2 along the contact region CR, with values in the set of values of the contact area ratio CAR corresponding to respective directions along the contact region CR. Each value may be associated with a respective vector or coordinate along the resection surface S1/S2 such that values may be determined for substantially all relative positions between the bone models 129-1', 129-2' in which contact between the resection surfaces S1, S2 is maintained. Step 274-9A may include determining a maximum value of the set of values of the contact area ratio CAR in which contact is maintained between the resection surfaces S1, S2.

Step 274-12 may include displaying one or more directional indicators DA at step 274-12B, as illustrated in the seventh display window 144-7. The directional indicators DA may be associated with the respective values of the contact area ratio CAR determined at step 274-9A. The directional indicators DA may include a (e.g., first) directional indicator DA-1 associated with a maximum value of the set of values of the contact area ratio CAR determined at step 274-9A. Step 274-12B may include displaying the directional indicator DA-1 relative to the contact region CR.

At step 274-13, the first and second bone models 129-1', 129-2' may be moved relative to each other based on the one or more indicators PI. Step 274-12 may include moving the first bone model 129-1' in a second direction DIR2 relative to the first bone model 129-2' along the contact region CR. The second direction DIR2 may be substantially aligned with a direction corresponding to the first directional indicator DA-1. Step 274-13 may include moving the first and second bone models 129-1, 129-2 relative to each other to increase or otherwise vary the cortical support ratio CSR and/or quantity of localized support regions LSR in which contact is established between the cortical boundary areas CB1, CB2, as illustrated by FIGS. 9-10. Determining one or more parameters associated with the resection surfaces S1, S2 and contact region CR may be repeated or updated at step 274-9, including steps 274-9A, 274-9B, 274-9C, 274-9D and/or 274-9E, in response to relative movement between the bone models 129-1', 129-2' at step 274-13.

Referring to FIGS. 2 and 12, with continuing reference to FIG. 20, at step 274-14 one or more implant models 130 may be selected from a plurality of implant models 130. The implant model(s) 130 may be selected automatically based on various attributes of the patient including the selected bone models 129 and/or in response to user interaction with the menu 146M adjacent to the display windows 144-8 to 144-10 and/or another portion of the user interface 142. The implant models 130 can include any of the implants disclosed herein.

At step 274-15, the selected implant model(s) 130 may be positioned relative to the first and/or second bone models 129-1', 129-2', which may occur subsequent to establishing the contact region CR at step 274-7. The selected implant model(s) 130 may be displayed in the user interface 142. One or more iterations of moving the bone models 129-1', 129-2' relative to each other at step 274-13 may occur prior to, during and/or subsequent to positioning the implant model(s) 130 at step 274-15.

The method 274 may determine a relative fit between the selected implant model(s) 130 and the bone models 129-1', 129-2' at the specified position. At step 274-16, one or more overlapping volumes between the selected implant model(s) 130 and the bone models 129-1', 129-2' may be determined. The overlapping volumes may be determined utilizing any of the techniques disclosed herein. Step 274-16 may include moving the selected implant model(s) 130 relative to the bone models 129-1', 129-2', and then repeating the determination of any overlapping volumes for the respective position.

At step 274-12A, one or more indicators may be displayed based on the overlapping volumes together with the selected implant model(s) 130. Step 274-12A may include displaying a visual contrast between the overlapping volume(s) and a remainder of the volumes of the bone models 129-1', 129-2' that excludes the overlapping volume(s). In implementations, the visual contrast may be established by one or more visual indicators VI applied to the overlapping volumes (shown in hatching in FIGS. 12-13 for illustrative purposes).

Referring to FIG. 13, with continuing reference to FIGS. 12 and 20, one or more of the bone models 129-1', 129-2' may be modified at step 274-17. Step 274-17 may include generating an (e.g., second) iteration of the first and/or second bone models 129-1", 129-2" that excludes the overlapping volumes at step 274-17A.

The method 274 may include repeating step 274-16 to determine any overlapping volumes for each iteration of the first and/or second bone models 129-1", 129-2" relative to the selected implant(s) 130. The method 274 may include repeating step 274-15 to move and/or display the selected implant model(s) 130 for each subsequent iteration of the first and second bone models 129-1", 129-2". Repeating step 274-15 may include adjusting a position of the selected implant(s) 130 in response to user interaction with the menu 146M, directly with one of the display windows 144-8 to 144-12, and/or another portion of the user interface 142. Step 274-17 may be repeated until any overlapping volumes are eliminated or otherwise reduced. Utilizing the techniques disclosed herein, a relatively close fit can be established between the selected implant(s) 130 and adjacent surfaces of the bone models 129-1", 129-2", which can improve healing of the patient.

At step 274-18, the surgeon or another user can approve a surgical plan 131 (FIG. 2). The surgical plan 131 can include any of the parameters established in the method 274, including the landmarks L associated with the bone models 129-1, 129-2, the bone models 129-1/129-1'/129-1", 129-2/129-2'/129-2", the specified resection planes REF associated with the resection surfaces S1, S2, selected implant model(s) 130, and/or overlapping volumes that may indicate relief cut(s) to accommodate an implant.

Referring to FIG. 21, with continuing reference to FIG. 20, the method 274 may include one or more steps to implement each surgical plan 131. Referring to FIGS. 14-15, with continuing reference to FIG. 21, the method 274 may include determining one or more trajectories T associated with surgical device(s) at step 274-19, including any of the guide members disclosed herein such as a guide pin. The trajectories T may be associated with positions along the respective bone model 129-1', 129-2' relative to the contact region CR, which may be subsequently established by one or more resections. Step 274-19 may include determining a first trajectory T1 associated with a first guide pin GP-1 and a second trajectory T2 associated with a second guide pin GP-2 (see, e.g., FIG. 27). Step 274-19 may include determining a third trajectory T3 associated with a third guide pin GP-3 and a fourth trajectory T4 associated with a fourth guide pin GP-4 (see, e.g., FIG. 36). The first and second trajectories T1, T2 may be associated with respective first and second positions along one of the bone models 129-1', 129-2' relative to the contact region CR (FIG. 14), such as the first bone model 129-1'. The third and fourth trajectories T3, T4 may be associated with respective third and fourth positions along another one of the first and second bone models 129-1', 129-2' relative to the contact region CR (FIG. 14), such as the second bone model 129-2'.

Step 274-19 may occur in response to the contact area ratio CAR meeting one or more predefined thresholds and/or other predetermined criteria, including any of the predetermined criteria and thresholds disclosed herein. The positions of the trajectories T1/T3, T2/T4 may be established along a common one of the bone models 129-1/129-1', 129-2/129-2' adjacent the resection surface S1/S2. Although pairs of the trajectories T1/T3, T2/T4 are disclosed, it should be understood that the techniques disclosed herein can be utilized to establish a single trajectory or more than two trajectories associated with each bone model 129-1/129-1', 129-2/129-2'.

One or more settings and/or dimensions for surgical instrument(s) may be generated at step 274-20. The setting(s) and dimension(s) may be associated with a trajectory assembly and/or another surgical instrument based on the trajectories T1, T2, T3 and/or T4 associated with at least one, or each, of the bone models 129-1/129-1', 129-2/129-2'. The trajectory assemblies can include any of the trajectory assemblies disclosed herein, such as the trajectory assembly 250. The settings generated at step 274-20 can be stored in a surgical plan 131 (FIG. 2). Exemplary settings include patient information, procedure type, implant type and position, fastener sizes and lengths, resection depths and angles, targeting guide and secondary guide positions, secondary guide aperture selections, arm member lengths and positions relative to the surgical site, relief cut locations and depths, guide member trajectories and insertion points, etc.

At step 274-21, one or more surgical instruments can be configured according to the setting(s) and dimension(s) generated at step 274-20. Step 274-21 may include configuring the surgical instrument(s) according to any of the techniques disclosed herein. Step 274-21 may include fabricating surgical instrument(s) at step 274-21A according to the dimension(s) generated at step 274-20. The fabricated instrument(s) may include one or more patient-specific surfaces or components.

Figure 22:
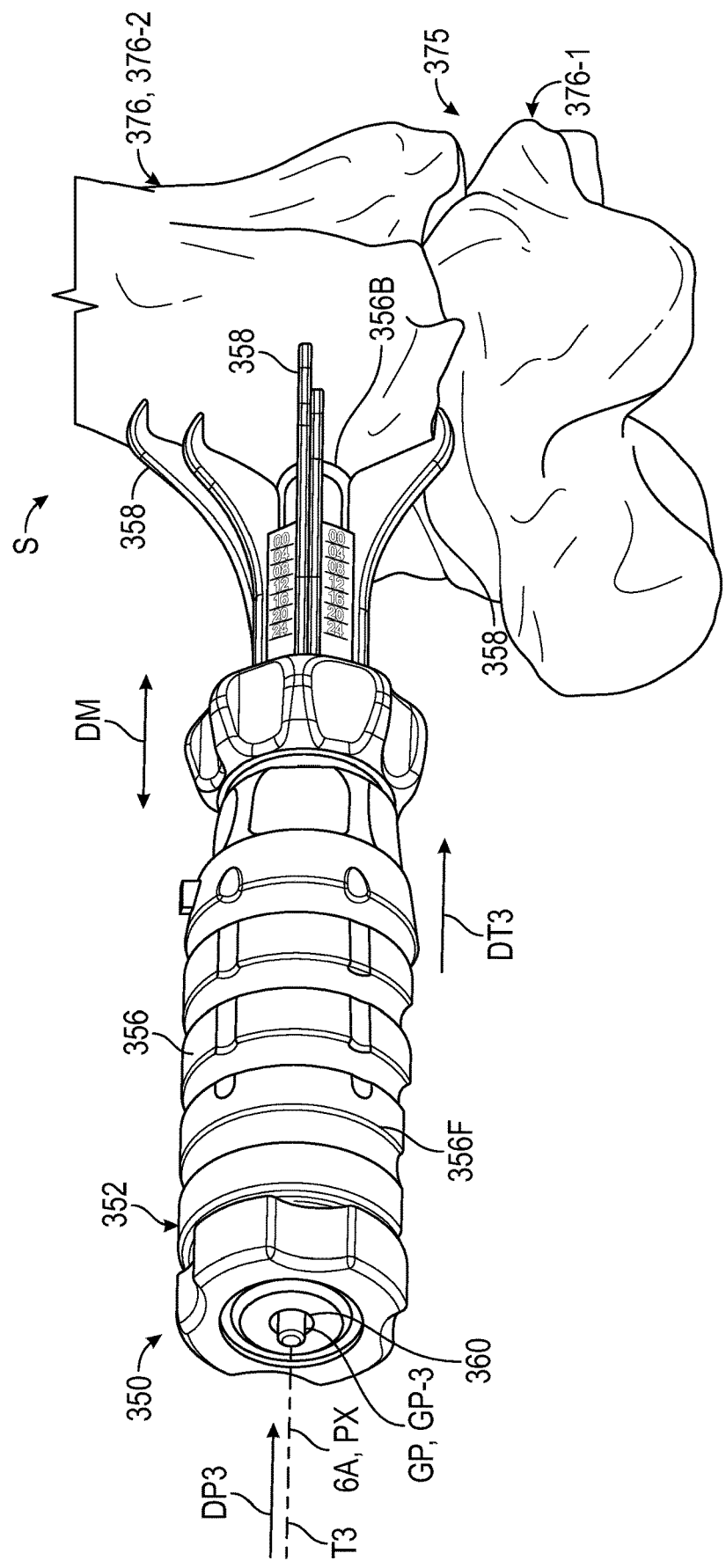
FIG. 22 illustrates a perspective view of an exemplary trajectory assembly positioned relative to adjacent bones.

Referring to FIG. 22, with continuing reference to FIGS. 21, step 274-21 may include moving component(s) of the instrument(s) at step 274-21B according to the setting(s) generated at step 274-20. The instrument may include a trajectory assembly 350. The trajectory assembly 350 may include a trajectory guide 352 and a secondary guide 354 coupled to the trajectory guide 352.

Step 274-21 may include configuring the trajectory guide 352 and/or secondary guide 354 (FIG. 25) according to the setting(s) to establish the predetermined trajectories T. The third and fourth trajectories T3, T4 in FIGS. 22-24 may correspond to the trajectories T3, T4 of FIGS. 14-15, and the first and second trajectories T1, T2 in FIGS. 25-27 may correspond to the trajectories T1, T2 of FIGS. 14 and 16.

The trajectory assembly 350, including the secondary guide 354 and secondary guide 354, may be configured utilizing any of the techniques disclosed herein. Step 274-21B may include moving one or more of arm members 358 from a first position to a second position relative to a guide body 356 of the trajectory guide 352 to establish the trajectory T3, which may be established along the passage axis PX. Step 274-21B may include moving the arm members 358 relative to the guide body 356 to respective positions according to the setting(s). The arm members 358 may be moved in a direction DM relative to a longitudinal axis GA of the guide body 356.

At step 274-22, the instrument(s) may be moved into abutment with one or more bones 376 at the surgical site S. The bones 376 can include a first bone 376-1 and a second bone 376-2 that cooperate to establish a joint 375. The second bone 376-2 may be a long bone such as a tibia. The first bone 376-1 may be an adjacent bone such as a talus. The first and second bones 376-1, 376-2 may be associated with respective ones of the selected bone models 129-1, 129-2 (FIG. 3).

Step 274-22 may include moving the trajectory guide 352 in a direction DT3 and into abutment with one of the bones 376 to set the trajectory T3 of the guide pin GP-3 relative to tissue including one of the bones 376 such as the bone 376-2. Step 274-22 may occur such that surfaces of the arm members 358 abut predetermined positions of the bone 376-2 according to the setting(s) and associated surgical plan 131 (FIG. 2), as illustrated in FIGS. 22-24.

At step 274-23, one or more guide members may be positioned with the trajectory assembly 350, such as one or more guide pins GP. The instruments including the trajectory assembly 350 (and assembly 450, see FIG. 32) may be configured such that the corresponding guide pin GP trajectories and insertion points are established relative to the bones 376 to ensure resections substantially conform to the surgical plan 131, including specified resection depths and positions.

Step 274-23 may include positioning the guide pin GP-3 through the guide passage 360 and then into the bone 376-2 with the trajectory guide 352 according to the associated (e.g., third) trajectory T3 (see, e.g., FIGS. 14-15) specified by one or more parameters in the surgical plan 131. The third guide pin GP-3 may be moved in a direction DP3 such that the guide pin GP-3 is at least partially received in and through the guide passage 360 of the guide body 356 along the passage axis PX to establish the trajectory T3.

The secondary guide 354 may be moveable relative to the longitudinal axis GA of the trajectory guide 352. The secondary guide 354 may be positioned prior to, during and/or subsequent to positioning the trajectory guide 352 at a surgical site S. Step 274-21 may include moving a secondary guide 354 relative to the guide body 356 of the trajectory guide 352 according to the setting(s). Step 274-21 may include setting a position of the secondary guide 354 relative to the longitudinal axis GA to establish the fourth trajectory T4 relative to the third trajectory T3.

Figure 25:
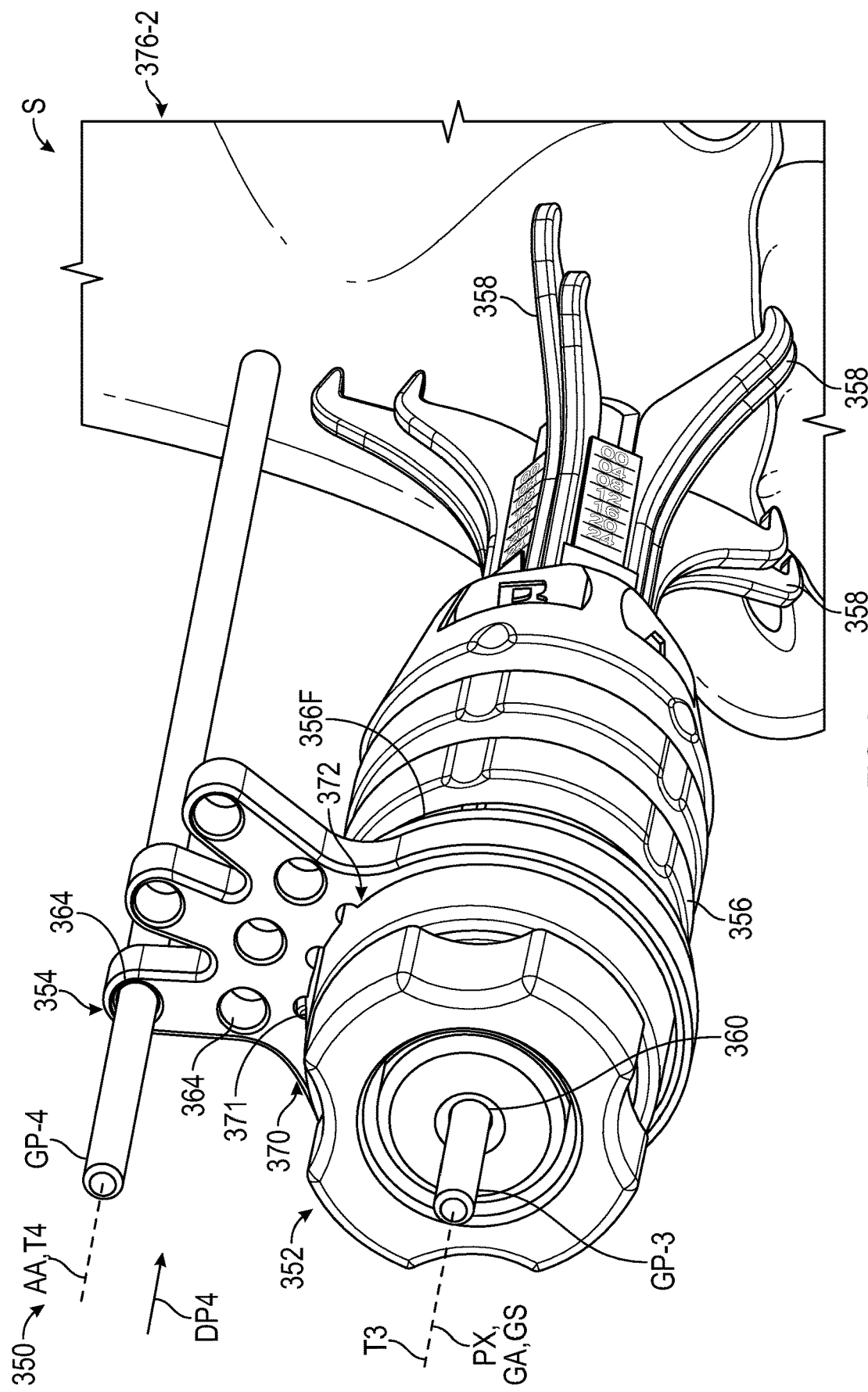
FIG. 25 illustrates a perspective view of a secondary guide coupled to the trajectory assembly of FIG. 22.

Step 274-21 may include moving the secondary guide 354 in a direction RD1 (FIG. 26) about the longitudinal axis GA of the guide body 356 according to the setting(s). A main body 362 of the secondary guide 354 may be rotated or otherwise moved relative to the longitudinal axis GA such that aperture(s) 364 move from a first circumferential position to a second circumferential position relative to the longitudinal axis GA. A relative orientation or position of the trajectory guide 352 and secondary guide 354 may be set in response to engagement between first and second interface features 371, 372 at an interface 370. The guide body 356 may include a guide passage 360 extending along a passage axis PX. The secondary guide 354 may be coupled to the guide body 356 of the trajectory guide 352 to establish the trajectory T4, which may be along an aperture axis AA of one or more apertures 364 of the secondary guide 354. The secondary guide 354 may be coupled to the guide body 356 such that the aperture axis AA is offset from the passage axis PX, as illustrated in FIGS. 25-26. Relative positioning between the secondary guide 354 and trajectory guide 352 may provide the surgeon with greater flexibility in positioning the guide pins GP at trajectories that closely approximate the surgical plan 131.

Referring to FIGS. 25-26, step 274-23 may include positioning the fourth guide pin GP-4 into the bone 376-2 with the trajectory guide 352 according to the associated (e.g., fourth) trajectory T4 (see, e.g., FIGS. 14-15) specified by one or more parameters in the surgical plan 131. The guide pin GP-4 may be moved in a direction DP4 such that the guide pin GP-4 at least partially received in and through a selected one of the apertures 364 along the respective aperture axis AA to establish the fourth trajectory T4. Step 274-23 may occur such that the guide pins GP-3, GP-4 are substantially parallel to each other subsequent to inserting the guide pins GP-4, GP-4 in the bone 376-2. Placement of the guide pin GP-4 relative to the guide pin GP-3 may be utilized to substantially establish alignment to the tibial axis (see, e.g., L2 of FIG. 3) and for subsequent placement of cutting guides.

Figure 28:
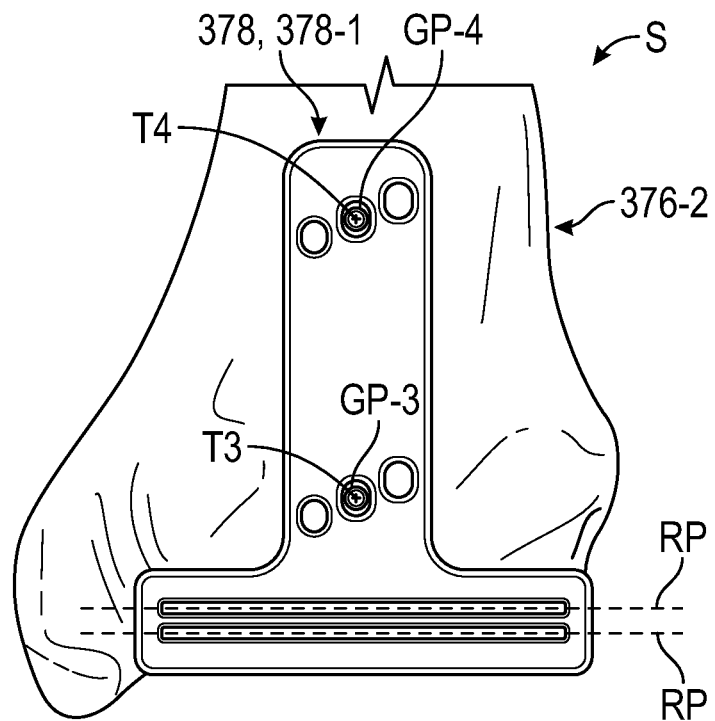
FIG. 28 illustrates side view of a cutting guide positioned relative to one of the bones of FIG. 25.
Figure 29:
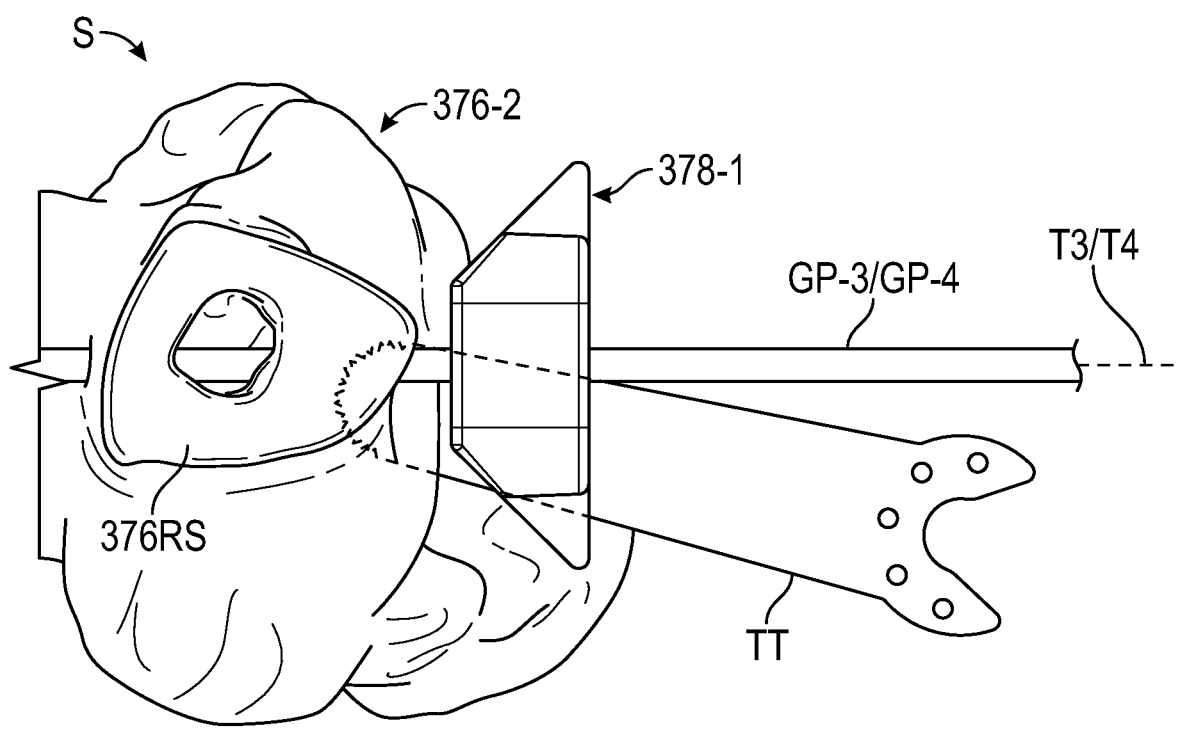
FIG. 29 illustrates an end view of the cutting guide of FIG. 28.

Referring to FIGS. 28-29, with continuing reference to FIG. 21, at step 274-24 the instrument(s) including the trajectory assembly 350 may be removed from the surgical site S. One or more cutting guides 378 may be positioned adjacent to the bone 376-2 relative to the surgical site S. The cutting guides 378 may be positioned according to the trajectories T3, T4 of the guide pins GP-3, GP-4. The cutting guides 378 can include a first cutting guide 378-1 and a second cutting guide 378-2 (FIG. 30) including one or more slots dimensioned to receive tooling TT such as a saw blade (FIG. 29). Step 274-25 may include positioning the first cutting guide 378-1 along the pins GP-3, GP-4. The first cutting guide 378-1 may establish one or more resection planes RP (shown in dashed lines in FIG. 28). Each resection plane RP may be associated with one of the specified reference planes REF of the respective bone model 129 (FIG. 4). The cutting guide 378-1 can include one or more apertures distributed at predetermined offsets for positioning the slots relative to the bone 376-2. Selection of the particular apertures may be specified in the surgical plan 131.

Figure 30:
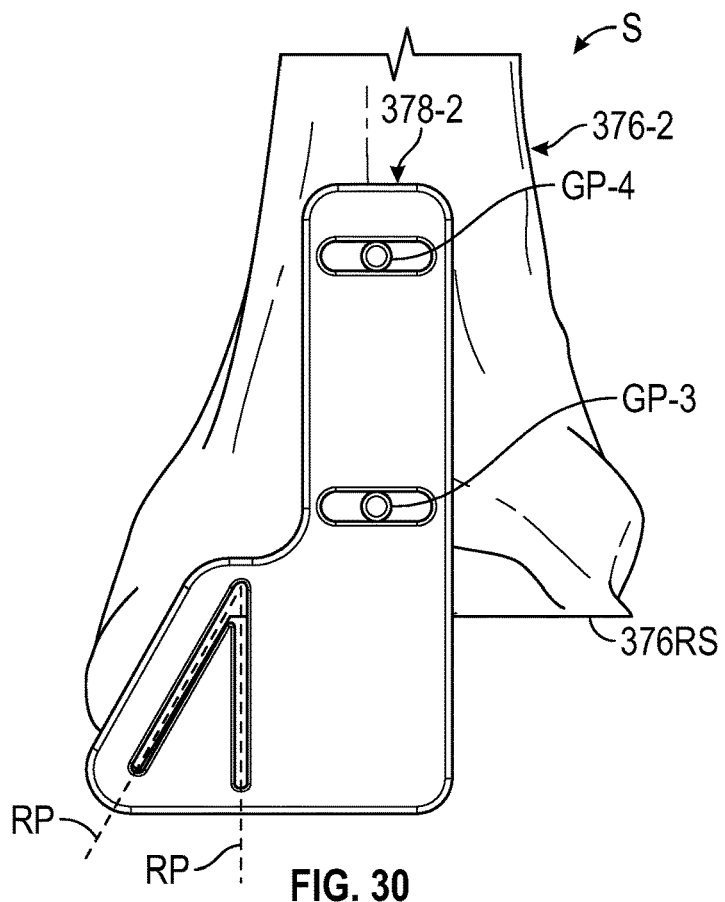
FIG. 30 illustrates side view of another cutting guide positioned relative to one of the bones of FIG. 28.
Figure 31:
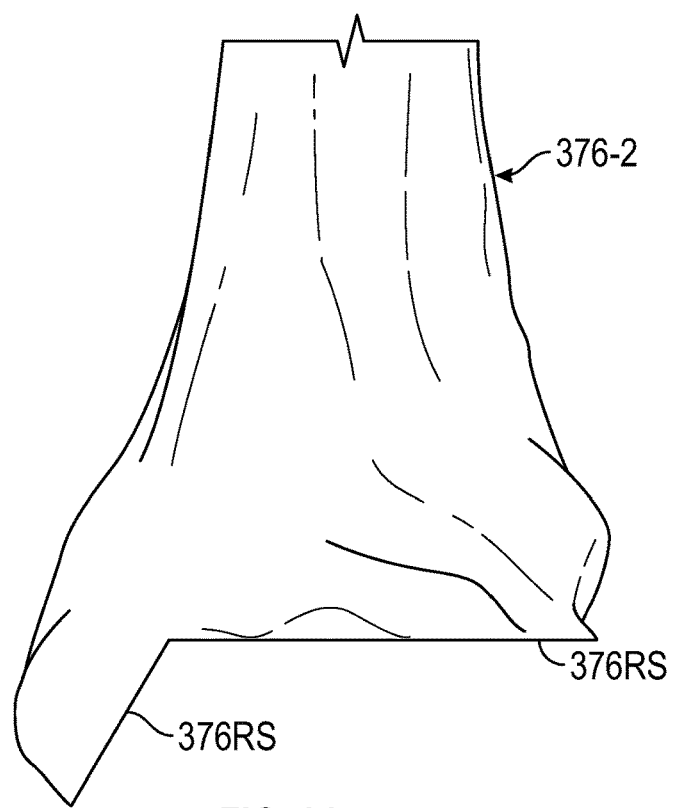
FIG. 31 illustrates resection surfaces of the bone of FIG. 28.

At step 274-26, a portion of the bone 376-2 may be resected along the resection plane RP to establish a resection surface 376RS of the bone 376-2, as illustrated in FIGS. 29-31.

Steps 274-24, 274-25 and/or 274-26 may be repeated to resect an additional portion of the bone 376-2. The second cutting guide 378-2 may be positioned along the guide pins GP-3, GP-4, as illustrated in FIG. 30, which may occur subsequent to removing the first cutting guide 378-1. The second cutting guide 378-2 may include slots or apertures dimensioned to receive the respective guide pins GP-3, GP-4. The slots may facilitate lateral movement of the second cutting guide 378-2. Another portion of the bone 376-2 may be resected along another resection plane RP to establish another resection surface 376RS of the bone 376-2, which may be transverse to the resection surface 376RS established with the first cutting guide 378-1, as illustrated in FIG. 31. The transverse cut established by the second resection surface 376RS may establish a "gutter cut" of a medial malleolus.

Figure 32:
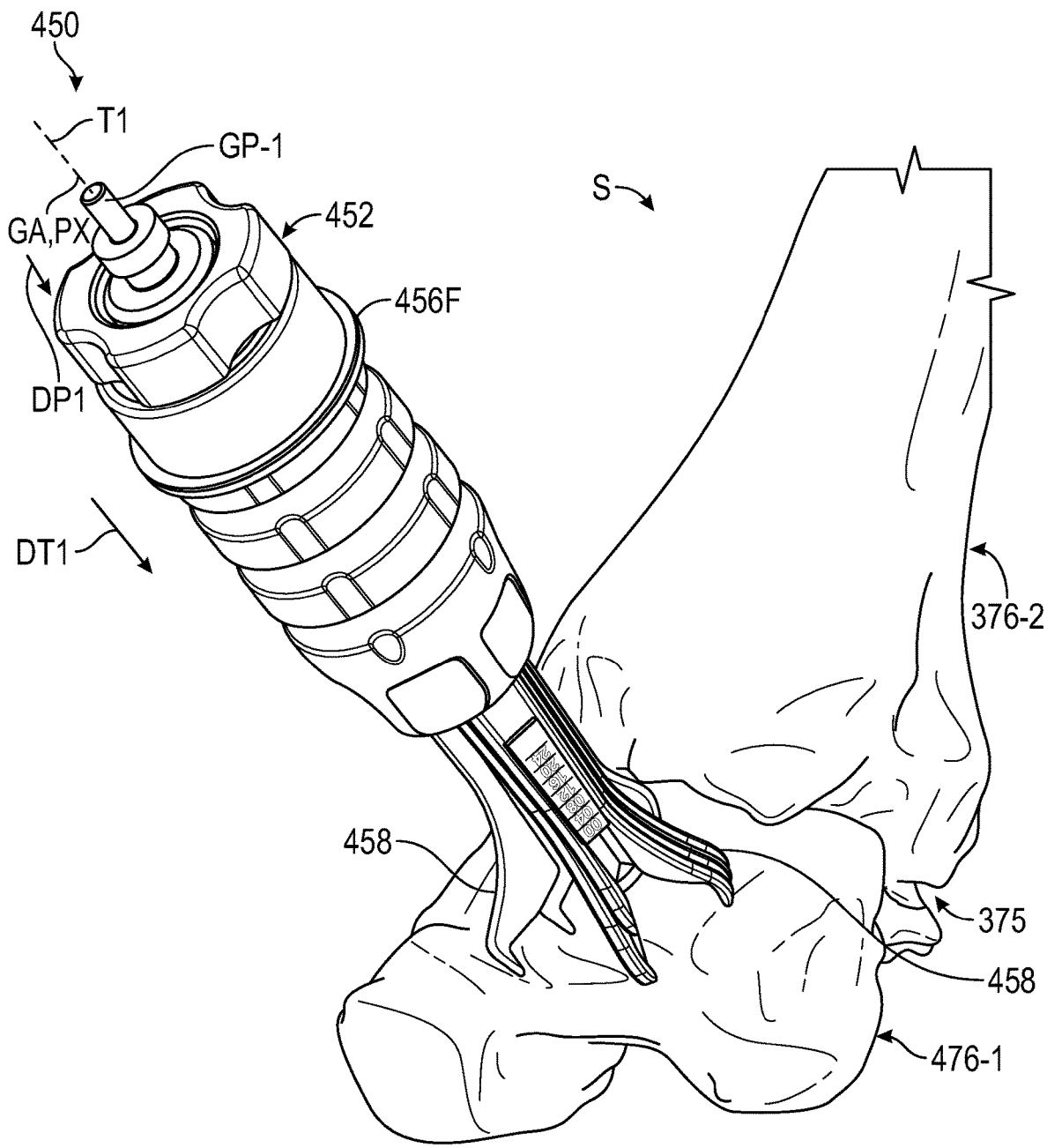
FIG. 32 illustrates a perspective view of another exemplary trajectory assembly positioned relative to adjacent bones.

A trajectory assembly 450 may be positioned at the surgical site S. Referring to FIG. 32, with continuing reference to FIG. 21, the trajectory assembly 450 can be the same or can differ from the trajectory assembly 350. The trajectory assembly 450 includes a trajectory guide 452 and a secondary guide 454 coupled to the trajectory guide 452 (FIGS. 25-26). The joint 375 may be placed in extension to facilitate positioning of the arm members 458 of the trajectory guide 452.

Figure 33:
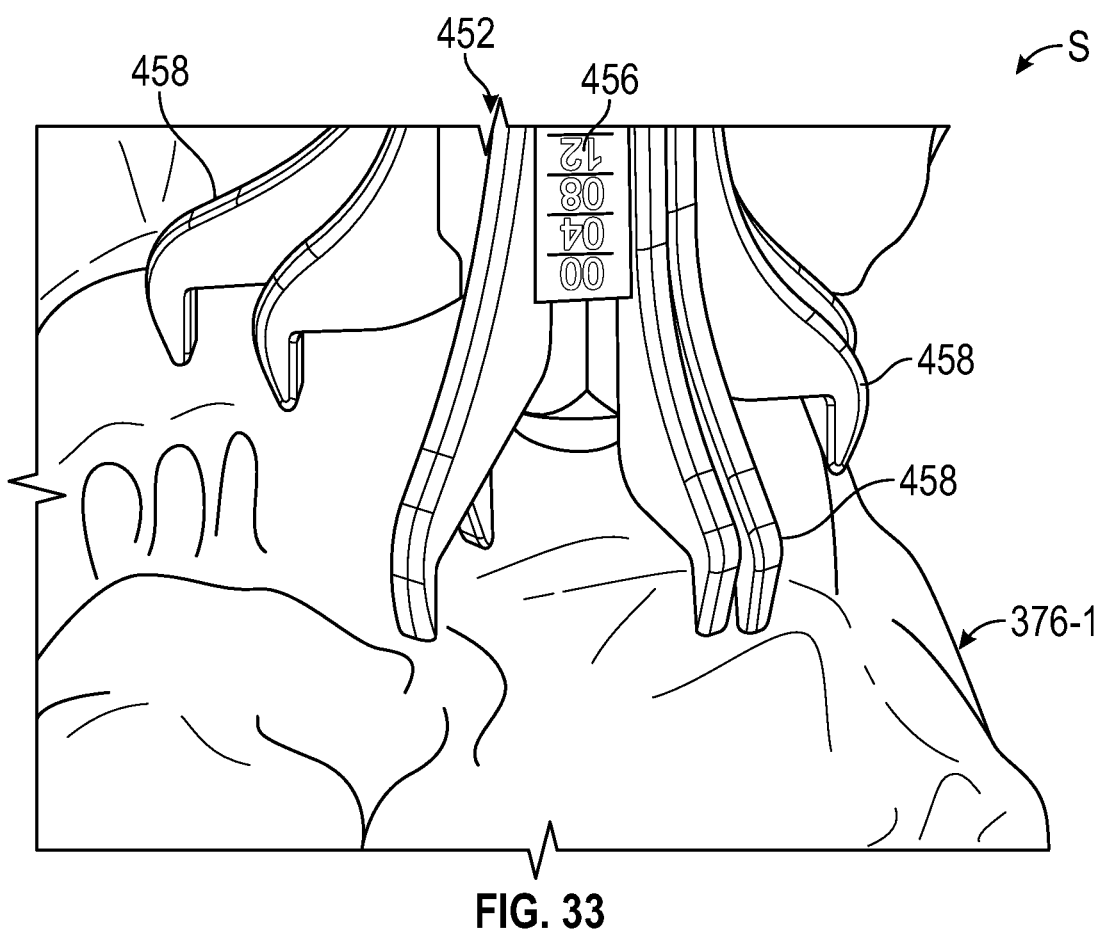
FIG. 33 illustrates a perspective view of arm members of the trajectory assembly of FIG. 32.

The trajectory guide 452 may be moved into abutment with the first bone 476-1 at step 274-22. Step 274-22 may include moving the trajectory guide 452 in a direction DT1 and into abutment with one of the bones 376 to set a trajectory of the guide pin GP-1 relative to tissue including one of the bones 376 such as the first bone 376-1. Step 274-22 may occur such that surfaces of the arm members 458 abut predetermined positions of the bone 376-1 according to the setting(s) and associated surgical plan 131 (FIG. 2), as illustrated in FIGS. 32-34. The configured positions of the arm members 458 relative to the guide body 456 that establish the trajectory T1 may be the same or may differ from the configured positions of the guide members 358 that establish the trajectory T3.

Figure 36:
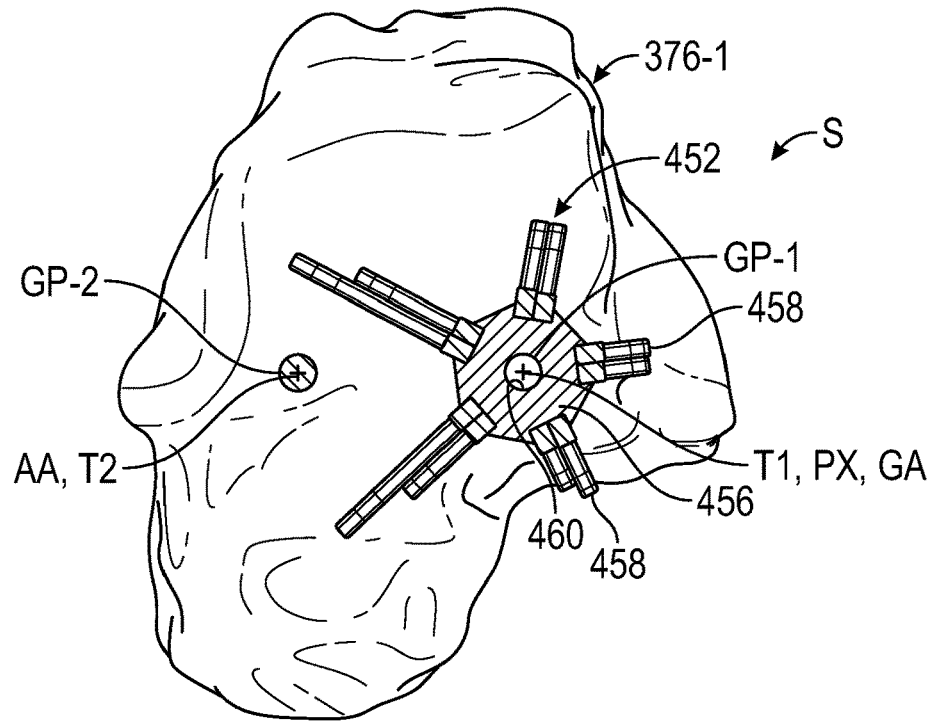
FIG. 36 illustrates a sectional view of the trajectory assembly of FIG. 35.

Referring to FIGS. 34-35, with continuing reference to FIG. 21, step 274-23 may include positioning one or more guide members with a trajectory assembly 450, including one or more guide pins GP. Step 274-23 may include positioning a first guide pin GP-1 into the bone 376-1 with the trajectory guide 452 according to the associated (e.g., first) trajectory T1 (FIGS. 35-36). The guide pin GP-1 may be moved in a direction DP1 such that the guide pin GP-1 is at least partially received in and through a guide passage 460 of the guide body 456 along the passage axis PX to establish the trajectory T1 (FIG. 35).

The secondary guide 454 can include one or more apertures 464. The apertures 464 can be distributed in a row 464-1 about a guide (e.g., longitudinal) axis GS, as illustrated in FIG. 35. The secondary guide 454 can be configured in the same manner as the secondary guide 354, including setting a relative orientation or position of the trajectory guide 452 and secondary guide 454 in response to engagement between first and second interface features 471, 472 at an interface 470.

Step 274-23 may include positioning a second guide pin GP-2 through a selected aperture 464 and then into the bone 376-1 with the secondary guide 454 according to the associated (e.g., second) trajectory T2 (FIG. 35). The guide pin GP-2 may be moved in the direction DP2 such that the guide pin GP-2 is at least partially received in and through a selected one of the apertures 464 along a respective aperture axis AA to establish the trajectory T2 (FIGS. 35-36). Step 274-23 may occur such that the guide pins GP-1, GP-2 are substantially parallel to each other subsequent to inserting the guide pins GP-1, GP-2 in the bone 376-1.

Figure 37:
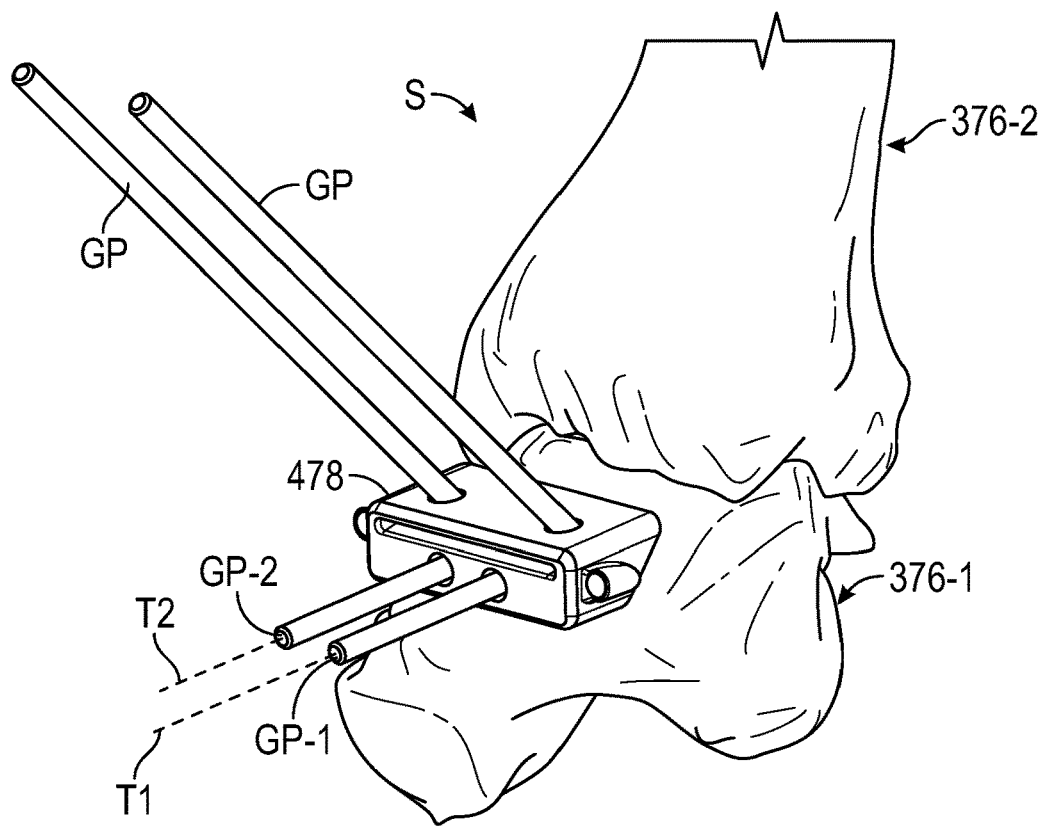
FIG. 37 illustrates a perspective view of a cutting guide positioned relative to one of the bones of FIG. 34.
Figure 38:
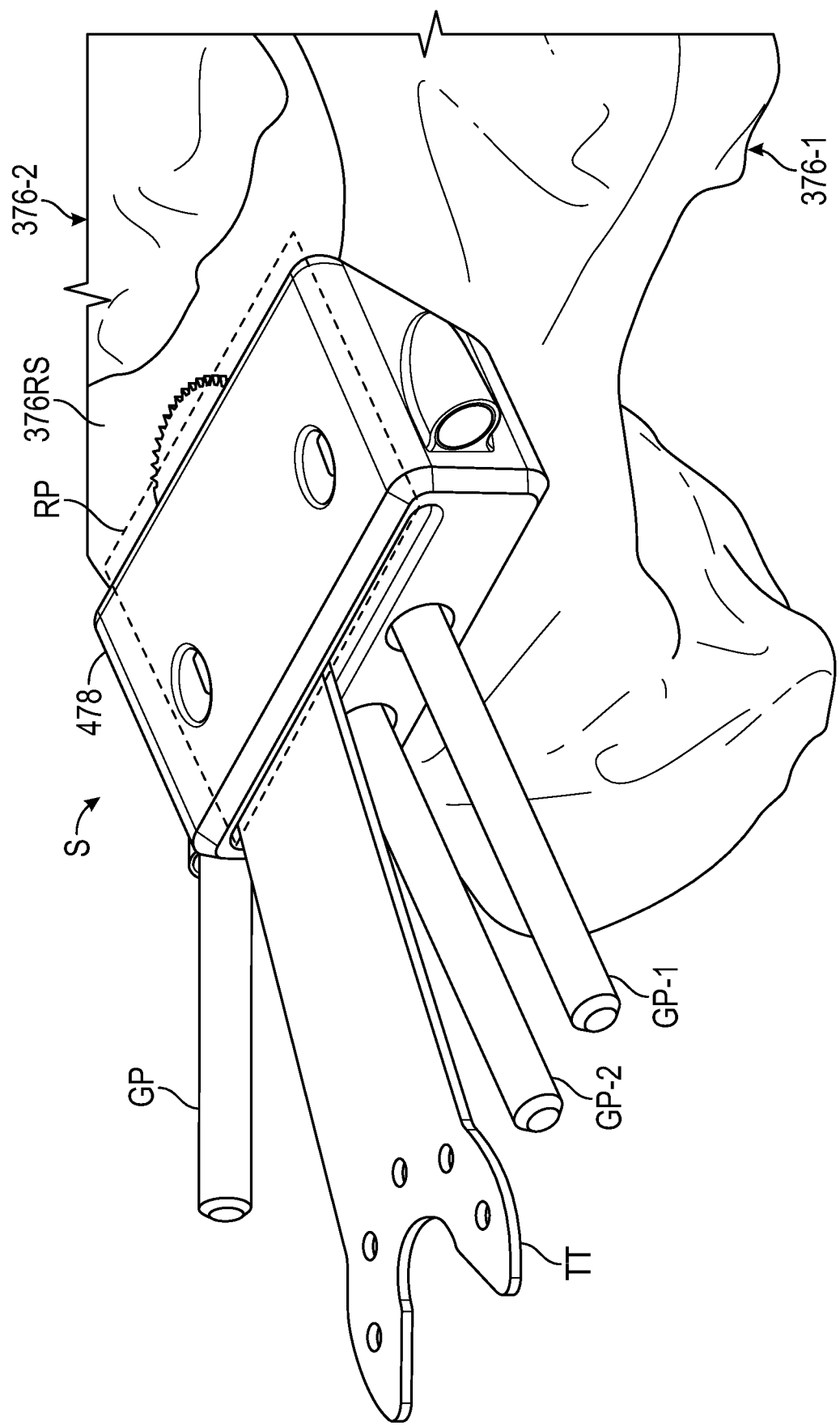
FIG. 38 illustrates a perspective view of the cutting guide of FIG. 37 and a resection.

Referring to FIGS. 37-38, with continuing reference to FIG. 21, at step 274-24 the instrument(s), including the trajectory assembly 450, may be removed from the surgical site S. One or more cutting guides 478 may be positioned adjacent to the bone 376-1 relative to the surgical site S. The cutting guide 478 may be positioned according to the trajectories T1, T1 of the guide pins GP-1, GP-2 (FIG. 37). The cutting guide 478 can include one or more slots dimensioned to receive tooling TT such as a saw (FIG. 38). Step 274-25 may include positioning the cutting guide 478 along the guide pins GP-1, GP-2. The cutting guide 478 may establish one or more resection planes RP (shown in dashed lines in FIG. 38). Each resection plane RP may be associated with one of the reference planes REF of the respective bone model 129 (FIG. 4). At step 274-26, a portion of the bone 376-1 may be resected along the resection plane RP to establish a resection surface 376RS of the bone 376-1, as illustrated in FIG. 38.

Step 274-26 may include forming one or more relief cuts in the first bone 376-1 and/or second bone 376-2. The relief cuts may be formed to at least partially or substantially remove the overlapping volumes determined at step 274-16 and associated modified bone models 129-1" and/or 129-2" established at step 274-17.

Referring to FIGS. 39-40, with continuing reference to FIG. 21, the cutting guide 478 can be removed from the surgical site S. At step 274-27, the resection surfaces 376RS of the first and second bones 376-1, 376-2 may be moved into abutment. Step 274-27 may include positioning the bones 376-1, 376-2 to establish a contact area that substantially corresponds to the contact region CR of the associated surgical plan 131 (see, e.g., FIGS. 2 and 6). Step 274-27 may include positioning the bones 376-1, 376-2 to establish cortical-to-cortical contact along the resection surfaces 376RS that substantially corresponds to the localized support regions LSR of the associated surgical plan 131 (see, e.g., FIGS. 6 and 9-10). The surgeon may adjust the relative position between the resection surfaces 376RS of the bones 376-1, 376-2.

At step 274-28, one or more implants 380 may be positioned relative to the bones 376-1, 376-2. The implant 380 may be associated with an implant model 130 of the surgical plan 131 (see, e.g., FIGS. 2 and 12-13). Step 274-28 may occur subsequent to moving the resection surfaces 376RS of the bones 376-1, 376-2 into abutment. The implant 380 may be positioned to span across an interface between the bones 376-1, 376-2.

At step 274-29, the implant(s) 380 may be secured to the bones 376-1, 376-2. Various techniques may be utilized to secure the implant 380, including one or more fasteners F (FIG. 40). Exemplary fasteners can include nails, pins, locking and/or non-locking compression screws, suture, etc. At step 274-30, one or more finishing operations may be performed. Exemplary finishing operations may include closing an incision at the surgical site S.

The novel devices and methods of this disclosure provide versatility in dimensioning or shaping resection surfaces at a surgical site. The disclosed planning systems and methods may be utilized to determine resection characteristics and sufficiency of contact surfaces to promote bone fusion and stability. The surgeon or assistant may interact with the disclosed planning systems to set and adjust the resection characteristics, including adjusting resection planes associated with the selected bone models. The disclosed planning systems and methods may present the surgeon or assistant with parameters associated with the selected resection planes and other characteristics, including parameters associated with a contact area between the adjacent resection surfaces, cortical and cancellous coverage, and shortening of the respective bones, which may be utilized to establish relatively greater contact areas and improve bone fusion and healing at the surgical site. The disclosed trajectory assemblies, including the disclosed trajectory guides and secondary guides, may precisely establish trajectories of guide members inserted into bone, which can be utilized to more accurately form resection surfaces according to a preoperative plan established for the patient.

The disclosed systems and methods can facilitate implant and screw positioning, osteotomy position on adjacent bones including a tibia and talus in a manner that improves surface coverage. The disclosed trajectory assemblies and cutting guides may be reusable and may be configured according to settings established in a surgical plan. The disclosed systems and methods can be utilized to reduce operative time and complexity.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A system for planning an orthopaedic procedure comprising:
   a computing device including a processor coupled to a memory, and software planning instructions stored in the memory and executable by the processor, the software planning instructions including a display module, a spatial module and a comparison module such that when the software planning instructions are executed by the processor, the processor:
   stores a plurality of bone models including a first bone model and a second bone model in the memory;
   displays the first bone model and the second bone model in a graphical user interface using the display module;
   establishes, using the spatial module, a first resection surface of the first bone model according to a first reference plane;
   establishes, using the spatial module, a second resection surface of the second bone model along a second reference plane;
   positions, using the spatial module, the first resection surface in contact with the second resection surface along a contact region;
   determines, using the comparison module, a contact area ratio defined as a first area of the first resection surface along the contact region divided by a second area of the second resection surface; and
   generates, using the comparison module, a first indicator in response to one or more predetermined criteria being met, the one or more predetermined criteria including the contact area ratio meeting a first predefined threshold in the software planning instructions.

2. The system as recited in claim 1, wherein the first area is less than the second area, and the first predefined threshold is greater than or equal to 0.4.

3. The system as recited in claim 2, wherein when the software planning instructions are executed by the processor, the processor:
   displays, using the display model, the first indicator in the graphical user interface in response to the one or more predetermined criteria being met.

4. The system as recited in claim 3, wherein when the software planning instructions are executed by the processor, the processor:

displays, using the display model, a value of the contact area ratio in the graphical user interface.

5. The system as recited in claim 2, wherein the first bone model is associated with a talus, and the second bone model is associated with a tibia.

6. The system as recited in claim 1, wherein when the software planning instructions are executed by the processor, the processor:
   determines a contact to resection ratio using the comparison module, wherein the contact to resection ratio is defined as the first area of the first resection surface along the contact region divided by the first area, and wherein the one or more predetermined criteria include the contact to resection ratio being greater than or equal to 0.75.

7. The system as recited in claim 1, wherein when the software planning instructions are executed by the processor, the processor:
   causes, using the spatial module, relative movement between the first resection surface and the second resection surface along the contact region in response to user interaction; and
   updates, using the comparison module, a value of the contact area ratio in response to the relative movement.

8. The system as recited in claim 1, wherein when the software planning instructions are executed by the processor, the processor:
   sets, using the spatial module, a position of the first reference plane with respect to the first bone model in response to user interaction; and
   sets, using the spatial module, a position of the second reference plane with respect to the second bone model in response to user interaction.

9. The system as recited in claim 1, wherein when the software planning instructions are executed by the processor, the processor:
   displays, using the display module, in a first display window of the graphical user interface the first and second bone models relative to a first image plane; and
   sets, using the display module, the first image plane to be parallel to the first and second reference planes such that the contact region is displayed along the first image plane in the first display window.

10. The system as recited in claim 9, wherein when the software planning instructions are executed by the processor, the processor:
    displays, using the display module, a visual contrast between the contact region and a remainder of the first and second resection surfaces that excludes the contact region.

11. The system as recited in claim 9, wherein when the software planning instructions are executed by the processor, the processor:
    determines, using the comparison module, a set of values of the contact area ratio associated with different positions of the first bone model relative to the second bone model along the contact region, with values in the set of values of the contact area ratio corresponding to respective directions from a contact axis intersecting the contact region; and
    displays, using the display module, a first directional indicator extending in a first direction relative to the contact axis, the first direction associated with a maximum value of the set of values of the contact area ratio.

12. The system as recited in claim 1, wherein when the software planning instructions are executed by the processor, the processor:
    establishes, using the spatial module, a first outer perimeter and a first inner perimeter of the first bone model along the first reference plane, the first inner and outer perimeters are associated with respective first inner and outer profiles of a cortical wall associated with the first bone model, wherein the first inner perimeter is associated with a first cancellous area of the first bone model, and the first cancellous area corresponds to an area along the first reference plane surrounded by the first inner perimeter;
    establishes, using the spatial module, a second outer perimeter and a second inner perimeter of the second bone model along the second reference plane, wherein the second inner and outer perimeters are associated with respective second inner and outer profiles of a cortical wall associated with the second bone model, the second inner perimeter is associated with a second cancellous area of the second bone model, the second cancellous area corresponds to an area along the second reference plane surrounded by the second inner perimeter;
    determines, using the comparison module, a cancellous coverage ratio defined as an area of overlap between the first and second cancellous areas divided by the first cancellous area; and
    generates, using the comparison module, a second indicator in response to the cancellous coverage ratio meeting a second predefined threshold in the software planning instructions.

13. The system as recited in claim 12, wherein the second predefined threshold is equal to or greater than 0.75.

14. The system as recited in claim 12, wherein when the software planning instructions are executed by the processor, the processor:
    determines, using the spatial module, a first cortical area and a second cortical area, wherein the first cortical area corresponds to an area between the first inner and outer perimeters along the contact region, and the second cortical area corresponds to an area between the second inner and outer perimeters along the contact region;
    determines, using the comparison module, a cortical coverage area defined as an area of overlap between the first and second cortical areas divided by the first cortical area; and
    generates, using the comparison module, a third indicator in response to the cortical coverage ratio meeting a third predefined threshold in the software planning instructions.

15. The system as recited in claim 14, wherein the third predefined threshold is equal to or greater than 0.03.

16. The system as recited in claim 12, wherein one of the first and second bone models is associated with a talus, and another one of the first and second bone models is associated with a tibia.

17. The system as recited in claim 16, wherein the first bone model is associated with a talus, and the second bone model is associated with a tibia.

18. The system as recited in claim 1, wherein when the software planning instructions are executed by the processor, the processor:
    establishes, using the spatial module, a first outer perimeter and a first inner perimeter of the first bone model along the first reference plane, and wherein the first inner and outer perimeters are associated with respective first inner and outer profiles of a cortical wall associated with the first bone model;

determines, using the spatial module, a first cortical area and a first boundary area, wherein the first cortical area corresponds to an area between the first inner and outer perimeters along the contact region, and the first boundary area corresponds to the area between the first inner and outer perimeters; and determines, using the comparison module, a cortical support ratio defined as the first cortical area divided by the first boundary area, and wherein the one or more predetermined criteria include the cortical support ratio being greater than or equal to 0.50.

19. The system as recited in claim 18, wherein when the software planning instructions are executed by the processor, the processor:

establishes, using the spatial module, a second outer perimeter and a second inner perimeter of the second bone model along the second reference plane, wherein the second inner and outer perimeters are associated with respective second inner and outer profiles of a cortical wall associated with the second bone model;

determines, using the spatial module, a second boundary area corresponding to the area between the second inner and outer perimeters;

establishes, using the spatial module, at least four localized support regions along the first boundary area; and generates, using the comparison module, a support indicator in response to a predefined support threshold being met, wherein the predefined support threshold is defined in the software planning instructions as a quantity of three localized support regions in which contact between the first and second boundary areas is established.

20. The system as recited in claim 1, wherein when the software planning instructions are executed by the processor, the processor:

determines, using the spatial module, a first distance along a longitudinal axis between a first end and a second end of the second bone model;

determines, using the spatial module, a second distance along the longitudinal axis between the second reference plane and the second end of the second bone model;

determines, using the comparison module, a length ratio in response to setting a position of the second reference plane, wherein the length ratio is defined as a ratio of the second distance divided by the first distance; and generates, using the comparison module, a fourth indicator in response to the length ratio being less than a predefined length threshold.

21. The system as recited in claim 20, wherein the predefined length threshold is less than or equal to 0.01.

22. The system as recited in claim 1, wherein when the software planning instructions are executed by the processor, the processor:

determines, using the spatial module, a first trajectory associated with a first guide pin and a second trajectory associated with a second guide pin in response to the one or more predetermined criteria being met; and associates the first and second trajectories with respective first and second positions along one of the first and second bone models relative to the contact region.

23. The system as recited in claim 22, wherein when the software planning instructions are executed by the processor, the processor:

generates, using the comparison module, one or more settings associated with a trajectory assembly based on the first and second trajectories.

24. The system as recited in claim 23, wherein the trajectory assembly comprises:

a trajectory guide including a guide body and at least one arm member coupled to the guide body, the guide body including a guide passage extending along a passage axis, and the at least one arm member moveable relative to the guide body to set a trajectory of the first guide pin based on the first trajectory, the first guide pin insertable through the guide passage relative to bone; and a secondary guide including a main body having at least one aperture, the at least one aperture dimensioned to at least partially receive the second guide pin along an aperture axis based on the second trajectory, and the secondary guide coupled to the guide body such that the aperture axis is offset from the passage axis.

25. The system as recited in claim 24, wherein the aperture axis is substantially parallel to the passage axis.

26. The system as recited in claim 24, wherein the main body extends along a guide axis, and the at least one aperture includes a first row of apertures distributed about the guide axis.

27. The system as recited in claim 26, wherein the at least one aperture includes a second row of apertures distributed about the guide axis, the second row of apertures being outward of the first row of apertures relative to the guide axis.

28. The system as recited in claim 27, wherein each aperture of the first row of apertures is substantially circumferentially aligned with a respective aperture of the second row of apertures relative to the guide axis.

29. The system as recited in claim 24, wherein the main body includes a sleeve portion and a flange portion extending outwardly from a perimeter of the sleeve portion, the at least one aperture is established along the flange portion, and the sleeve portion has a sleeve passage dimensioned to at least partially receive a proximal end portion of the guide body.

30. The system as recited in claim 29, wherein the trajectory guide includes an abutment along an outer periphery of the guide body, and the secondary guide is translatable along the passage axis to engage the abutment such that relative movement between the secondary guide and guide body is limited relative to the passage axis.

31. The system as recited in claim 30, wherein the trajectory guide includes a first interface feature along the guide body, the secondary guide includes a second interface feature along the sleeve portion, and the first interface feature is dimensioned to engage with the second interface feature to limit relative rotation between the guide body and the secondary guide.

32. The system as recited in claim 31, wherein the first interface feature is a protrusion extending outwardly from the outer periphery of the guide body, and the second interface feature includes at least one groove along the sleeve passage of the sleeve portion, and the protrusion is insertable in the at least one groove to limit relative rotation between the guide body and the secondary guide.

33. The system as recited in claim 32, wherein the at least one groove includes an array of grooves distributed along the sleeve passage of the sleeve portion, and the protrusion is insertable within a selected one of the grooves to set a circumferential position of the at least one aperture relative to the passage axis.

34. The system as recited in claim 1, wherein:

the memory is configured to store at least one implant model; and when the software planning instructions are executed by the processor, the processor:
- positions, using the spatial module, the at least one implant model relative to the first and second bone models in response to user interaction;
- determines, using the spatial module, one or more overlapping volumes between the at least one implant model and the first and second bone models;
- displays, using the display module, the at least one implant model in the graphical user interface; and
- displays, using the display module, a visual contrast between the one or more overlapping volumes and a remainder of the volumes of the first and second bone models that excludes the one or more overlapping volumes.

35. The system as recited in claim 34, wherein when the software planning instructions are executed by the processor, the processor:
- generates, using the spatial module, an iteration of the first and second bone models that excludes the one or more overlapping volumes; and
- displays, using the display module, the at least one implant model positioned relative to the iteration of the first and second bone models.

\* \* \* \* \*